(12) United States Patent
Patil et al.

(10) Patent No.: US 11,031,098 B2
(45) Date of Patent: Jun. 8, 2021

(54) COMPUTER SYSTEMS AND METHODS FOR GENOMIC ANALYSIS

(71) Applicant: GENETIC TECHNOLOGIES LIMITED, Fitzroy (AU)

(72) Inventors: Nila Patil, Woodside, CA (US); David R. Cox, Belmont, CA (US); Anthony J. Berno, San Jose, CA (US); David A. Hinds, Mountain View, CA (US)

(73) Assignee: Genetic Technologies Limited, Fitzroy (AU)

(*) Notice: Subject to any disclaimer, the term of this patent is extended or adjusted under 35 U.S.C. 154(b) by 664 days.

(21) Appl. No.: 15/169,498

(22) Filed: May 31, 2016

(65) Prior Publication Data

US 2016/0371429 A1 Dec. 22, 2016

Related U.S. Application Data

(63) Continuation of application No. 12/795,361, filed on Jun. 7, 2010, now abandoned, which is a continuation of application No. 11/172,341, filed on Jun. 29, 2005, now abandoned, which is a continuation of application No. 10/106,097, filed on Mar. 26, 2002, now Pat. No. 6,969,589.

(60) Provisional application No. 60/280,530, filed on Mar. 30, 2001, provisional application No. 60/313,264, filed on Aug. 17, 2001, provisional application No. 60/327,006, filed on Oct. 5, 2001, provisional application No. 60/332,550, filed on Nov. 26, 2001.

(51) Int. Cl.
| | |
|---|---|
| *C12Q 1/68* | (2018.01) |
| *G16B 30/00* | (2019.01) |
| *G16B 40/00* | (2019.01) |
| *C12Q 1/6827* | (2018.01) |

(52) U.S. Cl.
CPC .......... *G16B 30/00* (2019.02); *C12Q 1/6827* (2013.01); *G16B 40/00* (2019.02); *Y10T 436/143333* (2015.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 5,143,854 A | 9/1992 | Pirrung et al. |
| 5,384,261 A | 1/1995 | Winkler et al. |
| 5,405,783 A | 4/1995 | Pirrung et al. |
| 5,412,087 A | 5/1995 | McGall et al. |
| 5,424,186 A | 6/1995 | Foder et al. |
| 5,445,934 A | 8/1995 | Foder et al. |
| 5,459,325 A | 10/1995 | Hueton et al. |
| 5,512,462 A | 4/1996 | Cheng |
| 5,527,681 A | 6/1996 | Holmes |
| 5,571,639 A | 11/1996 | Hubbell et al. |
| 5,578,832 A | 11/1996 | Trulson et al. |
| 5,593,839 A | 1/1997 | Hubbell et al. |
| 5,677,195 A | 10/1997 | Winkler et al. |
| 5,744,305 A | 4/1998 | Foder et al. |
| 5,800,992 A | 9/1998 | Foder et al. |
| 5,831,070 A | 11/1998 | Pease et al. |
| 5,837,832 A | 11/1998 | Chee et al. |
| 5,861,242 A | 1/1999 | Chee et al. |
| 5,953,727 A | 9/1999 | Maslyn et al. |
| 5,972,614 A | 10/1999 | Ruano et al. |
| 5,981,956 A | 11/1999 | Stern |
| 6,007,231 A | 12/1999 | Vijg et al. |
| 6,027,880 A | 2/2000 | Cronin et al. |
| 6,040,138 A | 3/2000 | Lockhart et al. |
| 6,040,193 A | 3/2000 | Winkler et al. |
| 6,150,094 A | 11/2000 | Maier et al. |
| 6,214,557 B1 | 4/2001 | Barnes et al. |
| 6,228,575 B1 | 5/2001 | Gingeras et al. |
| 6,231,812 B1 | 5/2001 | Rothberg et al. |
| 6,262,838 B1 | 7/2001 | Montagu |
| 6,300,063 B1 | 10/2001 | Lipshutz et al. |
| 6,391,559 B1 | 5/2002 | Brown et al. |
| 6,521,747 B2 | 2/2003 | Anastasio et al. |
| 6,740,510 B2 | 5/2004 | Kauzer et al. |
| 6,897,025 B2 | 5/2005 | Cox et al. |
| 6,898,531 B2 | 5/2005 | Sheehan et al. |
| 6,931,326 B1 | 8/2005 | Judson et al. |

(Continued)

FOREIGN PATENT DOCUMENTS

| | | |
|---|---|---|
| DE | 10062566 | 6/2002 |
| EP | 0717113 | 6/1996 |

(Continued)

OTHER PUBLICATIONS

"Expand Long Template PCR System," Specification, ROCHE, Jun. 1999, 4 pp., verso 3.
"Expand Long Template PCR System," Specification, ROCHE, Sep. 1999, 5 pp., verso 4.
"Long-Range PCR using the Expand Long Template PRC Kit," Boehringer Mannheim, 1999, 2 pages.
Adkins et al. "Genome-wide pharmacogenomic study of citalopram-induced side effects in STAR*D," Transl Psychiatry, 2012, vol. 2, e129, 9 pages.

(Continued)

*Primary Examiner* — Frank W Lu
(74) *Attorney, Agent, or Firm* — Sheridan Ross P.C.

(57) ABSTRACT

The present invention relates to methods for identifying variations that occur in the human genome and relating these variations to the genetic basis of disease and drug response. In particular, the present invention relates to identifying individual SNPs, determining SNP haplotype blocks and patterns, and, further, using the SNP haplotype blocks and patterns to dissect the genetic bases of disease and drug response. The methods of the present invention are useful in whole genome analysis.

8 Claims, 19 Drawing Sheets

Specification includes a Sequence Listing.

(56) References Cited

U.S. PATENT DOCUMENTS

| | | | |
|---|---|---|---|
| 6,969,589 | B2 | 11/2005 | Patil et al. |
| 2002/0012921 | A1 | 1/2002 | Stanton |
| 2003/0170665 | A1 | 9/2003 | Daly et al. |
| 2004/0023237 | A1 | 2/2004 | Cox et al. |
| 2004/0146870 | A1 | 7/2004 | Liao et al. |
| 2005/0272086 | A1 | 12/2005 | Patil et al. |
| 2011/0020815 | A1 | 1/2011 | Patil et al. |

FOREIGN PATENT DOCUMENTS

| | | |
|---|---|---|
| EP | 0950720 | 10/1999 |
| EP | 1246114 | 10/2002 |
| WO | WO 92/04470 | 3/1992 |
| WO | WO 92/10092 | 6/1992 |
| WO | WO 95/06764 | 3/1995 |
| WO | WO 95/11995 | 5/1995 |
| WO | WO 95/23225 | 8/1995 |
| WO | WO 95/25117 | 9/1995 |
| WO | WO 97/10365 | 3/1997 |
| WO | WO 97/15070 | 4/1997 |
| WO | WO 97/27317 | 7/1997 |
| WO | WO 97/29212 | 8/1997 |
| WO | WO 98/56954 | 12/1998 |
| WO | WO 99/11823 | 3/1999 |
| WO | WO 99/52942 | 10/1999 |
| WO | WO 00/28080 | 5/2000 |
| WO | WO 01/01218 | 1/2001 |
| WO | WO 01/04270 | 1/2001 |
| WO | WO 01/80156 | 10/2001 |
| WO | WO 2002/027034 | 4/2002 |

OTHER PUBLICATIONS

Agarwal, P., et al, ° Comparison study for identifying promoter allelic polymorphism in interleukin 10 and tumor necrosis factor alpha genes, Diagn Mol Pathol9,158-64 (2000).
Akasaka, T., et al, "LOng distance polymerase chain reaction for detection of chromosome translocations in . . . ," Leukemia Apr. 1997, cover pp and pp. 316-317, vol. 11, supp. 3.
Akasaka, T., et al, "Polymerase chain reaction amplification of long DNA targets . . . ," Inti Journal of Oncology, 1998, pp. 113-121, vol. 12.
Altshuler, D., Daly, M., KRtJGLYAK, L., iGuilt by Association, Nature Genetics26, 135-137 (2000).
Altshuler, D., et al, "An SNP map of the human genome generated by . . . reduced representation shotgun sequencing," Nature 407,513-516 (2000).
Altshuler, D., et al, "The common PPAR Prol2Ala po~orphismis associated with decreased risk of type 2 diabetes," Nature Genetics 26, pp. 76-80 (2000).
Arnold, B.A., et al, "One-Step Flouresecent Probe Product~Enhanced Reverse Transcriptase Assay," BioTechniClues 25:98-106 (1998).
Barany, F., "Single-stranded hexameric linkers: a system for in-phase insertion mutagenesis and protein engineering," Gene 37,111-123 (1985).
Barnes, WM., "PCR amplification of up to 35-kb DNA w/high fidelity and high yield . . . ," Proc. Natl. Acad. Sci. USA, Mar. 1994, pp. 2216-2220, vol. 91, Genetics.
Barton et al. "Site directed, recombination-mediated mutagenesis of a complex gene locus," Nucleic Acids Research 18:7349-7355 (1990).
Barton et al. "A Functional Haplotype of the PADI4 Gene Associated With Rheumatoid Arthritis in a Japanese Population Is Not Associated in a United Kingdom Population," Arthritis & Rheumatism, Apr. 2004, vol. 50, No. 4, pp. 1117-1121.
Bashkin, J.K., et~, "Ribozyme Mimics as Catalytic Antisense Reagents," Applied Biochemistry and Biotechnology 54, 43-56 (1995).
Becker, K., et al., "Real-Time Quantitative Polymerase Chain Reaction to Assess gene Transfer," Human Gene Therapy 10:2559-2566 (1999).

Beigelman, et al., "Synthesis of 2'-modified nucleotides and their incorporation into hammerhead ribozymes", Nucleic acids research, 23: 4434-4442, (1995).
Beitelshees et al. "CACNA1C gene polymorphisms, cardiovascular disease outcomes and treatment response," Circ Cardiovasc Genet, Aug. 2009, vol. 2, No. 4, pp. 362-370.
Boehringer Mannheim, PCR Applications Manual, Boehringer Mannheim GmbH, Biochemica, Germany, pp. 23, 27-53 & 109 (1995).
Cardon, L.R, Bell, J.I., "Association Study Designs for Complex Diseases," Nature 2,91-99 (2001).
Cargill, M., Daley, G.Q., "Mining for SNPs: putting the common variants-common disease hypothesis to the test," Pharmacogenomics. 1(1):27-37, (2000).
Chee, M., et al, "Accessing Genetic Information with High-Density DNA Arrays," Science Magazine 274,610-614 (1996).
Cheng, S., et al, "Effective amplification of long targets from cloned inserts and human genomic DNA," Proc. Natl. Acad. Sci. USA, Jun. 1994, pp. 5695-5699, vol. 91, Genetics.
Cheng, S., et al, "LongPCR," Nature, Jun. 23, 1994, pp. 684-685, vol. 369.
Cheng, S., et al, "XLPCR amplification of long targets from genomic DNA," PCR Cloning Protocols: From Molecular Cloning to Genetic Engineering, 1997, vol. 67, pp. 17-29.
Clark, A.G., et al, "Haplotype Structure and Population Genetic Inferences from Nucleotide-Sequence Variation . . . ;" The American Society ofHuman Genetics 63, 595-612 (1998).
Cohen, J., "Long PCR'leaps into larger DNAsequences," science, Mar. 18, 1994, pp. 1564-1565, vol. 263.
Colicelli, J., et al, "A temperature-sensitive mutation constructed by "linker insertion" mutagenesis," Mol Gen Genet 199:537-539 (I985).
Cooksey, et al, "Evaluation of the Invader assay, a linear signal amplification method, for ide~ification of mutations . . . ," Antimicrob AgentsChemother 44, 1296-301 (2000).
Cormen, T.H., et al, "Contents—Introduction to Algorithms," 1994; pp. 329-355,514-578; MIT Press.
Cutler, DJ., et al, "High-Throughput Variation Detection and Genotyping Using Microarrays," Genome Research 11,1913-1925 (2001).
Daly et al., "Creating an LD map ofa long genomic region", Am. J. Hum. Genet., vol. 67, No. 4, Supplement 2, Oct. 2000, pp. 224.
Daly, M.J., RiOux, J.D., SCHAfFNER, S.F., Hudson, TJ., Lander, E.S., High-resolution haplotype structure in the human g~nome, Nature Genetics 29,229-232 (2001).
Deenen et al. "Relationship between Single Nucleotide Polymorphisms and Haplotypes in DPYD and Toxicity and Efficacy of Capecitabine in Advanced Colorectal Cancer," Clinical Cancer Research, 2011, vol. 17, pp. 3455-3468.
Doi, K.; et al, "Greedy Algorithms for Finding a Small Set of Primers Satisfying Cover and Length Resolution Conditions in PCR Experiments," Genome Informatics Series 8:43-52.
Doll, J,J., The Patenting of DNA, Science Magazine 280, 689~690 (1998).
Douglas, et al., "Experimentally-derived haplotypessubstantially increase the efficiency of linkage disequilibrium studies", Nature Genetics, 28: 361-364, (2001).
Drysdale, C.M.,et al, "Complex promoter and coding region beta 2-adrenergic receptor haplotypes alter receptor expression . . . ," Proc Nat Acad of Sci USA 97(19):10483-8(2000).
Evans, W.E., Relling, M.V., "Pharacogenetics: Translating Functional Genomics into Rational Therapeutics," Science Magazine 286, 487-491 (1999).
Foord, et al, "PCR Methods and Applications" vol. 3:S149-S161 (1994).
Fu "Statistical Tests of Neutrality of Mutations," Genetics 133: 693-709 (1993).
Fullerton, S.M. et al, "ApolipoproteinE Variation at the Sequence Haplotype Level: Implications for the Origin . . . ," The American Society ofHuman Genetics 67, 881-900 (2000).
Furth et al., "Gene Transfer into Somatic 11ssues by Jet Injection," Analytical Biochemistry 205, 365-368 (1992).
Gaudieri, et al., "SNP profile within the major histocompatibility complex reveals an extreme and interrupted level of nucleotide diversity", Genome Research, vol. 10, 2000, pp. 1579-1586.

(56) References Cited

OTHER PUBLICATIONS

Gorelenkov, et al., "Set of novel tools for PCR primer design", Biotechniques 31(6): 1326-1330, (2001).
Gustin, K.E., Burk.,RD.,"ARapid Method for Generating Linker Scanning Mutants Utilizing PCR," BioTechniqu~ 14:22-23 (1993).
Hall, J.G. et al, "Sensitive detection ofDNA polymorphisms by the serial invasive signal amplification reaction," Proc Natl Acad Sci US A 97,8272-8277 (2000).
Hartl, D.L., et al, "Principles of Population Genetics," Third Edition, 1998, pp. 37-69.
Hengen, P.N., "Long and accurate PCR," TiBS, 1994, cover and p. 341, vol. 19, Inti Union of Bim::hemistry & Elsevier Trends Journal.
Hessner et al. "Genotyping of factor V G1691A (Leiden) without the use of PCR by invasive cleavage of oligonucleotide probes," Clin Chem, 2000, vol. 46, pp. 1051-1056.
Hussar "Overview of Response to Drugs, Merck Manuals Consumer Version," Merck Sharp & Dohme Corp., 2015, 2 pages [retrieved from: www.merckmanuals.com/home/drugs/factors-affecting-response-to-drugs/overview- . . . ].
Cleavage of Oligonucleotide Probes, Clin Chem 46, 1051-6 (2000).
Jeffreys et al. "High resolution analysis of haplotype diversity and meiotic crossover in the human TAP2 recombination hotspot," Human Molecular Genetics, 2000, vol. 9, pp. 725-733.
TAP2 . . . , Human Molecular Genetics 9,725-733 (2000).
Jones, D.H., Winistorfer, S.C., "Recombinant Circle PCR and Recombination PCR for Site-Specific Mutagenesis Without PCR Proouct Purification," BioTechniques 12:528-530 (1992).
Jorde, L.B., "Linkage Disequilibrium and the Search for Complex Disease Genes,"•Genome Research 10, 1435-1444 (2000).
Judson, R, et al, "Notes from the SNP vs. haplotype front," Pharmacogenomics. 2(1):1-7 (2001).
Judson, R, et al, "The predictive power of haplotypes in clinical response," Pharmacogenomics 1(1): 15-26, (2000).
Kallioniemi,O., "Biochip technologies in cancer research," Annals of Medicine 33, 142-1247 (2001).
Kampte, T., et al, "Efficient primer design algorithms," Bioinformatics 17 (3):214-225 (2001).
Karetet al, "Unraveling Human Diversity," Drug Discovery& Development Magazine NovemberIDecember S5-S14 (2000).
Kota, R., et al, "Application of denaturing high-performance .liquid chromatography for mapping of single nucleotide polymorphisms in barley . . . ," Genome 44: 523-528, (2001).
Kruglyak, L., "Prospects for whole-genome linkage disequilibrium mapping of common disease genes," Nature Genetics 22, 139-144 (1999).
Kruglyak, L., Nickerson, D.A., "Variation is the spice oflife," Nature Genetics 27, 234-236 (2001).
Lai, E., "Application of SNP Technologies in Medicine: Lessons Learned and Future Challenges," Genome Research 1, 927-929 (2001).
Lander,E.S., "The New Genomics: Global Views of Biology," Science Magazine 274,536-539 (1996).
Lay, J.M., et al, "Rapid confirmation of gene targeting in embryonic stem cells . . . ," Transgenic Research, 1998, pp. 135-140, vol. 7, Chapman & Hall.
Lindberg,A.M., et al, "Amplification and cloning of complete enterovirus . . . ," Journal of Virological Methods 1997, pp. 191-199, vol. 65, Elsevier Science BV.
Lizardi et al, "Mutation detection and single-molecule counting using isothermal rolling-circle amplification," Nature Genetics 19,225-232 (1998).
Lockhart, pJ., Winzeler, EA., "Genomics, gene expression and DNA arrays," Nature 405, 827-836—(2000).
Long PCR Reagents and Guidelines, 3 pp. printed Jun. 15, 2000 from twod.med.harvard.edu.
Loukianov, E.Y., et al, "Identification oftargeted embryonic stem cells using long-distance PCR," BioTechniques, Sep. 1997, pp. 376-380, vol. 23.

Luthra, R, et at, "Mapping ofgenomic I(2;5)(p23;q35) break. points . . . ," Hematopathology and Molecular Hematology, 1998, pp. 173-183, vol. 11, (3&4), Marcel Dekker, Inc.
Hematology, 1998, pp. 173-183, vol. 11 (3&4), Marcel Dekker, Inc.
Maga, EA, et al, "Amplification of a 9.Q-kb fragment using PCR," BioTechniques, Jul. 1991, index and pp. 185-186, vol. 11, No. 1, Eaton Publishing Co.
Mancinelliet al., Pharmacogenomics: The Promise of Personalized Medicine. AAPS PharmSci., 2, 1-13, 2000.
Marth, G., et al, "Single-nucleotide polymorphisms in the public domain: how useful are they?" Nature Genetics 27, 371-372 (2001).
McCarthy et al. "The use of single-nucleotide polymorphism maps in pharmacogenomics," NatureBiotechnology 18,505-508 (2000).
Min, G-S, et al, "Long-distance genome walking using the long and accurate polymerase chain react~on," BioTechniques, 1998, pp. 398-400, vol. 24, No. 3 . . . .
Newton, CR, PCR Essential Data, published by Wiley & Sons, Inc. New York, pp. 24, 25, 53, 72-86, (1995).
Oesrreicher, P., "4th Annual Pharrnacogenomics and Medicine Lectures," Pharmacogenomics 2 (3):291-296 (2001).
Ohler, L.D., et al, "Optimization oflong-distance PCR using a transposon-based . . . , PCR Method and Applications," 1992, pp. 51-59, vol. 2, Cold Spring Harbor Lab. Press.
Ohya, Y., "LA-PCR-based Quick Method for Identification ofGenes Resp. for Complementation of_Saccharomyces cerevisiae Mutations," BioTech; May 1996; pp. 772-778, vol. 20, No. 5.
Pacanowski et al. "β-Adrenergic Receptor Gene Polymorphisms and β-Blocker Treatment Outcomes in Hypertension," Clin Pharmacol Ther. Dec. 2008, vol. 84, No. 6, pp. 715-721.
Pandey, A., Mann, M., "Proteomics to study genes and genomes," Nature 405, 837-846 (2000).
Patterson, D., et at, "Somatic Cell C'Jelletic Approaches to Down's Syndrome," The New York Academy of Sciences 396, 69-81, (1982).
Pennacchio, LA., Rubin, E.M., "Genomic Strategies to IdentifY Mammalian Regulatory Sequences," Nature 2, 100-109 (2001).
Pesole, G., et al, "GeneUp: A Program to Select Short peR Primer Pairs that Occur in Multiple Members of Sequence Lists," BioTechniques 25:112-123 (1998).
Plasterer, T., "Primerselect: Primer and Probe design," Methods in Molecular Biology 70:291-302 (1997)-.
Ponce, M.R. et al, "PCR amplification of long DNAfragments," Nucleic Acid Research, 1992, pp. 623, vol. 20, No. 3, Oxford Univ. Press.
Prentki, P., Krisch, H.M., "In vitro insertional mutagenesis with a selectable DNAfragment," Gene 29:303-313 (1984).
Primer3, 5 pp. printed Nov. 26, 2001 from www"genome.wLmiLedu.
Proutski, V., et al, "Primer Master: a new program for the design and analysis ofPCR primers," Cabios 12(3):253-255(1996).
Radding, C.M., "Homologous Pairing and Strand Exchange in Genetic Recombination," Ann. Rev. Genet. 16:405-437 (1982).
Reich, D.E., et al, "Linkage disequilibrium in the human genome," Nature 411, 199-204 (2001).
Riley, J .H., et al, "The use of single nucleotide polymorphismsin the isolation of common disease genes," Pharmacogenomics 1(1):39-47, (2000).
Risch, N., Merikangas, K., "The Future of Genetic Studies of Complex Human Diseases," Science Magazine 273,1516-1517 (1996).
Roses, A.D., "Pharmacogenetics," Human Molecular Genetics10, 2261-2267 (2001).
Rothberg, B.E., "Mapping a role for SNPs in drug development," Nature Biotechnology 19, 209-211 (200]).
Sanchez, et al., "Relative amplification effiency of differently sized templates by long-distance PCR, Bio techniques", vol. 24, No. 3, (1998).
Sanchez, G. et a., "Relative Amplification Efficiency of Differently Sized Templates by Long-Distance PCR, BioTechniQues," Mar. 1998; pp. 400-402, vol. 24, No. 3.
Sarkur et al., "Human genetic bi-allelic 39 sequences (BGBASE), a database of intra-genic polymorphisms", Memorias Do Instituto Oswaldo Cruz, Rio De Janeiro, Br, vol. 93, No. 5, Sep. 1998, pp. 693-694.

(56) References Cited

OTHER PUBLICATIONS

Sayers, et al., "Rapid high-efficiency site-directed mutagenesis by the phosphorothioate approach", Bio techniques, 13: 592-596, (1992).
Sayers, Jr, et al, "Rapid High-Efficiency Site-Directed Mutagenesis by the Phosphorothioate Approach," BioTechniques 13,592-596 (1992).
Selected part of an online Manual from Merck, Section: Drugs. Printed on Dec. 6, 2009 (www.merck.com/mmbe/sec02/ch013/ch013d.html).
Sepehr et al., Genetic polymorphisms in three Iranian populations with different risks of esophageal cancer, an ecological comparison. Caner Letter, 195-202, 2004.
Shapero, M.H., et al, "SNP Genotyping by Multiplexed Solid-Phase Amplification and Flourescent Minisequencing," Genome Research 11, 1926-1934 (2001).
Shiffman et al. "Genome-Wide Study of Gene Variants Associated with Differential Cardiovascular Event Reduction by Pravastatin Therapy," PLOS One, May 2012, vol. 7, No. 5, e38240, 10 pages.
Shoemaker, D.D., et al, "Experimental annotation of the human genome using microarray technology," Nature 409, 922-927 (2001).
Slavik, "Tight analysis of the greedy algorithm for set cover", Conf Proc Annu ACM Symp Theory Comput (Conference Proceedings o fthe Annual ACM Symposium on Theory of Computing), New York, NY, 1996, pp. 435-441.
Sorokin, A., et al, "A new approach using multiplex long accurate PCR and yeast artificial chromosomes for bacterial . . . ," Genome:1996: pp. 448-453, vol. 6, Cold Spring.
Stephens, J.C et al, "Haplotype Variation and Linkage Disequilibrium in 313 Human Genes;" Science Magazine 293,489-493 (2001).
Taillon-Miller et al "IIJuxtaposed regions of extensive and minimal linkage disequilibrium in human XQ25 and XQ28", Nature (J.enetics, vol. 25, No. 3, Jul. 2000, pp. 324-328.
Takita, Y;, et al, "Applications of the long and accurate polymerase chain reaction method in yeast molecular biology; direct . . . ," Yeast 1997, pp. 763-768, v.B, J. Wiley & Sons.
Tang, D., et al, "Genetic immunization is a simple method for eliciting an immune response," Nature 356, 152-154 (1992).
Taylor, et al., "Polymerase chain reaction: from functional genomics to high-schooL.", Current Opinion if) Biotechnology, pp. 35-42, (1998).
Templeton, AR., et al, "Cladistic Structure Within the Human Lipoprotein Lipase Gene and Its Implications for Phenotypic Association Studies," Genetics 156,1259-1275 (2000).
Toivonen, H., et al, "Data Mining Applied to Linkage Disequilibrium-Mapping," American Journal of Human Genetics Jul. 2000;67(1): 133-45.
Toivonen, H., et al, "Gene Mapping by Haplotype Pattern Mining," IEEE International Symposium on Bio-Informatics and Biomedical Engineering (2000) 99-108.
Wang, D.G., "Large-Scale Identification, Mapping, and Genotyping of Single-Nucleotide Polymorphisms in the Human Genome," Science Magazine 280, 1077-1082 (1998).
Waterston, R.H., et al, "A map of human genome sequence variation containing 1.42 million single nucleotide polymorphisms," Nature 409, 928-933 (2001).
Weiner, M.P., et al, "A method for the site-directed mono- and multi-mutagenesis of double-stranded DNA," Gene 126,35-41 (1993).
Wilton, et al., "Long-range PCR: synthesis of products independent of sizil", Trends in genetics, p. 458, vol. 12, No. 11, (1996).
Yang, Z., et al, "Sampling SNPs," Nature Genetics 26, 13-14 (2000).
Zhang,'L-H, et al, "Long-distance PCR-based strategy for preparing knock-in vectors directly from ES cell genomic DNA," BioTech—_ ques,Nov. 1998, pp. 784-788, vol. 25.
Zhong, X et al, "Visualization of oligonucleotide probes and point mutations in interphase nuclei and DNA. fibers . . . ," PNAs 98, 3940-3945 (2001 ).
Official Action for European Patent Application No. 02251978.9, dated Apr. 11, 2008, 10 pages.
Official Action for Canada Patent Application No. 2,380,047, dated Jan. 19, 2010, 4 pages.
Response to Official Action for Canada Patent Application No. 2,380,047, dated Jul. 14, 2011, 31 pages.
Official Action for Canada Patent Application No. 2,380,047, dated Apr. 16, 2012, 4 pages.
Response to Official Action for Canada Patent Application No. 2,380,047, dated Oct. 16, 2012, 15 pages.
Response to Official Action for European Patent Application No. 02251978.9, dated Jan. 26, 2009, 20 pages.
Official Action for European Patent Application No. 02251978.9, dated Feb. 2, 2012, 6 pages.
Response to Official Action for European Patent Application No. 02251978.9, dated Nov. 26, 2012, 12 pages.
Official Action for U.S. Appl. No. 10/106,097, dated May 5, 2004 7 pages.
Official Action for U.S. Appl. No. 10/106,097, dated Nov. 16, 2004 6 pages.
Notice of Allowance for U.S. Appl. No. 10/106,097, dated Mar. 31, 20054 6 pages.
Official Action for U.S. Appl. No. 11/172,341, dated Mar. 30, 2009 12 pages.
Official Action for U.S. Appl. No. 11/172,341, dated Dec. 11, 2009 15 pages.
Official Action for U.S. Appl. No. 12/795,361, dated Aug. 2, 2012 Restriction Requirement.
Official Action for U.S. Appl. No. 12/795,361, dated Jan. 14, 2013 14 pages.
Official Action for U.S. Appl. No. 12/795,361, dated Sep. 26, 2013 17 pages.
Official Action for U.S. Appl. No. 12/795,361, dated Oct. 1, 2014 17 pages.
Official Action for U.S. Appl. No. 12/795,361, dated Jul. 25, 2015 8 pages.
Official Action for U.S. Appl. No. 10/286,417, dated Dec. 19, 2005 9 pages.
Official Action for U.S. Appl. No. 10/286,417, dated Aug. 4, 2006 12 pages.
Official Action for U.S. Appl. No. 10/286,417, dated Mar. 27, 2007 10 pages.
Beaty et al. "Haplotype diversity in 11 candidate genes across four populations," Genetics, 2005, vol. 171, pp. 259-267.
Martinez et al. "PADI4 polymorphisms are not associated with rheumatoid arthritis in the Spanish population," Rheumatology, 2005, vol. 44, pp. 1263-1266.

|  | 241 | 242 | 243 | 244 | 245 | 246 | 247 | 248 | 249 | 250 | 251 | 252 | 253 |
|---|---|---|---|---|---|---|---|---|---|---|---|---|---|
| SEQ ID NO:1 W | ...A... | G... | A | T... | T... | C... | G... | A | T... | A... | A... | C... | G |
| SEQ ID NO:2 X | ...A... | G... | A | C... | T... | A... | C... | A | T... | A... | A... | C... | G |
| SEQ ID NO:3 Y | ...T... | A... | T | T... | T... | C... | G... | A | T... | A... | A... | C... | G |
| SEQ ID NO:4 Z | ...T... | A... | T | C... | T... | A... | C... | A | A... | T... | C... | A... | C |

| BLOCK EVALUATED | SNP POSITIONS | | | | | | MEET INFORMATIVENESS? |
|---|---|---|---|---|---|---|---|
| | 1 | 2 | 3 | 4 | 5 | 6 | |
| A | 1 | 2 | | | | | YES |
| B | 1 | 2 | 3 | | | | YES |
| C | 1 | 2 | 3 | | | | YES |
| D | 1 | 2 | 3 | 4 | | | NO |
| E | | 2 | | | | | YES |
| F | | 2 | 3 | 4 | | | YES |
| G | | 2 | 3 | 4 | | | YES |
| H | | 2 | 3 | 4 | 5 | | NO |
| I | | 2 | 3 | 4 | | | YES |
| J | | | 3 | 4 | | | NO |
| K | | | | 4 | 5 | | YES |
| L | | | | 4 | 5 | | YES |
| M | | | | 4 | 5 | 6 | YES |

BLOCKS SELECTED FOR CANDIDATE SET: A B C E F G I K L M

| Chr21 HuSNP MARKERS | HAMSTER | CPD17 | HYBRID 1 | HYBRID 2 |
|---|---|---|---|---|
| WIAF-3497 | NO SIGNAL | A | A | A |
| WIAF-3498 | NO SIGNAL | AB | A | B |
| WIAF-599 | NO SIGNAL | A | A | A |
| WIAF-3562 | NO SIGNAL | NO SIGNAL | A | B |
| WIAF-559 | NO SIGNAL | AB | B | A |
| WIAF-4546 | NO SIGNAL | AB | B | A |
| WIAF-3508 | NO SIGNAL | B | B | B |
| WIAF-624 | NO SIGNAL | B | B | B |
| WIAF-1500 | NO SIGNAL | A | A | A |
| WIAF-3496 | NO SIGNAL | AB | A | B |
| WIAF-1943 | NO SIGNAL | A | A | A |
| WIAF-2477 | NO SIGNAL | NO SIGNAL | NO SIGNAL | A |
| WIAF-1538 | NO SIGNAL | B | NO SIGNAL | B |
| WIAF-3479 | NO SIGNAL | A | A | NO SIGNAL |
| WIAF-2436 | NO SIGNAL | A | A | A |
| WIAF-1857 | NO SIGNAL | AB | B | A |
| WIAF-899 | NO SIGNAL | AB | A | B |
| WIAF-1682 | NO SIGNAL | B | B | B |
| WIAF-2214 | NO SIGNAL | AB | A | B |
| WIAF-2643 | NO SIGNAL | NO SIGNAL | A | NO SIGNAL |
| WIAF-4514 | NO SIGNAL | B | B | B |

Fig. 11

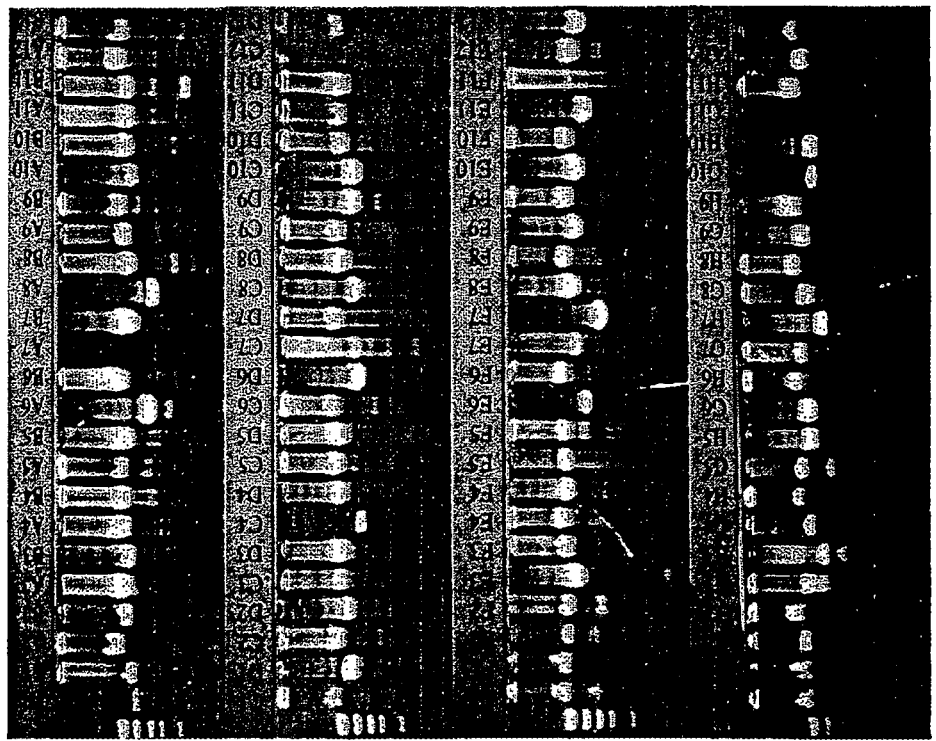
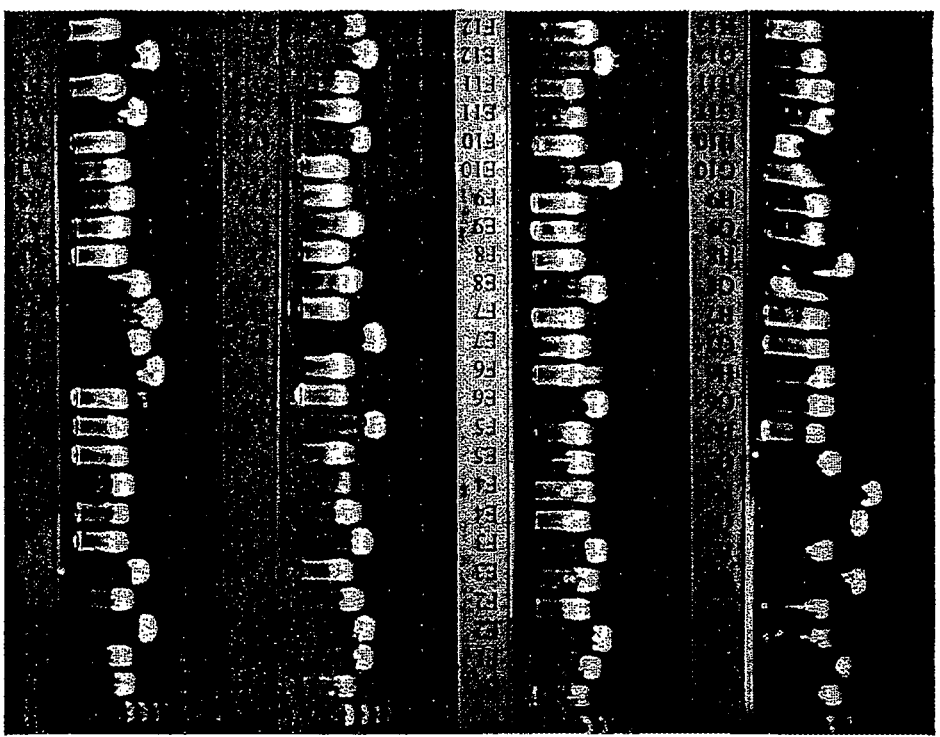
Fig. 12

COMPUTER SYSTEMS AND METHODS FOR GENOMIC ANALYSIS

CROSS-REFERENCE TO RELATED APPLICATIONS

The present application is a continuation of U.S. patent application Ser. No. 12/795,361, filed Jun. 7, 2010, now abandoned, which is a continuation of U.S. patent application Ser. No. 11/172,341, filed Jun. 29, 2005, now abandoned, which is a continuation of U.S. patent application Ser. No. 10/106,097, filed Mar. 26, 2002, now U.S. Pat. No. 6,969,589, issued on Nov. 29, 2005, which claims priority to U.S. provisional patent application Ser. No. 60/280,530, filed Mar. 30, 2001; U.S. provisional patent application Ser. No. 60/313,264, filed Aug. 17, 2001; U.S. provisional patent application Ser. No. 60/327,006, filed Oct. 5, 2001, all entitled "Identifying Human SNP Haplotypes, Informative SNPs and Uses Thereof; and U.S. provisional patent application Ser. No. 60/332,550, filed Nov. 26, 2001, entitled "Methods of Genomic Analysis"; the disclosures of all of which are specifically incorporated herein by reference in their entireties for all purposes.

BACKGROUND OF THE INVENTION

The DNA that makes up human chromosomes provides the instructions that direct the production of all proteins in the body. These proteins carry out the vital functions of life. Variations in the sequence of DNA encoding a protein produce variations or mutations in the proteins encoded, thus affecting the normal function of cells. Although environment often plays a significant role in disease, variations or mutations in the DNA of an individual are directly related to almost all human diseases, including infectious disease, cancer, and autoimmune disorders. Moreover, knowledge of genetics, particularly human genetics, has led to the realization that many diseases result from either complex interactions of several genes or their products or from any number of mutations within one gene. For example, Type I and II diabetes have been linked to multiple genes, each with its own pattern of mutations. In contrast, cystic fibrosis can be caused by any one of over 300 different mutations in a single gene.

Additionally, knowledge of human genetics has led to a limited understanding of variations between individuals when it comes to drug response—the field of pharmocogenetics. Over half a century ago, adverse drug responses were correlated with amino acid variations in two drug-metabolizing enzymes, plasma cholinesterase and glucose-6-phosphate dehydrogenase. Since then, careful genetic analyses have linked sequence polymorphisms (variations) in over 35 drug metabolism enzymes, 25 drug targets and 5 drug transporters with compromised levels of drug efficacy or safety (Evans and Relling, Science 296:487-91 (1999)). In the clinic, such information is being used to prevent drug toxicity; for example, patients are screened routinely for genetic differences in the thiopurine methyltransferase gene that cause decreased metabolism of 6-mercaptopurine or azathiopurine. Yet only a small percentage of observed drug toxicities have been explained adequately by the set of pharmacogenetic markers validated to date. Even more common than toxicity issues may be cases where drugs demonstrated to be safe and/or efficacious for some individuals have been found to have either insufficient therapeutic efficacy or unanticipated side effects in other individuals.

In addition to the importance of understanding the effects of variations in the genetic make up of humans, understanding the effects of variation in the genetic makeup of other non-human organisms—particularly pathogens—is important in understanding their effect on or interaction with humans. For example, the expression of virulence factors by pathogenic bacteria or viruses greatly affects the rate and severity of infection in humans that come into contact with such organisms. In addition, a detailed understanding of the genetic makeup of experimental animals, mice, rats, etc., is also of great value. For example, understanding the variations in the genetic makeup of animals used as model systems for evaluation of therapeutics is important for understanding the test results obtained using these systems and their predictive value for human use.

Because any two humans are 99.9% similar in their genetic makeup, most of the sequence of the DNA of their genomes is identical. However, there are variations in DNA sequence between individuals. For example, there are deletions of many-base stretches of DNA, insertion of stretches of DNA, variations in the number of repetitive DNA elements in, non-coding regions, and changes in single nitrogenous base positions in the genome called "single nucleotide polymorphisms" (SNPs). Human DNA sequence variation accounts for a large fraction of observed differences between individuals, including susceptibility to disease.

Although most SNPs are rare, it has been estimated that there are 5.3 million common SNPs, each with a frequency of 10-50%, that account for the bulk of the DNA sequence difference between humans. Such SNPs are present in the human genome once every 600 base pairs (Kruglyak and Nickerson, Nature Genet. 27:235 (2001)). Alleles (variants) making up blocks of such SNPs in close physical proximity are often correlated, resulting in reduced genetic variability and defining a limited number of "SNP haplotypes", each of which reflects descent from a single, ancient ancestral chromosome (Fullerton, et al., Am. J. Hum. Genet 67:881 (2000)).

The complexity of local haplotype structure in the human genome—and the distance over which individual haplotypes extend—is poorly defined. Empiric studies investigating different segments of the human genome in different populations have revealed tremendous variability in local haplotype structure. These studies indicate that the relative contributions of mutation, recombination, selection, population history, and stochastic events to haplotype structure vary in an unpredictable manner, resulting in some haplotypes that extend for only a few kilobases (kb), and others that extend for greater than 100 kb (A. G. Clark et al., Am. J. Hum. Genet. 63:595 (1998)).

These findings suggest that any comprehensive description of the haplotype structure of the human genome, defined by common SNPs, will require empirical analysis of a dense set of SNPs in many independent copies of the human genome. Such whole-genome analyses would provide a fine degree of genetic mapping and pinpoint specific regions of linkage. Until the present invention, however, the practice and cost of genotyping over 3,000,000 SNPs across each individual of a reasonably sized population has made this endeavor impractical. The present invention allows for, among a wide variety of applications, whole-genome association analysis of populations using SNP haplotypes.

SUMMARY OF THE INVENTION

The present invention relates to methods for identifying variations that occur in the human genome and relating these variations to the genetic bases of phenotype such as disease resistance, disease susceptibility or drug response. "Disease" includes but is not limited to any condition, trait or characteristic of an organism that it is desirable to change. For example, the condition may be physical, physiological or psychological and may be symptomatic or asymptomatic. The methods allow for identification of variants, identification of SNPs, determination of SNP haplotype blocks, determining SNP haplotype patterns, and further, identification of informative SNPs for each pattern, which affords genetic data compression.

Thus, one aspect of the present invention provides methods for selecting SNP haplotype patterns useful in data analysis. Such selection can be accomplished by isolating substantially identical (homologous) nucleic acid strands from a plurality of individuals; determining SNP locations in each nucleic acid strand; identifying the SNP locations in the nucleic acid strands that are linked, where the linked SNP locations form a SNP haplotype block; identifying isolate SNP haplotype blocks; identifying SNP haplotype patterns that occur in each SNP haplotype block; and selecting the identified SNP haplotype patterns that occur in at least two of the substantially identical nucleic acid strands. In one preferred embodiment, nucleic acid strands from at least about 10 different individuals or origins are used. In a more preferred embodiment, nucleic acid strands from at least 16 different origins are used. In an even more preferred embodiment, nucleic acid strands from at least 25 different origins are used, and in a yet more preferred embodiment, nucleic acid strands from at least 50 different origins are used. Further, a more preferred embodiment would determine SNP locations in at least about 100 nucleic acid strands from different origins. In addition, this method may further comprise selecting the SNP haplotype pattern that occurs most frequently in the substantially identical nucleic acid strands; selecting the SNP haplotype pattern that occurs next most frequently in the substantially identical nucleic acid strands; and repeating the selecting until the selected SNP haplotype patterns identify a portion of interest of the substantially identical nucleic acid strands. In a preferred embodiment, the portion of interest is between 70% and 99% of the substantially identical nucleic acid strands, and, in a more preferred embodiment, the portion of interest is about 80% of the substantially identical nucleic acid strands. Alternatively, one may wish to limit the selection of SNP haplotype patterns to no more than about three SNP haplotype patterns per SNP haplotype block.

In addition, the present invention provides a method for selecting a data set of SNP haplotype blocks for data analysis, comprising comparing SNP haplotype blocks for informativeness; selecting a first SNP haplotype block with high informativeness; adding the first SNP haplotype block to the data set; selecting a second SNP haplotype block with high informativeness; adding the second selected SNP haplotype block to the data set; and repeating the selecting and adding steps until the region of interest of a DNA strand is covered. In preferred embodiments, the SNP haplotype blocks selected are non-overlapping.

The present invention further provides methods for determining at least one informative SNP in a SNP haplotype pattern, comprising first determining SNP haplotype patterns for a SNP haplotype block, then comparing each SNP haplotype pattern of interest in the SNP haplotype block to the other SNP haplotype patterns of interest in the SNP haplotype block, and selecting at least one SNP in each SNP haplotype pattern that distinguishes this SNP haplotype pattern of interest from the other SNP haplotype patterns of interest in the SNP haplotype block. The selected SNP (or SNPs) is an informative SNP for the SNP haplotype pattern.

Also, the present invention allows for rapid scanning of genomic regions and provides a method for determining disease-related genetic loci or pharmacogenomic-related loci without a priori knowledge of the sequence or location of the disease-related genetic loci or pharmacogenomic-related loci. This can be done by determining SNP haplotype patterns from individuals in a control population, then determining SNP haplotype patterns from individuals in a experimental population, such as individuals in a diseased population or individuals that react in a particular manner when administered a drug. The frequencies of the SNP haplotype patterns of the control population are compared to the frequencies of the SNP haplotype patterns of the experimental population. Differences in these frequencies indicate locations of disease-related genetic loci or pharmacogenomic-related loci.

An additional aspect of the present invention provides a method of making associations between SNP haplotype patterns and a phenotypic trait of interest comprising: building baseline of SNP haplotype patterns of control individuals by the methods of the present invention; pooling whole genomic DNA from a clinical population having a common phenotypic trait of interest; and identifying the SNP haplotype patterns that are associated with the phenotypic trait of interest. Thus, the present invention allows for genome scanning to identify multiple haplotype blocks associated with a phenotype, which is particularly useful when studying polygenic traits.

Also, the present invention provides a method for identifying drug discovery targets comprising: associating SNP haplotype patterns with a disease; identifying a chromosomal location of the associated SNP haplotype patterns; determining the nature of the association of the chromosomal location and said disease; and using the gene or, gene product of the chromosomal location as a drug discovery target.

BRIEF DESCRIPTION OF THE FIGURES

The following figures and drawings form part of the present specification and are included to further demonstrate certain aspects of the patent invention. The invention may be better understood by reference to one or more of these drawings in combination with the detailed description of the specific embodiments presented herein.

FIG. 2 shows sample SNP haplotype blocks and SNP haplotype patterns according to the present invention.

FIG. 4 illustrates a simple employment of one embodiment of the method shown in FIG. 3.

FIG. 6 shows an example of how informative SNPs may be selected according to one embodiment of the present invention.

FIG. 11 is a table illustrating a portion of results obtained from screening hamster-human cell hybrids with the HuSNP genechip from Affymetrix, Inc.

FIG. 12 shows an example of various amplified genomic regions of human chromosome 22 and human chromosome 14 genomic DNA using long range PCR.

Figure 1:
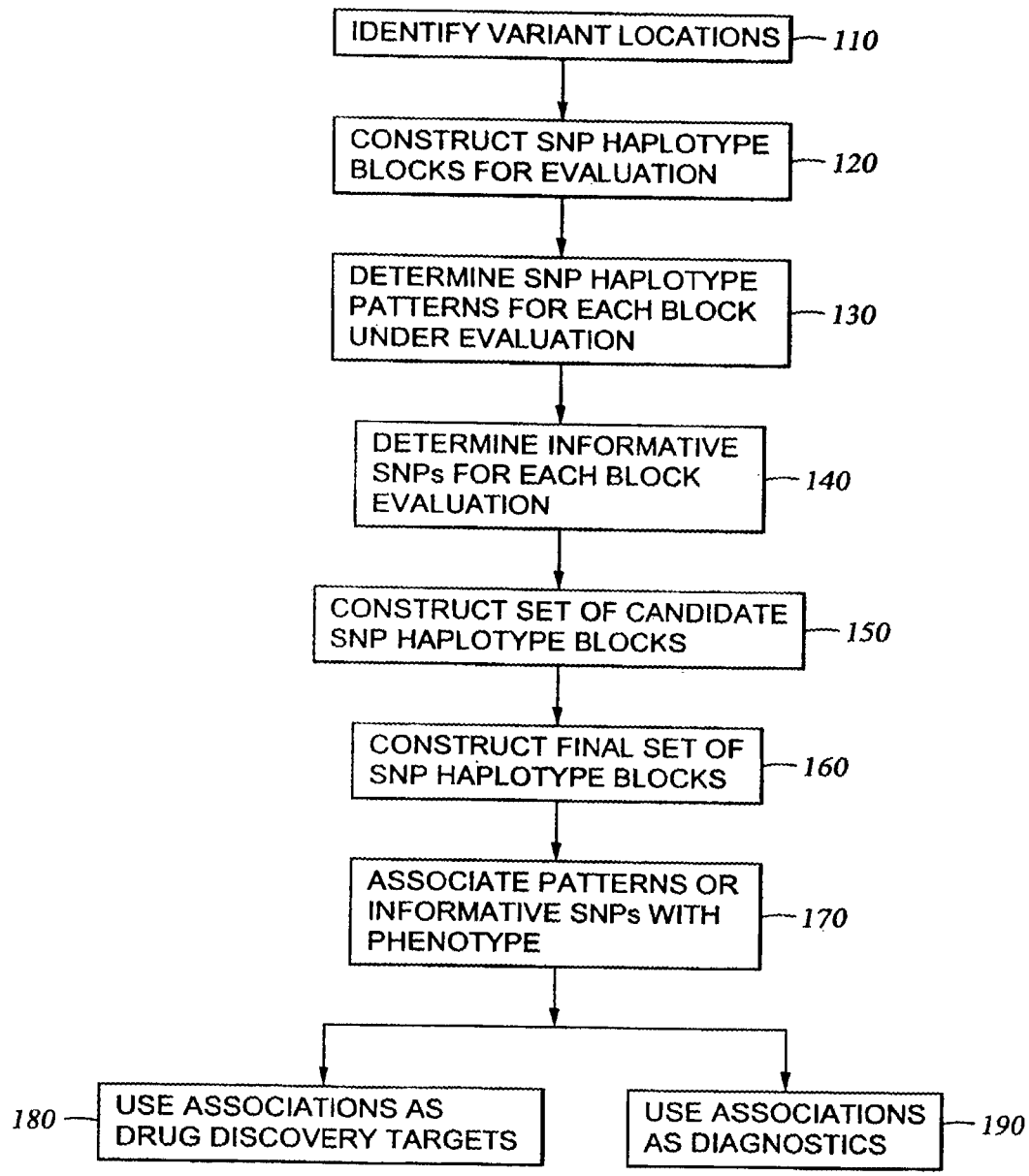
FIG. 1 is a schematic of one embodiment of the methods of the present invention from identifying variant locations to associating variants with phenotype, to using the associations to identify drug discovery targets or as diagnostic markers.

The present invention relates to methods for identifying variations that occur in the human genome and relating these variations to the genetic basis of disease and drug response. In particular, the present invention relates to identifying individual SNPs, determining SNP haplotype blocks and patterns, and, further, using the SNP haplotype blocks and patterns to dissect the genetic bases of disease and drug response. The methods of the present invention are useful in whole genome analysis.

DETAILED DESCRIPTION OF THE INVENTION

It readily should be apparent to one skilled in the art that various embodiments and modifications may be made to the invention disclosed in this application without departing from the scope and spirit of the invention. All publications mentioned herein are cited for the purpose of describing and disclosing reagents, methodologies and concepts that may be used in connection with the present invention. Nothing herein is to be construed as an admission that these references are prior art in relation to the inventions described herein.

As used in the specification, "a" or "an" means one or more. As used in the claim(s), when used in conjunction with the word "comprising", the words "a" or "an" mean one or more. As used herein, "another" means at least a second or more.

As used herein, when the term "different origins" is used, it refers to the fact DNA strands from different organisms come from a different origin. Further, each DNA strand in a single organism's genome come from different origins. In a diploid organism, an individual organism's genome is made up of a set of pairs of substantially identical DNA strands. That is, a single individual would have substantially identical DNA strands from two different origins—one DNA strand of the pair is of maternal origin and one DNA strand of the pair is of paternal origin. Two or more nucleic acid sequences—for example, two or more DNA strands—are considered to be substantially identical if they exhibit at least about 70% sequence identity at the nucleotide level, preferably about 75%, more preferably about 80%, still more preferably about 85%, yet more preferably about 90%, even more preferably about 95% and even more preferably nucleic acid sequences are considered to be substantially identical if they exhibit at least about 98% sequence identity at the nucleotide level. The extent of sequence identity that is relevant between two or more nucleic acid sequences will depend on the host source of the nucleic acids. For example, a greater than 95% sequence identity may be relevant when looking at same species comparisons, whereas a sequence identity of 70% or even less may be relevant when making cross species comparisons. Of course, when one refers to DNA herein such reference may include derivatives of DNA such as amplicons, RNA transcripts, nucleic acid mimetics, etc.

As used herein, "individual" refers to a specific single organism, such as a single animal, human insect, bacterium, etc.

As used herein, "informativeness" of a SNP haplotype block is defined as the degree to which a SNP haplotype block provides information about genetic regions.

As used herein, the term "informative SNP" refers to a genetic variant such as a SNP or subset (more than one) of SNPs that tends to distinguish one SNP haplotype pattern from other SNP haplotype patterns within a SNP haplotype block.

As used herein, the term "isolate SNP block" refers to a SNP haplotype block that consists of one SNP.

As used herein, the term "linkage disequilibrium", "linked" or "LD" refers to genetic loci that tend to be transmitted from generation to generation together, e.g., genetic loci that are inherited non-randomly.

As used herein, the term "singleton SNP haplotype" or "singleton SNP" refers to a specific SNP allele or variant that occurs in less than a certain portion of the population.

As used herein, the term "SNP" or "single nucleotide polymorphism" refers to a genetic variation between individuals; e.g., a single nitrogenous base position in the DNA of organisms that is variable. As used herein, "SNPs" is the plural of SNP. Of course, when one refers to DNA herein such reference may include derivatives of DNA such as amplicons, RNA transcripts, etc.

As used herein, the term "SNP haplotype block" means a group of variant or SNP locations that do not appear recombine independently and that can be grouped together in blocks of variants or SNPs.

As used herein, the term "SNP haplotype pattern" refers to the set of genotypes for SNPs in a SNP haplotype block in a single DNA strand.

As used herein, the term "SNP location" is the site in a DNA sequence where a SNP occurs.

As used herein a "SNP haplotype sequence" is a DNA sequence in a DNA strand that contains at least one SNP location.

Preparation of Nucleic Acids for Analysis

Nucleic acid molecules may be prepared for analysis using any technique known to those skilled in the art. Preferably such techniques result in the production of a nucleic acid molecule sufficiently pure to determine the presence or absence of one or more variations at one or more locations in the nucleic acid molecule. Such techniques may be found, for example, in Sambrook, et al., *Molecular Cloning: A Laboratory Manual* (Cold Spring Harbor Laboratory, New York) (1989), and Ausubel, et al., *Current*

*Protocols in Molecular Biology* (John Wiley and Sons, New York) (1997), incorporated herein by reference.

When the nucleic acid of interest is present in a cell, it may be necessary to first prepare an extract of the cell and then perform further steps—i.e., differential precipitation, column chromatography, extraction with organic solvents and the like—in order to obtain a sufficiently pure preparation of nucleic acid. Extracts may be prepared using standard techniques in the art, for example, by chemical or mechanical lysis of the cell. Extracts then may be further treated, for example, by filtration and/or centrifugation and/or with chaotropic salts such as guanidinium isothiocyanate or urea or with organic solvents such as phenol and/or $HCCl_3$ to denature any contaminating and potentially interfering proteins. When chaotropic salts are used, it may be desirable to remove the salts from the nucleic acid-containing sample. This can be accomplished using standard techniques in the art such as precipitation, filtration, size exclusion chromatography and the like.

In some instances, it may be desirable to extract and separate messenger RNA from cells. Techniques and material for this purpose are known to those skilled in the art and may involve the use of oligo dT attached to a solid support such as a bead or plastic surface. Suitable conditions and materials are known to those skilled in the art and may be found in the Sambrook and Ausubel references cited above. It may be desirable to reverse transcribe the mRNA into cDNA using, for example, a reverse transcriptase enzyme. Suitable enzymes are commercially available from, for example, Invitrogen, Carlsbad Calif. Optionally, cDNA prepared from mRNA may then be amplified.

One approach particularly suitable for examining haplotype patterns and blocks is using somatic cell genetics to separate chromosomes from a diploid state to a haploid state. In one embodiment, a human lymphoblastoid cell line that is diploid may be fused to a hamster fibroblast cell line that is also diploid such that the human chromosomes are introduced into the hamster cells to produce cell hybrids. The resulting cell hybrids are examined to determine which human chromosomes were transferred, and which, if any, of the transferred human chromosomes are in a haploid state (see, e.g., Patterson, et al., *Annal. N.Y. Acad. Of Sciences*, 396:69-81 (1982)).

Figure 10:
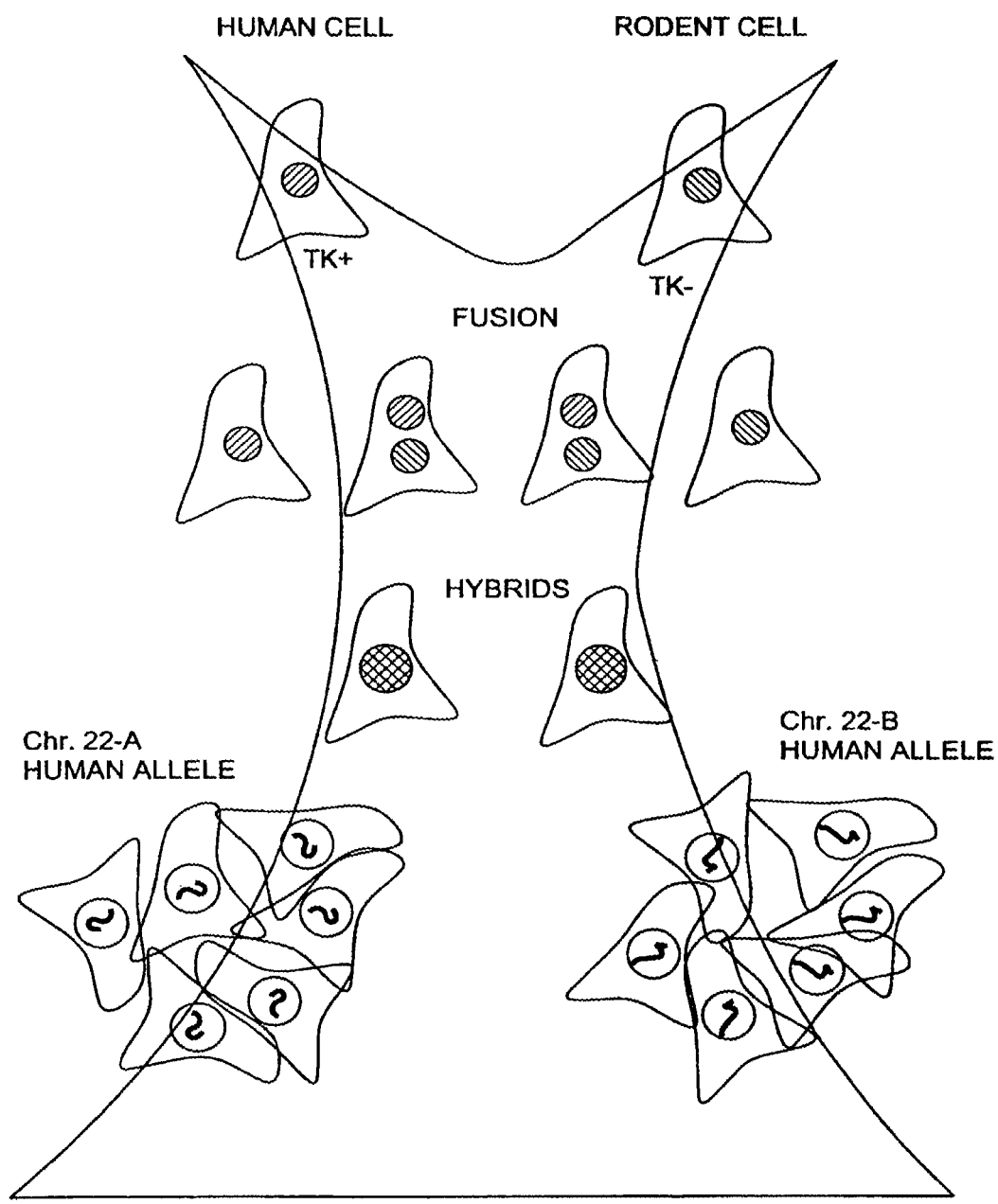
FIG. 10 is a schematic of the construction of somatic cell hybrids.

A schematic of the procedure is shown in FIG. 10. FIG. 10 shows a diploid human lymphoblastoid cell line that is wildtype for the thymidine kinase gene being fused to a diploid hamster fibroblast cell line containing a mutation in the thymidine kinase gene. In a sub-population of the resulting cells, human chromosomes are present in hybrids. Selection for the human DNA-containing hybrid cells is achieved by utilizing HAT medium (selective medium). Only hybrid cells that have a stably-incorporated human DNA strand having the wildtype human thymidine kinase gene grow in cell culture medium containing HAT. Of the resulting hybrids, some hybrids may contain both copies of some human chromosomes, only one copy of a human chromosome or no copies of a particular human chromosome. For example, for a human chromosome 22 having a locus with either an A or a B allele, the resulting hybrid cells may contain one human chromosome 22 variant (e.g., the "A" variant) or a portion thereof, some may contain the other human chromosome 22 variant (the "B" variant) or a portion thereof, some may contain both human chromosome 22 variants or portions thereof, and some hybrids may not contain any portion of a human chromosome 22 at all. In FIG. 10, only two of the resulting hybrid populations are shown. Once the appropriate hybrids are selected, the nucleic acids from these hybrids may be isolated by, for example, the techniques described above and then subjected to SNP discovery, and haplotype block and pattern analyses of the present invention.

Amplification Techniques

It may be desirable to amplify one or more nucleic acids of interest before determining the presence or absence of one or more variations in the nucleic acid. Nucleic acid amplification increases the number of copies of the nucleic acid sequence of interest. Any amplification technique known to those of skill in the art may be used in conjunction with the present invention including, but not limited to, polymerase chain reaction (PCR) techniques. PCR may be carried out using materials and methods known to those of skill in the art.

PCR amplification generally involves the use of one strand of a nucleic acid sequence as a template for producing a large number of complements to that sequence. The template may be hybridized to a primer having a sequence complementary to a portion of the template sequence and contacted with a suitable reaction mixture including dNTPs and a polymerase enzyme. The primer is elongated by the polymerase enzyme producing a nucleic acid complementary to the original template.

For the amplification of both strands of a double stranded nucleic acid molecule, two primers may be used, each of which may have a sequence which is complementary to a portion of one of the nucleic acid strands. Elongation of the primers with a polymerase enzyme results in the production of two double-stranded nucleic acid molecules each of which contains a template strand and a newly synthesized complementary strand. The sequences of the primers typically are chosen such that extension of each of the primers results in elongation toward the site in the nucleic acid molecule where the other primer hybridizes.

The strands of the nucleic acid molecules are denatured—for example, by heating—and the process is repeated, this time with the newly synthesized strands of the preceding step serving as templates in the subsequent steps. A PCR amplification protocol may involve a few to many cycles of denaturation, hybridization and elongation reactions to produce sufficient amounts of the desired nucleic acid.

Although PCR methods typically employ heat to achieve strand denaturation and allow subsequent hybridization of the primers, any other means that results in making the nucleic acids available for hybridization to the primers may be used. Such techniques include, but are not limited to, physical, chemical, or enzymatic means, for example, by inclusion of a helicase, (see Radding, *Ann. Rev. Genetics* 16: 405-436 (1982)) or by electrochemical means (see PCT Application Nos. WO 92/04470 and WO 95/25177).

Template-dependent extension of primers in PCR is catalyzed by a polymerase enzyme in the presence of at least 4 deoxyribonucleotide triphosphates (typically selected from dATP, dGTP, dCTP, dUTP and dTTP) in a reaction medium which comprises the appropriate salts, metal cations, and pH buffering system. Suitable polymerase enzymes are known to those of skill in the art and may be cloned or isolated from natural sources and may be native or mutated forms of the enzymes. So long as the enzymes retain the ability to extend the primers, they may be used in the amplification reactions of the present invention.

The nucleic acids used in the methods of the invention may be labeled to facilitate detection in subsequent steps. Labeling may be carried out during an amplification reaction by incorporating one or more labeled nucleotide triphosphates and/or one or more labeled primers into the amplified sequence. The nucleic acids may be labeled following amplification, for example, by covalent attachment of one or more detectable groups. Any detectable group known to those skilled in the art may be used, for example, fluorescent groups, ligands and/or radioactive groups. An example of a suitable labeling technique is to incorporate nucleotides containing labels into the nucleic acid of interest using a terminal deoxynucleotidyl transferase (TdT) enzyme. For example, a nucleotide—preferably a dideoxy nucleotide—containing a label is incubated with the nucleic acid to be labeled and a sufficient amount of TdT to incorporate the nucleotide. A preferred nucleotide is a dideoxynucleotide—i.e., ddATP, ddGTP, ddCTP, ddTTP, etc—having a biotin label attached.

Techniques to optimize the amplification of long sequences may be used. Such techniques work well on genomic sequences. The methods disclosed in pending US patent applications U.S. Ser. No. 60/317,311, filed Sep. 5, 2001; U.S. Ser. No. 10/042,406, filed Jan. 9, 2002 and issued as U.S. Pat. No. 6,898,531, entitled "Algorithms for Selection of Primer Pairs"; and U.S. Ser. No. 10/042,492, filed Jan. 9, 2002 and issued as U.S. Pat. No. 6,740,510, entitled "Methods for Amplification of Nucleic Acids" are particularly suitable for amplifying genomic DNA for use in the methods of the present invention.

Amplified sequences may be subjected to other post amplification treatments either before or after labeling. For example, in some cases, it may be desirable to fragment the amplified sequence prior to hybridization with an oligonucleotide array. Fragmentation of the nucleic acids generally may be carried out by physical, chemical or enzymatic methods that are known in the art. Suitable techniques include, but are not limited to, subjecting the amplified nucleic acids to shear forces by forcing the nucleic acid containing fluid sample through a narrow aperture or digesting the PCR product with a nuclease enzyme. One example of a suitable nuclease enzyme is Dnase I. After amplification, the PCR product may be incubated in the presence of a nuclease for a period of time designed to produce appropriately sized fragments. The sizes of the fragments may be varied as desired, for example, by increasing the amount of nuclease or duration of incubation to produce smaller fragments or by decreasing the amount of nuclease or period of incubation to produce larger fragments. Adjusting the digestion conditions to produce fragments of the desired size is within the capabilities of a person of ordinary skill in the art. The fragments thus produced may be labeled as described above.

Methods for the Detection of SNPs (SNP Discovery)

Determination of the presence or absence of one or more variations in a nucleic acid may be made using any technique known to those of skill in the art. Any technique that permits the accurate determination of a variation can be used. Preferred techniques will permit rapid, accurate determination of multiple variations with a minimum of sample handling required. Some examples of suitable techniques are provided below.

Several methods for DNA sequencing are well known and generally available in the art and may be used to determine the location of SNPs in a genome. See, for example, Sambrook, et al., *Molecular Cloning: A Laboratory Manual* (Cold Spring Harbor Laboratory, New York) (1989), and Ausubel, et al., *Current Protocols in Molecular Biology* (John Wiley and Sons, New York) (1997), incorporated herein by reference. Such methods may be used to determine the sequence of the same genomic regions from different DNA strands where the sequences are then compared and the differences (variations between the strands) are noted. DNA sequencing methods may employ such enzymes as the Klenow fragment of DNA polymerase I, Sequenase (US Biochemical Corp, Cleveland, Ohio.), Taq polymerase (Perkin Elmer), thermostable T7 polymerase (Amersham, Chicago, Ill.), or combinations of polymerases and proofreading exonucleases such as those found in the Elongase Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer, Wellesley, Mass.).

In addition, capillary electrophoresis systems which are commercially available may be used to perform variation or SNP analysis. In particular, capillary sequencing may employ flowable polymers for electrophoretic separation, four different fluorescent dye (one for each nucleotide) which are laser activated, and detection of the emitted wavelengths by a charge coupled device camera. Output/light intensity may be converted to electrical signal using appropriate software (e.g. Genotyper and Sequence Naviagator, Perkin Elmer, Wellesley, Mass.) and the entire process from loading of samples to computer analysis and electronic data display may be computer controlled. Again, this method may be used to determine the sequence of the same genomic regions from different DNA strands where the sequences are then compared and the differences (variations between the strands) are noted.

Optionally, once a genomic sequence from one reference DNA strand has been determined by sequencing, it is possible to use hybridization techniques to determine variations in sequence between the reference strand and other DNA strands. These variations may be SNPs. An example of a suitable hybridization technique involves the use of DNA chips (oligonucleotide arrays), for example, those available from Affymetrix, Inc. Santa Clara, Calif. For details on the use of DNA chips for the detection of, for example, SNPs, see U.S. Pat. No. 6,300,063 issued to Lipshultz, et al., and U.S. Pat. No. 5,837,832 to Chee, et al., HuSNP Mapping Assay, reagent kit and user manual, Affymetrix Part No. 90094 (Affymetrix, Santa Clara, Calif.), all incorporated by reference herein.

In preferred embodiments, more than 10,000 bases of a reference sequence and the other DNA strands are scanned for variants. In more preferred embodiments, more than $1 \times 10^6$ bases of a reference sequence and the other DNA strands are scanned for variants, even more preferably more than $2 \times 10^6$ bases of a reference sequence and the other DNA strands are scanned, even more preferably $1 \times 10^7$ bases are scanned, and more preferably more than $1 \times 10^8$ bases are scanned, and more preferably more than $1 \times 10^9$ bases of a reference sequence and the other DNA strands are scanned for variants. In preferred embodiments at least exons are scanned for variants, and in more preferred embodiments both introns and exons are scanned for variants. In an even more preferred embodiment, introns, exons and intergenic sequences are scanned for variants. In preferred embodiments the scanned nucleic acids are genomic DNA, including both coding and noncoding regions. In most preferred embodiments, such DNA is from a mammalian organism such as a human. In preferred embodiments, more than 10% of the genomic DNA from the organism is scanned, in more preferred embodiments more than 25% of the genomic DNA from the organism is scanned, in more preferred embodiments, more than 50% of the genomic DNA from the organism is scanned, and in most preferred embodiments, more than 75% of the genomic DNA is scanned. In some embodiments of the present invention, known repetitive regions of the genome are not scanned, and do not count toward the percentage of genomic DNA scanned. Such known repetitive regions may include Single Interspersed Nuclear Elements (SINEs, such as alu and MIR sequences), Long Interspersed Nuclear Elements (LINEs, such as LINE1 and LINE2 sequences), Long Terminal Repeats (LTRs such as MaLRs, Retrov and MER4 sequences), transposons, and MER1 And MER2 sequences.

Briefly, in one embodiment, labeled nucleic acids in a suitable solution are denatured—for example, by heating to 95° C.—and the solution containing the denatured nucleic acids is incubated with a DNA chip. After incubation, the solution is removed, the chip may be washed with a suitable washing solution to remove un-hybridized nucleic acids, and the presence of hybridized nucleic acids on the chip is detected. The stringency of the wash conditions may be adjusted as necessary to produce a stable signal. Detecting the hybridized nucleic acids may be done directly, for example, if the nucleic acids contain a fluorescent reporter group, fluorescence may be directly detected. If the label on the nucleic acids is not directly detectable, for example, biotin, then a solution containing a detectable label, for example, streptavidin coupled to phycoerythrin, may be added prior to detection. Other reagents designed to enhance the signal level may also be added prior to detection, for example, a biotinylated antibody specific for streptavidin may be used in conjunction with the biotin, streptavidin-phycoerythrin detection system. In some embodiments, the oligonucleotide arrays, used in the methods of the present invention contain at least $1 \times 10^6$ probes per array. In a preferred embodiment, the oligonucleotide arrays used in the methods of the present invention contain at least $10 \times 10^6$ probes per array. In a more preferred embodiment, the oligonucleotide arrays used in the methods of the present invention contain at least $50 \times 10^6$ probes per array.

Once variant locations have been determined (SNP discovery) by using, for example, sequencing or microarray analysis, it is necessary to genotype the SNPs of control and sample populations. The hybridization methods just described work well for this purpose, providing an accurate and rapid technique for detecting and genotyping SNPs in multiple samples. In addition, a technique suitable for the detection of SNPs in genomic DNA—without amplification—is the Invader technology available from Third Wave Technologies, Inc., Madison, Wis. Use of this technology to detect SNPs may be found, e.g., in Hessner, et al., *Clinical Chemistry* 46(8):1051-56 (2000); Hall, et al., *PNAS* 97(15): 8272-77 (2000); Agarwal, et al., *Diag. Molec. Path.* 9(3): 158-64 (2000); and Cooksey, et al., *Antimicrobial and Chemotherapy* 44(5):1296-1301 (2000). In the Invader process, two short DNA probes hybridize to a target nucleic acid to form a structure recognized by a nuclease enzyme. For SNP analysis, two separate reactions are run—one for each SNP variant. If one of the probes is complementary to the sequence, the nuclease will cleave it to release a short DNA fragment termed a "flap". The flap binds to a fluorescently-labeled probe and forms another structure recognized by a nuclease enzyme. When the enzyme cleaves the labeled probe, the probe emits a detectable fluorescence signal thereby indicating which SNP variant is present.

An alternative to Invader technology, rolling circle amplification utilizes an oligonucleotide complementary to a circular DNA template to produce an amplified signal (see, for example, Lizardi, et al., *Nature Genetics* 19(3):225-32 (1998); and Zhong, et al., *PNAS* 98(7):3940-45 (2001)). Extension of the oligonucleotide results in the production of multiple copies of the circular template in a long concatemer. Typically, detectable labels are incorporated into the extended oligonucleotide during the extension reaction. The extension reaction can be allowed to proceed until a detectable amount of extension product is synthesized.

In order to detect SNPs using rolling circle amplification, three probes and two circular DNA templates may be used. The first probe—the target specific probe—may be constructed to be complementary to a target nucleic acid molecule such that the 5'-terminus of the probe hybridizes to the nucleotide immediately adjacent 5' to the SNP site in the target nucleic acid. The site of the SNP is not base paired to the first probe.

The other two probes—rolling circle probes—are constructed to have two 3'-terminals. This can be accomplished in various ways, for example, by introducing a 5'-5' linkage in the central portion of the probes resulting in a reversal of polarity of the nucleotide sequence at that point. One end of each of the probes has a sequence that is complementary to a portion of a different circular template molecule while the other end is complementary to a portion of the target nucleic acid sequence. The target-sequence-complementary terminal is constructed such that the 3'-most nucleotide aligns with the nucleotide at the SNP site. One of the probes may contain a nucleotide complementary to the nucleotide at the SNP site in the target nucleic acid while the other contains a nucleotide that is not complementary. In the instance where two or more variants of the SNP are present in the population, probes may be constructed to have 3'-nucleotides complementary to the variants to be detected.

The probes—both target specific and rolling circle—may be hybridized to the target sequence and contacted with a ligase enzyme. When the 3'-most nucleotide of the rolling circle probe forms a base pair with the nucleotide at the SNP site, the two probes—the target specific and the rolling circle—are efficiently ligated together. When the 3'-most nucleotide of the rolling circle probe is not capable of base pairing with the nucleotide at the SNP site in the target, the probes are not ligated. The unligated probe is washed away and the sample is contacted with the template circles, polymerase and labeled nucleoside triphosphates.

Another technique suitable for the detection of SNPs makes use of the 5'-exonuclease activity of a DNA polymerase to generate a signal by digesting a probe molecule to release a fluorescently labeled nucleotide. This assay is, frequently referred to as a Taqman assay (see, e.g., Arnold, et al. *BioTechniques* 25(1):98-106 (1998); and Becker, et al., *Hum. Gene Ther.* 10:2559-66 (1999)). A target DNA containing a SNP is amplified in the presence of a probe molecule that hybridizes to the SNP site. The probe molecule contains both a fluorescent reporter-labeled nucleotide at the 5'-end and a quencher-labeled nucleotide at the 3'-end. The probe sequence is selected so that the nucleotide in the probe that aligns with the SNP site in the target DNA is as near as possible to the center of the probe to maximize the difference in melting temperature between the correct match probe and the mismatch probe. As the PCR reaction is conducted, the correct match probe hybridizes to the SNP site in the target DNA and is digested by the Taq polymerase used in the PCR assay. This digestion results in physically separating the fluorescent labeled nucleotide from the quencher with a concomitant increase in fluorescence. The mismatch probe does not remain hybridized during the elongation portion of the PCR reaction and is, therefore, not digested and the fluorescently labeled nucleotide remains quenched.

Denaturing HPLC using a polystyrene-divinylbenzene reverse phase column and an ion-pairing mobile phase can be used to identify SNPs. A DNA segment containing a SNP is PCR amplified. After amplification, the PCR product is denatured by heating and mixed with a second denatured PCR product with a known nucleotide at the SNP position. The PCR products are annealed and are analyzed by HPLC at elevated temperature. The temperature is chosen to denature duplex molecules that are mismatched at the SNP location but not to denature those that are perfect matches. Under these conditions, heteroduplex molecules typically elute before homoduplex molecules. For an example of the use of this technique see Kota, et al., *Genome* 44(4):523-28 (2001).

SNPs can be detected using solid phase amplification and microsequencing of the amplification product. Beads to which primers have been covalently attached are used to carry out amplification reactions. The primers are designed to include a recognition site for a Type II restriction enzyme. After amplification—which results in a PCR product attached to the bead—the product is digested with the restriction enzyme. Cleavage of the product with the restriction enzyme results in the production of a single stranded portion including the SNP site and a 3'-OH that can be extended to fill in the single stranded portion. Inclusion of ddNTPs in an extension reaction allows direct sequencing of the product. For an example of the use of this technique to identify SNPs see Shapero, et al., *Genome Research* 11(11): 1926-34 (2001).

Data Analysis

FIG. 1 is a schematic showing the steps of one embodiment of the methods of the present invention. Once SNPs (variants) have been located or discovered by, e.g., the methods described supra (step 110 of FIG. 1), SNP haplotype blocks, SNP haplotype patterns within each SNP haplotype block, and informative SNPs for the SNP haplotype patterns may be determined. One may use all SNPs or variants located; alternatively, one may focus the analysis on only a portion of the SNPs located. For example, the set of SNPs analyzed may exclude transition SNPs of the form Cg↔Tg or cG↔cA. In addition, in one embodiment of the present invention, the focus is on common SNPs. Common SNPs are those SNPs whose less common form is present at a minimum frequency in a given population. For example, common SNPs are those SNPs that are found in at least about 2% to 25% of the population. In a preferred embodiment, common SNPs are those SNPs that are found in at least about 5% to 15% of the population. In a more preferred embodiment, common SNPs are those that are found in at least about 10% of the population. Common SNPs likely result from mutations that occurred early in the evolution of humans. Focusing on common SNPs minimizes systematic allele or variant differences between control and experimental populations that appear as disease or drug-response associated, yet result only from migratory history or mating practices; i.e., focusing on common SNPs decreases the false positives that result from recent population anomalies. Moreover, common SNPs are relevant to a larger proportion of the human population, making the present invention more broadly applicable to disease and drug response studies. Along the same line, SNPs in which an variant is observed only once may be eliminated from analysis in some embodiments of the present invention (for example, singleton SNPs). However, certain analyses may be performed including some or all of these singleton SNPs, particularly when looking at specific sub-populations or populations that have been influenced by migratory practices and the like.

In step 120 of FIG. 1, the variants or SNPs of interest are assigned to haplotype blocks for evaluation. Variants or SNPs from a whole genome or chromosome may be analyzed and assigned to SNP haplotype blocks. Alternatively, variants from only a focused genomic region specific to some disease or drug response mechanism may be assigned to the SNP haplotype blocks.

FIG. 2 provides one illustration of showing how variants, usually SNPs, occur in haplotype blocks in a genome, and that more than one haplotype pattern can occur within each haplotype block. If SNP haplotype patterns were completely random, it would be expected that the number of possible SNP haplotype patterns observed for a SNP haplotype block of N SNPs would be $2^N$. However, it was observed in performing the methods of the present invention that the number of SNP haplotype patterns in each SNP haplotype block is smaller than $2^N$ because the SNPs are linked (not $4^N$, as the variants will most commonly be biallelic, i.e., occur in only one of two forms, not all four nucleotide base possibilities). Certain SNP haplotype patterns were observed at a much higher frequency than would be expected in a non-linkage case. Thus, SNP haplotype blocks are chromosomal regions that tend to be inherited as a unit, with a relatively small number of common patterns. Each line in FIG. 2 represents portions of the haploid genome sequence of different individuals. As shown therein, individual W has an "A" at position 241, a "G" at position 242, and an "A" at position 243. Individual X has the same bases at positions 241, 242, and 243. Conversely, individual Y has a T at positions 241 and 243, but an A at position 242. Individual Z has the same bases as individual Y at positions 241, 242, and 243. Variants in block 261 will tend to occur together. Similarly, the variants in block 262 will tend to occur together, as will those variants in block 263. Of course, only a few bases in a genome are shown in FIG. 2. In fact, most bases will be like those at position 245 and 248, and will not vary from individual to individual.

The assignment of SNPs to SNP haplotype blocks, step 120 of FIG. 1, is, in one case, an iterative process involving the construction of SNP haplotype blocks from the SNP locations along a genomic region of interest. In one embodiment, once the initial SNP haplotype blocks are constructed, SNP haplotype patterns present in the constructed SNP haplotype blocks are determined (step 130 of FIG. 1). In some specific embodiments, the number of SNP haplotype patterns selected per SNP haplotype block in step 130 is no greater than about five. In another specific embodiment, the number of SNP haplotype patterns selected per SNP haplotype block is equal to the number of SNP haplotype patterns necessary to identify SNP haplotype patterns in greater than 50% of the DNA strands being analyzed. In other words, enough SNP haplotype patterns are selected, for example, four patterns per block are selected, such that at least half of the DNA strands, analyzed will have a SNP haplotype pattern that matches one of the four patterns selected in each SNP haplotype block. In a preferred embodiment, the number of SNP haplotype patterns selected per SNP haplotype block is equal to the number of SNP haplotype patterns necessary to identify SNP haplotype patterns in greater than 70% of the DNA strands being analyzed. In one preferred embodiment, the number of SNP haplotype patterns selected per SNP haplotype block is equal to the number of SNP haplotype patterns necessary to identify SNP haplotype patterns in greater than 80% of the DNA strands being analyzed. In addition, in some embodiments of the present invention, SNP haplotype patterns that occur in less than a certain portion of DNA strands being analyzed are eliminated from analysis. For example, in one embodiment, if ten DNA strands are being analyzed, SNP haplotype patterns that are found to occur in only one sample out of ten are eliminated from analysis.

Once the SNP haplotype patterns of interest are selected, informative SNPs for these SNP haplotype patterns are determined (step 140 of FIG. 1). From this initial set of blocks, a set of candidate SNP blocks that fit certain criteria for informativeness is constructed (step 150 of FIG. 1). FIGS. 4 and 5 illustrate steps 120, 130, 140 and 150 in more detail.

Figure 3:
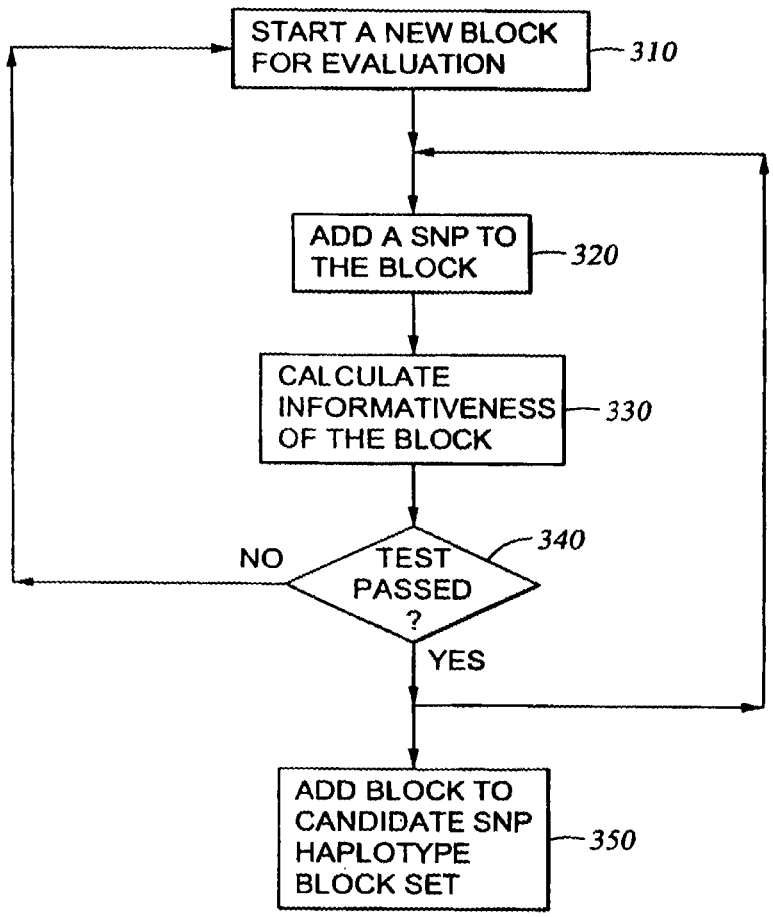
FIG. 3 is a schematic showing one embodiment of a method for selecting SNP haplotype blocks.

In FIG. 3, step 310 provides that a new block of SNPs is chosen for evaluation. In one embodiment, the first block chosen contains only the first SNP in a SNP haplotype sequence; thus at step 320, the first, single, SNP is added to the block. At step 330, informativeness of this block is determined.

"Informativeness" of a SNP haplotype block is defined in one embodiment as the degree to which the block, provides information about genetic regions. For example, in one embodiment of the present invention, informativeness could be calculated as the ratio of the number of SNP locations in a SNP haplotype block divided by the number of SNPs required to distinguish each SNP haplotype pattern under consideration from other SNP haplotype patterns under consideration (number of informative SNPs) in that block. Another measure of informativeness might be the number of informative SNPs in the block. One skilled in the art recognizes that informativeness may be determined in any number of ways.

Referring again to FIG. 2, SNP haplotype block 261 contains three SNPs and two SNP haplotype patterns (AGA and TAT). Any one of the three SNPs present can be used to tell the patterns apart; thus, any one of these SNPs can be chosen to be the informative SNP for this SNP haplotype pattern. For example, if it is determined that a sample nucleic acid contains a T at the first position, the same sample will contain an A at the second position and a T at the third position. If it is determined in a second sample that the SNP in the second position is a G, the first and third SNPs will be A's. Thus, by one measure of informativeness, the informativeness value for this first block is 3: 3 total SNPs divided by 1 informative SNP needed to distinguish the patterns from each other. Similarly, SNP haplotype block 262 contains three SNPs (two positions do not have variants) and two haplotype patterns (TCG and CAC). As with the previously-analyzed block, any one of the three SNPs can be evaluated to tell one pattern from the other; thus, the informativeness of this block is 3: 3 total SNPs divided by 1 informative SNP needed to distinguish the patterns. SNP haplotype block 263 contains five SNPs and two SNP patterns (TAACG and ATCAC). Again, any one of the five SNPs can be used to tell one pattern from the other; thus, the informativeness of this block is 5: 5 total SNPs divided by 1 informative SNP needed to distinguish the patterns.

FIG. 2 provides a simple example of genetic analysis. When several SNP haplotype patterns are present in a block, it may be necessary to use more than one SNP as informative SNPs. For example, in a case where a block contains, for example, six SNPs and two SNPs are needed to distinguish the patterns of interest, the informativeness of the block is 3: 6 total SNPs divided by 2 SNPs needed to distinguish the patterns. Generally speaking, as many as $2^N$ distinct SNP haplotype patterns can be distinguished by using the genotypes of N suitably selected SNPs. Therefore, if there exist only two SNP haplotype patterns in the SNP haplotype block, a single SNP should be able to differentiate between the two. If there are three or four patterns, at least two SNPs would likely be required, etc.

In step 340 of FIG. 3, once the informativeness of a SNP haplotype block is determined, a test is performed. The test essentially evaluates the SNP haplotype blocks based on selected criteria (for example, whether a block meets a threshold measure of informativeness), and the result of the test determines whether, for example, another SNP will be added to the block for analysis or whether the analysis will proceed with a new block starting at a different SNP location. FIG. 4 illustrates one embodiment of this process.

In FIG. 4, assume there is a DNA sequence with six SNP locations. The analysis of SNP haplotype blocks described above might be performed in the following manner: SNP haplotype block A is selected containing only the SNP at SNP position 1 (steps 310 and 320 of FIG. 3). The informativeness of this block is calculated (step 330), and it is determined whether the informativeness of this block meets a threshold measure of informativeness (step 340). In this case, it "passes" and two things happen. First, this block of one SNP (SNP position 1) is added to the set of candidate SNP haplotype blocks (step 350). Second, another SNP (here, SNP position 2) is added to this block (step 320) to create a new block, B, containing SNP positions 1 and 2, which is then analyzed. In this illustration block B also meets the threshold measure of informativeness (step 340), so it would be added to the set of candidate SNP haplotype blocks (step 350), and another SNP (here, SNP position 3) is added to this block (step 320) to create new block C, containing SNP positions 1, 2 and 3, which is then analyzed. In this illustration, C also meets the threshold measure of informativeness and it is added to the set of candidate SNP haplotype blocks (step 350), and another SNP (here, SNP position 4) is added to this block (step 320) to create new block D, containing SNP positions 1, 2, 3, and 4, which is then analyzed. In the FIG. 4 illustration, SNP block D does not meet the threshold measure of informativeness. SNP block D is not added to the set of candidate SNP haplotype blocks (step 350), nor does another. SNP get added to block D for analysis. Instead, a new SNP location is selected for a round of SNP block evaluations.

In FIG. 4, after block D fails to meet the threshold measure of informativeness, a new block, E, is selected that contains only the SNP at position 2. Block E is evaluated for informativeness, is found to meet the threshold measure, is added to the set of candidate SNP haplotype blocks (step 350), and another SNP (here, SNP position 3) is added to this block (step 320) to create new block F, containing SNP positions 2 and 3, which is then analyzed, and so on Note that block H fails to meet the threshold measure of informativeness, is not added to the set of candidate SNP haplotype blocks (step 350), nor does another SNP get added to block H for analysis. Instead, a new block, I, is selected that contains only the SNP at position 3, and so on.

Once a set of candidate SNP blocks is constructed (step 350 of FIG. 3), analysis is performed on the set to select a final set of SNP blocks (step 160 of FIG. 1). The selection of the final set of SNP blocks can performed in a variety of ways. For example, referring back to FIG. 4, one could select the largest block containing SNP position 1 that passes the threshold test (block C, containing SNPs 1, 2 and 3), discard the smaller blocks that contain the same SNPs (blocks A and B). Then the next block selected might be the next block starting with SNP position 4 that is the largest block that meets the threshold test for informativeness (block G) and the smaller blocks that contain the same SNPs (blocks E and F) would be discarded. Such a method would give a set of final, non-overlapping SNP haplotype blocks that span the genomic region of interest, contain the SNPs of interest and that have a high level of informativeness. Thus, once all candidate SNP haplotype blocks are evaluated, the result may be, in a preferred embodiment, a set of non-overlapping SNP haplotype blocks that encompasses all the SNPs in the original set. Some groups, called isolates, may consist of only a single SNP, and by definition have an informativeness of 1. Other groups may consist of a hundred or more SNPs, and have an informativeness exceeding 30.

Figure 5A:
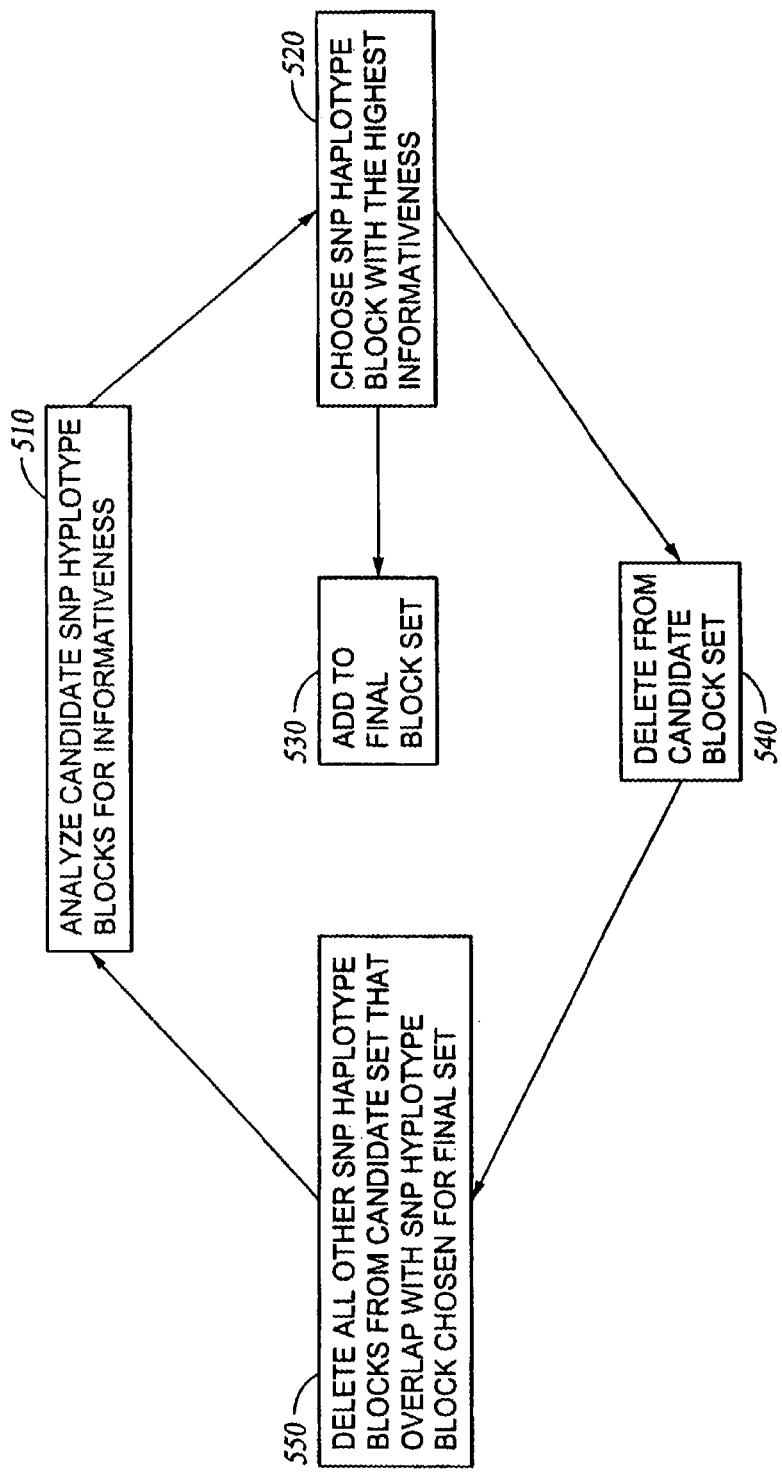
FIG. 5A is a schematic of one embodiment of a method for choosing a final set of SNP haplotype blocks.
Figure 5B:
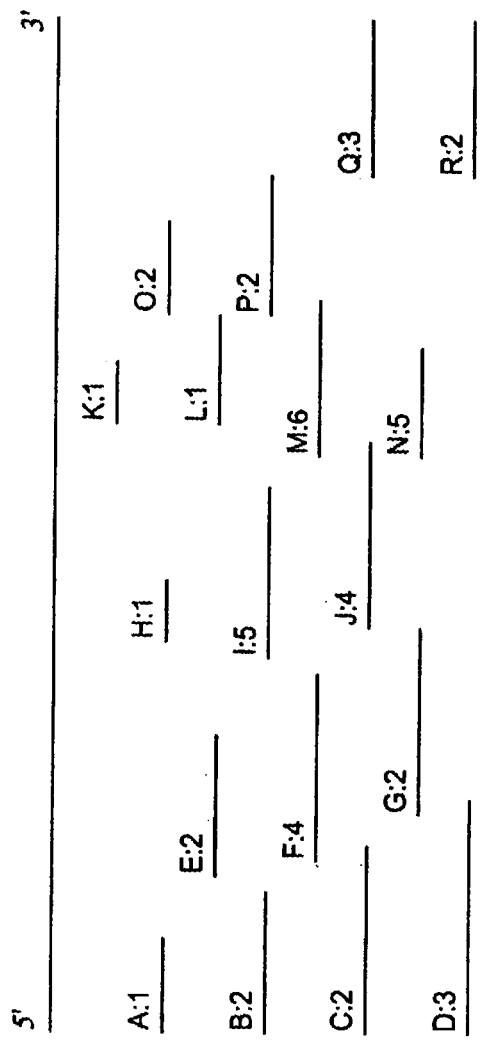
FIG. 5B is a simple employment of the method shown in FIG. 5A. The "letter:number" designations in FIG. 5B indicate "haplotype block ID:informativeness value" for each block.

An alternative method for selecting a final set of SNP haplotype blocks is shown in FIGS. 5A and 5B. Looking first at FIG. 5A, in a first step 510, the candidate SNP haplotype block set (generated, for example, by the methods described in FIGS. 3 and 4 herein) is analyzed for informativeness. In step 520, the candidate SNP haplotype block with the highest informativeness in the entire candidate set is chosen to be added to the final SNP haplotype block set (step 530). Once this candidate SNP haplotype block is chosen to be a member of the final SNP haplotype block set, it is deleted from the candidate block set (step 540), and all other candidate SNP haplotype blocks that overlap with the chosen block are deleted from the candidate SNP haplotype block set (step 550). Next, the candidate SNP haplotype blocks remaining in the candidate set are analyzed for informativeness (step 510), and the candidate SNP haplotype block with the highest informativeness is chosen to be added to the final SNP haplotype block set (steps 520 and 530). As before, once this SNP haplotype block is chosen to be a member of the final SNP haplotype block set, it is deleted from the candidate block set (step 540), and all other candidate SNP haplotype blocks that overlap with the chosen block are deleted from the candidate SNP haplotype block set (step 550). The process continues until a final set of non-overlapping SNP haplotype blocks that encompasses all the SNPs in the original set is constructed.

FIG. 5B illustrates a simple employment of the method of selecting a final set of SNP haplotype blocks described in FIG. 5A. In FIG. 5B, a sequence 5' to 3' is analyzed for SNPs, SNP haplotype patterns and candidate SNP haplotype blocks according to the methods of the present invention. Candidate SNP haplotype blocks contained within this sequence are indicated by their placement under the sequence, and are designated by a letter. In addition, after the letter, the informativeness of each block is indicated. For example, candidate SNP haplotype block A is located at the extreme 5' end of the sequence, and has an informativeness of 1. Candidate SNP haplotype block R is located at the extreme 3' end of the sequence, and has an informativeness of 2.

According to FIG. 5A, in a first step 510, the candidate SNP haplotype blocks are analyzed for informativeness, and in step 520, the SNP haplotype block with the highest informativeness is chosen to be added to the final SNP haplotype block set (steps 520 and 530). In the case of FIG. 5B, candidate SNP haplotype block M with an informativeness of 6 would be the first candidate SNP haplotype block selected to be added to the final SNP haplotype block set. Once SNP haplotype block M is selected, it is deleted or removed from the candidate set of SNP haplotype blocks (step 540), and all other candidate SNP haplotype blocks that overlap with SNP haplotype block M (blocks J, N, K, L, O and P) are deleted from the candidate SNP haplotype block set (step 550). Next, the remaining blocks of the candidate SNP haplotype block set, namely SNP haplotype blocks A, B, C, D, E, F, G, H, I, Q and R are analyzed for informativeness, and in step 520, the remaining SNP haplotype block with the highest informativeness, I, with an informativeness of 5, is chosen to be added to the final SNP haplotype block set (530) and deleted or removed from the candidate set of SNP haplotype blocks (step 540). Next, in step 550, all other candidate SNP haplotype blocks that overlap with SNP haplotype block I, here, only block H, is deleted from the candidate SNP haplotype block set. Again, the remaining blocks of the candidate SNP haplotype block set, namely SNP haplotype blocks A, B, C, D, E, F, G, Q and R are analyzed for informativeness. In step 520, the remaining SNP haplotype block with the highest informativeness, block F, with an informativeness of 4, is chosen to be added to the final SNP haplotype block set (530) and deleted or removed from the candidate set of SNP haplotype blocks (step 540). Next, all other candidate SNP haplotype blocks that overlap with SNP haplotype block F—here, blocks E, G, C and D—are deleted from the candidate SNP haplotype block set, and the remaining blocks of the candidate SNP haplotype block set, namely SNP haplotype blocks A, B, Q and R, are analyzed for informativeness, and so on.

Other methods can be employed to select a final set of SNP haplotype blocks for analysis from the set of candidate SNP haplotype blocks (step 160 of FIG. 1). For example, algorithms known in the art may be applied for this purpose. For example, shortest-paths algorithms may be used (see, generally, Cormen, Leiserson, and Rivest, *Introduction to Algorithms* (MIT Press) pp. 514-78 (1994). In a shortest-paths problem, a weighted, directed graph G=(V,E), with weight function w: E→R mapping edges to real-valued weights is given. The weight of path $p=(v_0, v_1, \ldots v_k)$ is the sum of the weights of its constituent edges:

$$w(p) = \sum_{i=1}^{k} w(v_{i-1}, v_i).$$

The shortest-path weight from u to v is defined by δ(u,v) being equal to min w(p):u→v if there is a path from u to v; otherwise, δ(u,v) is equal to infinity. A shortest path from vertex u to vertex v is then defined as any path p with weight w(p)=δ(u,v). Edge weights can be interpreted as various metrics: for example, distance, time, cost, penalties, loss, or any other quantity that accumulates linearly along a path that one wishes to minimize. In the embodiment of the shortest path algorithm used in applications of this invention, each SNP haplotype block would be considered a "vertex" with an "edge" defined for each boundary of the block. Each SNP haplotype block has a relationship to each other SNP haplotype block, with a "cost" for each edge. Cost is determined by parameters of choice, such as overlap (or the extent thereof) of the vertices or gaps between the vertices.

Single-source shortest-paths problems focus on a given graph G=(V,E), where a shortest path from a given source vertex s∈V to every vertex v∈V is determined. Additionally, variants of the single source algorithm may be applied. For example, one may apply a single-destination shortest-paths solution where a shortest path to a given destination vertex t from every vertex v is found. Reversing the direction of each edge in the graph reduces this problem to a single-source problem. Alternatively, one may apply a single-pair shortest-path problem where the shortest path from u to v for given vertices u and v is found. If the single-source problem with source vertex u is solved, the single-source shortest path problem is solved as well. Also, the all-pairs shortest-paths approach may be employed. In this case, a shortest path from u to v for every pair of vertices u and v is found—a single-source algorithm is run from each vertex.

One single-source shortest-path algorithm that may be employed in the methods of the present invention is Dijkstra's algorithm. Dijkstra's algorithm solves the single-source shortest-paths problem on a weighted, directed graph G=(V,E) for the case in which all edge weights are non-negative. Dijkstra's algorithm maintains a set of vertices, S, whose final shortest-path weights from a sources have already been determined. That is, for all vertices v being elements of S, $d[v]=\delta(s,v)$. The algorithm repeatedly selects the vertex u as an element of V-S with the minimum shortest-path estimate, inserts u into S, and relaxes all edges radiating from u. In one implementation, a priority queue Q that contains all the vertices in V-S, keyed by their d values, is maintained. This implementation assumes that graph G is represented by adjacency lists.

| Dijkstra (G, w, s) | |
|---|---|
| 1 | INITIALIZE-SINGLE SOURCE (G, s) |
| 2 | S ← Ø |
| 3 | Q ← V[G] |
| 4 | while Q ≠ Ø |
| 5 | do u ← EXTRACT-MIN (Q) |
| 6 | S ← SU {u} |
| 7 | for each vertex v ∈ Adj[u] |
| 8 | do RELAX (u, v, w) |

Thus, G in this case is the graph of linear coverage of the genomic sequence being analyzed and S is the set of vertices selected. Once one vertex is selected that covers a particular area of the genomic sequence, other vertices that overlap this sequence can be discarded.

Other algorithms that may be used for selecting SNP haplotype blocks include a greedy algorithm (again, see, Cormen, Leiserson, and Rivest, *Introduction to Algorithms* (MIT Press) pp. 329-55 (1994)). A greedy algorithm obtains an optimal solution to a problem by making a sequence of choices. For each decision point in the algorithm, the choice that seems best at the moment is chosen. This heuristic strategy does not always produce an optimal solution. Greedy algorithms differ from dynamic programming in that in dynamic programming, a choice is made at each step, but the choice may depend on the solutions to subproblems. In a greedy algorithm, whatever choice seems best at the moment is chosen and then subproblems arising after the choice is made are solved. Thus, the choice made by a greedy algorithm may depend on the choices made thus far, but cannot depend on any future choices or on the solutions to subproblems. One variation of greedy algorithms is Huffman codes. A Huffman greedy algorithm constructs an optimal prefix code and the algorithm builds a tree T corresponding to the optimal code in a bottom-up manner. It begins with a set of |C| leaves and performs a sequence of |C|-1 "merging" operations to create the final tree. For example, assuming C is a set of n characters and that each character c∈C is an object with a defined frequency f[c]; a priority queue Q, keyed on f, is used to identify the two least-frequent objects to merge together. The result of the merger of two objects is a new object whose frequency is the sum of the frequencies of the two objects that were merged. For example:

| | |
|---|---|
| 1. | n←|C| |
| 2. | Q←C |

| | |
|---|---|
| 3. | for i←1 to n-1 |
| 4. | do z←ALLOCATE-NODE( ) |
| 5. | x←left[z]←EXTRACT-MIN(Q) |
| 6. | y←right[z]←EXTRACT-MIN(Q) |
| 7. | f[z]←f[x] + f[y] |
| 8. | INSERT (Q, z) |
| 9. | return EXTRACT-MIN(Q) |

Line 2 initializes the priority queue Q with the characters in C. The for loop in lines 3-8 repeatedly extracts the two nodes x and y of lowest frequency from the queue, and replaces them in the queue with a new node z representing their merger. The frequency of z is computed as the sum of the frequencies of x and y in line 7. The node z has x as its left child and y as its right child. After n-1 mergers, the one node left in the queue—the root of the code tree—is returned in line 9.

Again, these methods result in a set of final, non-overlapping SNP haplotype blocks that encompasses all SNPs evaluated in a particular genomic region. An important result of selecting SNPs, SNP haplotype blocks and SNP haplotype patterns according to the methods of the present invention, is that in some embodiments during the calculation of informativeness of SNP haplotype blocks, informative SNPs for each SNP haplotype block and pattern are determined. Informative SNPs allow for data compression.

In one embodiment of the present invention, the selection of at least $\log_2 p$ SNPs from each group containing p patterns (rounding up to the nearest integer) provides one set of informative SNPs which are unusually powerful for predicting genotype/phenotype associations. One skilled in the art recognizes that in other analyses it is not necessary to use spatially contiguous groups to determine such a subset. For example, in some embodiments of the present invention, it may be desirable to identify sets of non-adjacent SNPs that statistically are passed on in a fashion analogous to that of SNP haplotype blocks even though they are not spatially contiguous on the DNA strand.

Figure 6:
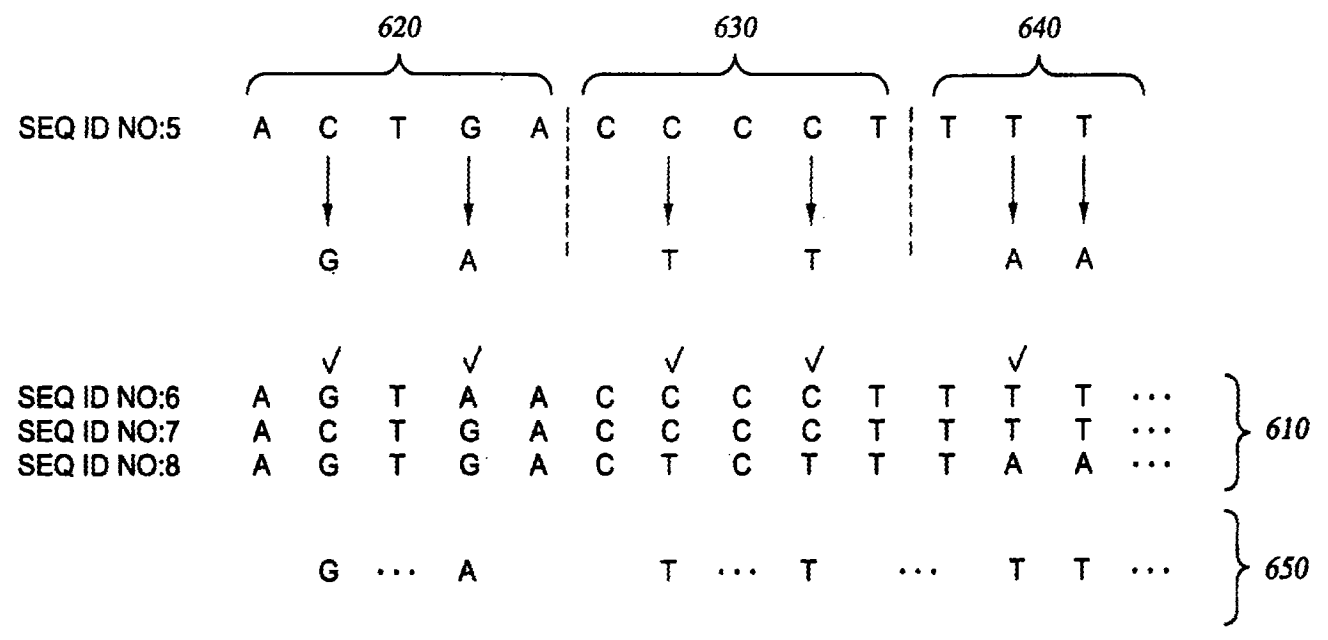

In order to determine SNP haplotype blocks that will be used in association studies accurately (build an accurate baseline of SNPs and SNP haplotype blocks and patterns), it is necessary to examine more than a few individual DNA strands. FIG. 6 illustrates the importance of examining at least about five different DNA strands for determining SNP haplotype blocks and for the selection of informative SNPs. The top portion of FIG. 6 illustrates the sequence of a hypothetical stretch of DNA, with the variant positions indicated and variant block boundaries drawn; however, SNP haplotype block boundaries would not be known ab initio. Sequencing results 610 show the results of sequencing haploid DNA of three individuals. As shown, in general it is possible to have identified a large fraction of the common SNPs after a relatively small number of individuals have been sequenced. In the case in FIG. 6, the SNPs at each location shown in the top portion of FIG. 6 have been identified, as indicated by check marks.

If, however, further individuals are not evaluated, the block boundaries would not be correctly, identified at this stage. For example, while one could at this stage draw block boundaries between blocks 620 and 630 (note that the first C→G variant predicts the first G→A variant, and the first C→T variant predicts the second C→T variant), it is not possible to distinguish between the blocks 630 and 640 at this stage. At this stage it appears that the first C→T variant would predict the first and second T→A variants. Accordingly, a more statistically significant sample set is required to draw the block boundaries. For example, in the methods of the present invention, the number of DNA strands analyzed to determine SNP haplotype blocks, SNP haplotype patterns, and/or informative SNPs is a plurality, for example, at least about five or at least about 10. In preferred embodiments, the number of DNA stands is at least 16. In more preferred embodiments, the number of DNA strands analyzed to determine SNP haplotype blocks, SNP haplotype patterns, and/or informative SNPs is at least 25. However, once relevant SNPs have been identified e, SNP discovery has been performed), it is possible to genotype only the variant positions in the remaining samples to complete the process of identifying block boundaries without sequencing the entire stretch of genomic DNA. For examples of such methods, see U.S. Ser. No. 10/042,819, filed Jan. 6, 2002, entitled "Whole Genome Scanning".

The results of performing a genotyping process on only the SNPs in another hypothetical genomic sample are shown in FIG. 6 at 650. As shown, by performing this additional genotyping step, it is now possible to see that blocks 630 and 640 are distinguishable. Specifically, it is now possible to see that the first C→T variant does not track with the first and second T→A variants, but instead, the first C→T variant can be used to predict only the second C→T variant (and vice versa) and the first T→A variant can be used only to predict the second T→A variant (and vice versa).

In addition to the aspects of the present invention described above, a specific embodiment of the present invention is that it can be employed to resolve ambiguous SNP haplotype sequences for data analysis. For example, a SNP may be ambiguous because data from a gel sequencing operation or array hybridization experiment does not give a clear, result "Resolving" in this case may mean, e.g., resolving ambiguous SNP locations in a SNP haplotype sequence by matching the SNP haplotype sequence to the SNP haplotype pattern to which the SNP haplotype sequence most closely relates. Additionally, "resolving" may mean removing an ambiguous SNP haplotype sequence from data analysis.

Figure 7A:
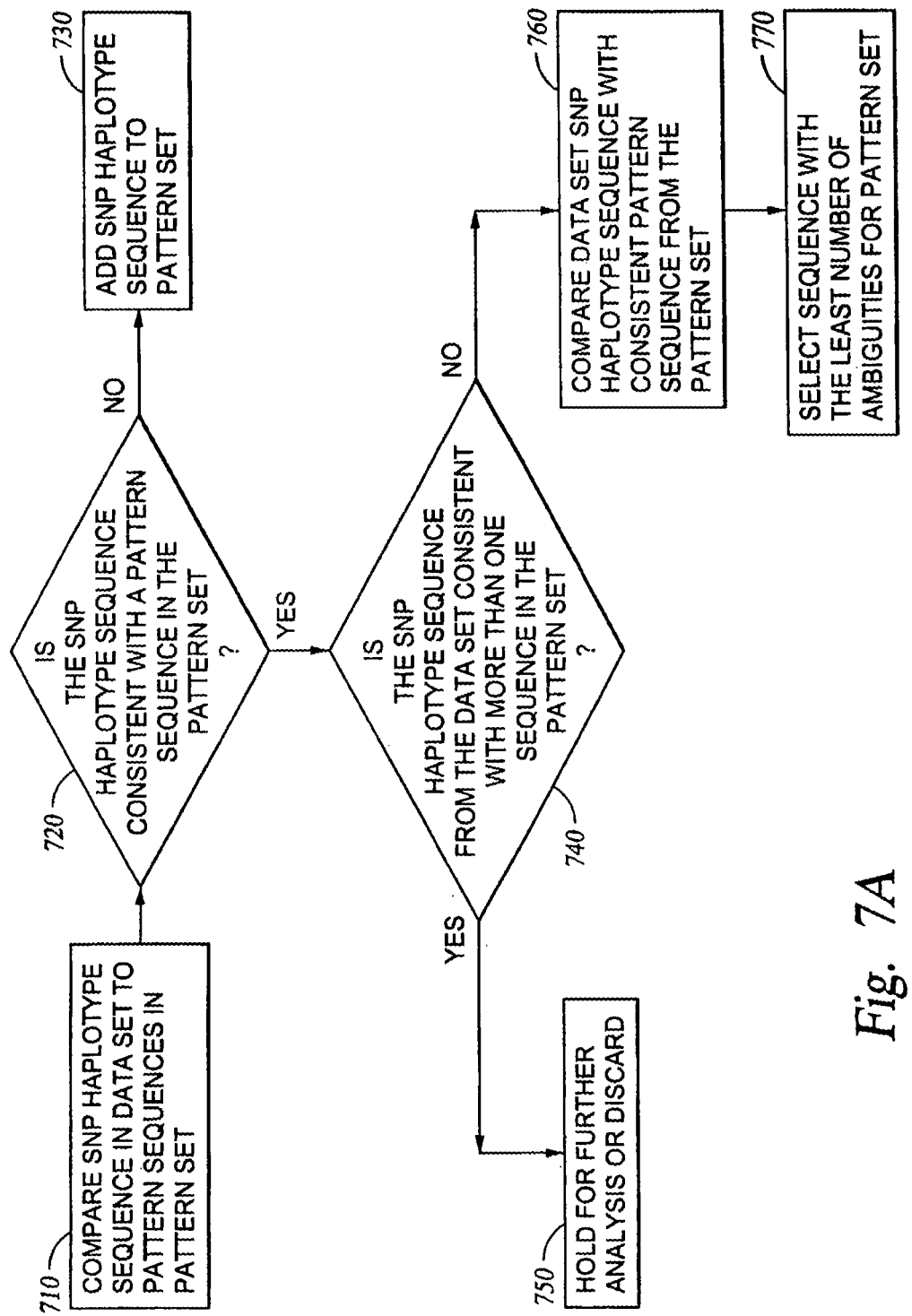
FIG. 7A is a schematic showing one embodiment for resolving variant ambiguities and/or SNP haplotype pattern ambiguities.

In one embodiment of resolving ambiguous SNP haplotype sequences, SNP haplotype sequences are placed in a data set for possible addition to a pattern set. The data set will contain all SNP haplotype sequences that are to be evaluated for possible assignment to a SNP haplotype pattern. Referring now to FIG. 7A, in step 710, the SNP haplotype sequences in the data set are compared, one by one, to the pattern sequences in the pattern set. In some cases, there will be no patterns in the pattern set initially, though in other cases some or all pattern sequences may be known beforehand. In step 720, a query is made: is the SNP haplotype sequence from the data set consistent with a pattern sequence in the pattern set? If the answer is no, step 730 provides the SNP haplotype sequence being evaluated will be added to the pattern set. If the answer is yes, another query is made (740): is the SNP haplotype sequence from the data set consistent with more than one pattern sequence in the pattern set?

If the answer is yes, the SNP sequence from the data set may be discarded or, in some embodiments, held for further or different analyses (step 750). If the answer to the second query is no, then, in step 760, the SNP sequence from the data set is compared to the pattern sequence from the pattern set with which it is consistent. From these two sequences, the SNP sequence with the least number of ambiguities is selected and placed in the pattern set (770). The SNP sequence containing the more ambiguities may be discarded, or, in some embodiments, held for further or different types of analyses.

Figure 7B:
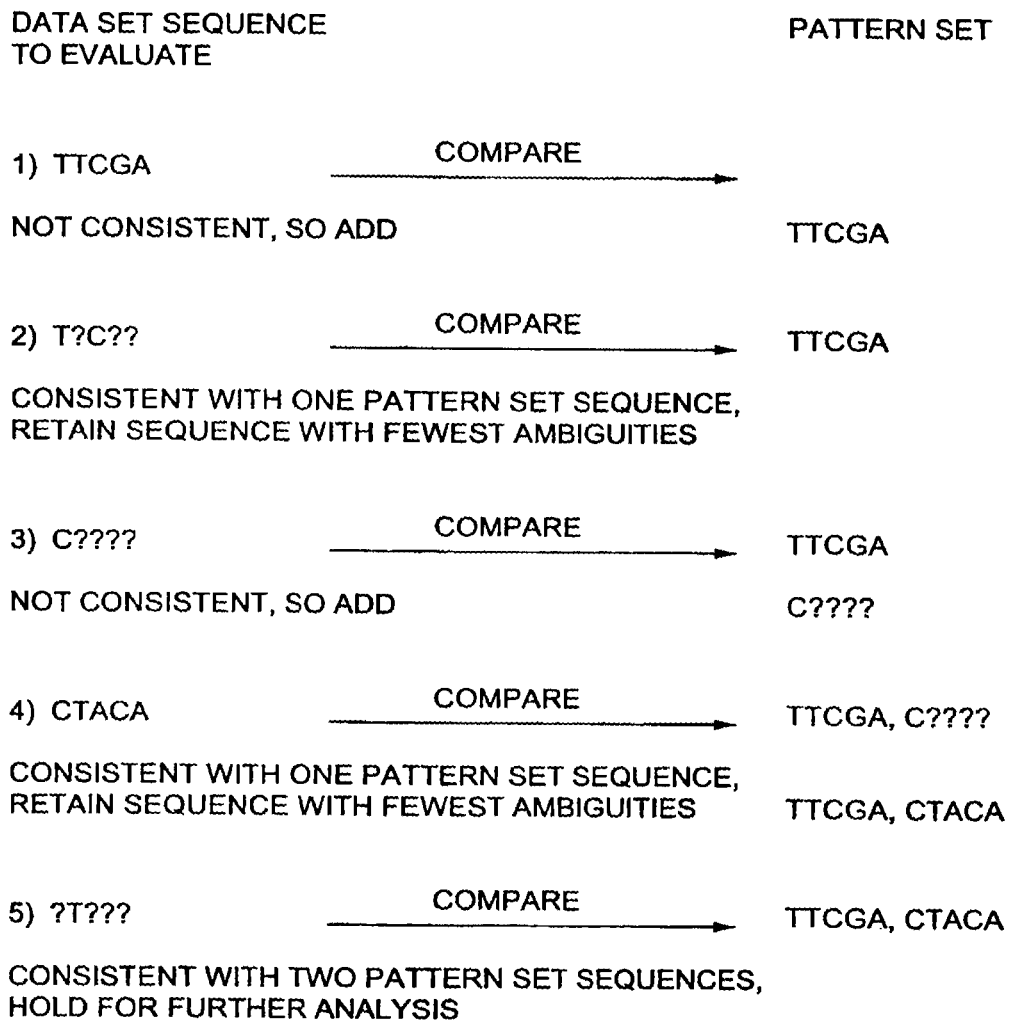
FIG. 7B illustrates a simple employment of the method shown in FIG. 7A.

The resolving process may be understood further by referring to FIGS. 7A and 7B. In FIG. 7B, a first SNP sequence, TTCGA, is compared to the sequences contained in the pattern set (step 710). At this point, there are no pattern sequences contained in the pattern set, thus TTCGA is not consistent with any pattern sequence in the pattern set. This occurrence of SNP sequence TTCGA is then removed from the data set (or is retained for different analyses), and added to the pattern set (730). The pattern set now has one pattern sequence, TTCGA.

Looking again at FIG. 7B, the second SNP sequence in the data set, T?C??, is compared to the sequence contained in the pattern set (step 710). Now there is one pattern sequence in the pattern set, TTCGA, and T?C?? is consistent with sequence (step 720). The answer to the second query (740), whether SNP sequence T?C?? is consistent with more than one pattern sequence in the pattern set, is no, as currently there is only one pattern sequence, TTCGA, in the pattern set. In step 760, T?C?? is compared to TTCGA to determine which sequence has the more ambiguities. T?C?? clearly does; thus, TTCGA is retained in the pattern set (770) and T?C?? may be discarded or held for further analyses.

The third sequence of the data set in FIG. 7B is C????. C???? first is compared to TTCGA (step 710), is found not to be consistent with TTCGA (720), and is thus added to the pattern set (730). The fourth sequence in FIG. 7B is CTACA. CTACA is compared to TTCGA and C???? (the pattern sequences in the pattern set, step 710), and is found to be consistent with C???? (720). The second query (740) now is made: is CTACA consistent with both C???? and TTCGA? The answer is no, so C???? and CTACA are then compared (760) and the sequence with the least number of ambiguities, in this case, CTACA, is held in the pattern set and C???? is discarded (removed from analysis), or held for further analyses (770).

The fifth SNP sequence in the data set in FIG. 7B is ?T??A. This SNP sequence is compared to pattern sequences TTCGA and CTACA (710) and is found to be consistent with both TTCGA and CTACA. Thus, the answer to query 740 is yes: ?T??A is consistent with more than one pattern sequence in the pattern set. In step 750, SNP sequence ?T??A is held for further analysis or discarded (removed from analysis).

Another approach to resolving allows that if, for example, one pattern sequence is CCATT? and a SNP sequence from the data set is C?ATTG, the sequences are "combined" to solve the ambiguities (CCATTG), and the "combined" sequence is added to the pattern set. Additional array hybridizations, sequencing or other techniques known in the art may be employed to analyze ambiguous SNP nucleotide positions.

Association of Phenotypes with SNP Haplotypes Blocks and Patterns

The SNP haplotype blocks, SNP haplotype patterns and/or informative SNPs identified may be used for a variety of genetic analyses. For example, once informative SNPs have been identified, they may be used in a number of different assays for association studies. For example, probes may be designed for microarrays that interrogate these informative SNPs. Other exemplary assays include, e.g., the Taqman assays and Invader assays described supra, as well as conventional PCR and/or sequencing techniques.

In some embodiments, as shown in step 170 of FIG. 1, the haplotype patterns identified may be used in the abovereferenced assays to perform association studies. This may be accomplished by determining haplotype patterns in individuals with the phenotype of interest (for example, individuals exhibiting a particular disease or individuals who respond in a particular manner to administration of a drug) and comparing the frequency of the haplotype patterns in these individuals to the haplotype pattern frequency in a control group of individuals. Preferably, such SNP haplotype pattern determinations are genome-wide; however, it may be that only specific regions of the genome are of interest, and the SNP haplotype patterns of those specific regions are used. In addition to the other embodiments of the methods of the present invention disclosed herein, the methods additionally allow for the "dissection" of a phenotype. That is, a particular phenotype may result from two or more different genetic bases. For example, obesity in one individual may be the result of a defect in Gene X, while the obesity phenotype in a different individual may be the result of mutations in Gene Y and Gene Z. Thus, the genome scanning capabilities of the present invention allow for the dissection of varying genetic bases for similar phenotypes. Once specific regions of the genome are identified as being associated with a particular phenotype, these regions may be used as drug discovery targets (step 180 of FIG. 1) or as diagnostic markers (step 190 of FIG. 1).

As described in the previous paragraph, one method of conducting association studies is to compare the frequency of SNP haplotype patterns in individuals with a phenotype of interest to the SNP haplotype pattern frequency in a control group of individuals. In a preferred method, informative SNPs are used to make the SNP, haplotype pattern comparison. The approach of using informative SNPs has tremendous advantage over other whole genome scanning or genotyping methods known in the art to date, for instead of reading all 3 billion bases of each individual's genome—or even reading the 3-4 million common SNPs that may be found—only informative SNPs from a sample population need to be determined. Reading these particular, informative SNPs provides sufficient information to allow statistically accurate association data to be extracted from specific experimental populations, as described above.

Figure 8:
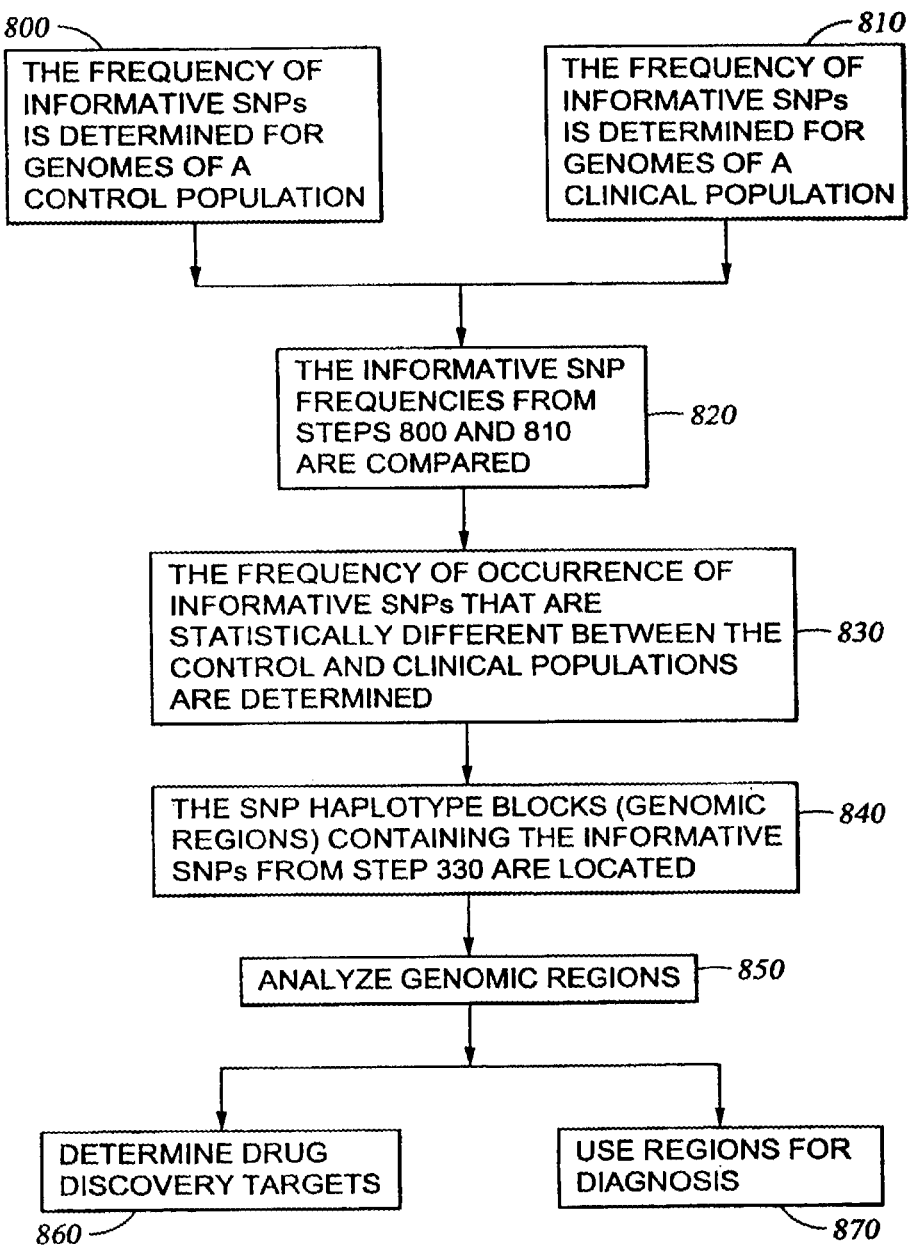
FIG. 8 is a schematic of one embodiment of using the methods of the present invention in an association study.

FIG. 8 illustrates an embodiment of one method of determining genetic associations using the methods of the present invention. In step 800, the frequency of informative SNPs is determined for genomes of a control population. In step 810, the frequency of informative SNPs is determined for genomes of a clinical population. Steps 800 and 810 may be performed by using the aforementioned SNP assays to analyze the informative SNPs in a population of individuals. In step 820, the informative SNP frequencies from steps 800 and 810 are compared. Frequency comparisons may be made, for example, by determining the minor allele frequency (number of individuals with a particular minor allele divided by the total number of individuals) at each informative SNP location in each population and comparing these minor allele frequencies. In step 830, the informative SNPs displaying a difference between the frequency of occurrence in the control versus clinical populations are selected for analysis. Once informative SNPs are selected, the SNP haplotype blocks that contain the informative SNPs are identified, which in turn identifies the genomic region of interest (step 840). The genomic regions are analyzed by genetic or biological methods known in the art (step 850), and the regions are analyzed for possible use as drug discovery targets (step 860) or as diagnostic markers (step 870), as described in detail below.

Uses of Identified Genomic Sequences

Once a genetic locus or multiple loci in the genome are associated with a particular phenotypic trait—for example, a disease susceptibility locus—the gene or genes or regulatory elements responsible for the trait can be identified. These genes or regulatory elements may then be used as therapeutic targets for the treatment of the disease, as shown in step 180 of FIG. 1 or step 860 of FIG. 8. The genomic sequences identified by the methods of the present invention may be, genic or nongenic sequences. The term "gene" intended to mean the open reading frame (ORF) encoding specific polypeptides, intronic regions, as well as adjacent 5' and 3' non-coding nucleotide sequences involved in the regulation of expression of the gene up to about 10 kb beyond the coding region, but possibly further in either direction. The ORFs of an identified gene may affect the disease state due to their effect on protein structure. Alternatively, the noncoding sequences of the identified gene or nongenic sequences may affect the disease state by impacting the level of expression or specificity of expression of a protein. Generally, genomic sequences are studied by isolating the identified gene substantially free of other nucleic acid sequences that do not include the genic sequence. The DNA sequences are used in a variety of ways. For example, the DNA may be used to detect or quantify expression of the gene in a biological specimen. The manner, in which cells are probed for the presence of particular nucleotide sequences is well established in the literature and does not require elaboration here, however, see, e.g., Sambrook, et al., *Molecular Cloning: A Laboratory Manual* (Cold Spring Harbor Laboratory, New York) (1989)

In addition, the sequence of the gene, including flanking promoter regions and coding regions, may be mutated in various ways known in the art to generate targeted changes in expression level, or changes in the sequence of the encoded protein, etc. The sequence changes may be substitutions, insertions, translocations or deletions. Deletions may include large changes, such as deletions of an entire domain or exon. Techniques for in vitro mutagenesis of cloned genes are known. Examples of protocols for site specific mutagenesis may be found in Gustin, et al., *Biotechniques* 14:22 (1993); Barany, *Gene* 37:111-23 (1985); Concern, et al., *Mol. Gen. Genet.* 199:537-9 (1985); Prentki, et al., *Gene* 29:303-13 (1984); Sambrook, et al., *Molecular Cloning: A Laboratory Manual* (Cold Spring Harbor Press) pp. 15.3-15.108 (1989); Weiner, et al., *Gene* 126:35-41 (1993); Sayers, et al., *Biotechniques* 13:592-6 (1992); Jones and Winistorfer, *Biotechniques* 12:528-30 (1992); and Barton, et al., *Nucleic Acids Res.* 18:7349-55 (1990). Such mutated genes may be used to study structure/function relationships of the protein product, or to alter the properties of the protein that affect its function or regulation.

The identified gene may be employed for producing all or portions of the resulting polypeptide. To express a protein product, an expression cassette incorporating the identified gene may be employed. The expression cassette or vector generally provides a transcriptional and translational initiation region, which may be inducible or constitutive, where the coding region is operably linked under the transcriptional control of the transcriptional initiation region, and a transcriptional and translational termination region. These control regions may be native to the identified gene, or may be derived from exogenous sources.

The peptide may be expressed in prokaryotes or eukaryotes in accordance with conventional methods, depending upon the purpose for expression. For large scale production of the protein, a unicellular organism, such as *E. coli, B.* subtilis, S. cerevisiae, insect cells in combination with baculovirus vectors, or cells of a higher organism such as vertebrates, particularly mammals, e.g. COS 7 cells, may be used as the expression host cells. In many situations, it may be desirable to express the gene in eukaryotic cells, where the gene will benefit from native folding and post-translational modifications. Small peptides also can be synthesized in the laboratory. With the availability of the protein or fragments thereof in large amounts, the protein may be isolated and purified in accordance with conventional ways. A lysate may be prepared of the expression host and the proteins or fragments thereof purified using HPLC, exclusion chromatography, gel electrophoresis, affinity chromatography, or other purification techniques.

An expressed protein may, be used for the production of antibodies, where short fragments induce the expression of antibodies specific for the particular polypeptide (monoclonal antibodies), and larger fragments or the entire, protein allow for the production of antibodies over the length of the polypeptide (polyclonal antibodies). Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes are immortalized by cell fusion and screened for high affinity antibody binding. The immortalized cells, i.e, hybridomas, producing the desired antibodies may then be expanded. For further description, see *Monoclonal Antibodies: A Laboratory Manual*, Harlow and Lane, eds. (Cold Spring Harbor Laboratories, Cold Spring Harbor, N.Y.) (1988). If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage "display" libraries, usually in conjunction with in vitro affinity maturation.

The identified genes, gene fragments, or the encoded protein or protein fragments may be useful in gene therapy to treat degenerative and other disorders. For example, expression vectors may be used to introduce the identified gene into a cell. Such vectors generally have convenient restriction sites located near the promoter sequence to provide for the insertion of nucleic acid sequences in a recipient genome. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to be transiently or stably maintained in the cells. The gene or protein product may be introduced directly into tissues or host cells by any number of routes, including viral infection, microinjection, or fusion of vesicles. Jet injection may also be used for intramuscular administration, as described by Furth, et al., *Anal. Biochem,* 205:365-68 (1992). Alternatively, the DNA may be coated onto gold microparticles, and delivered intradermally by a particle bombardment device, or "gene gun" as described in the literature (see, for example, Tang, et al., *Nature,* 356:152-54 (1992)).

Antisense molecules can be used to down-regulate expression of the identified gene in cells. The antisense reagent may be antisense oligonucleotides, particularly synthetic antisense oligonucleotides having chemical modifications, or nucleic acid constructs that express such antisense molecules as RNA. A combination of antisense molecules may be administered, where a combination may comprise multiple different sequences.

As an alternative to antisense inhibitors, catalytic nucleic acid compounds, e.g., ribozymes, anti-sense conjugates, etc., may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman, et al., *Nucl. Acids Res.* 23:4434-42 (1995)). Examples of oligonucleotides with catalytic activity are described in WO 9506764. Conjugates of antisense oligonucleotides with a metal complex, e.g. terpyridylCu(II), capable of mediating mRNA hydrolysis are described in Bashkin, et al., *Appl. Biochem. Biotechnol.* 54:43-56 (1995).

In addition to using the identified sequences for gene therapy, the identified nucleic acids can be used to generate genetically modified non-human animals to create animal models of diseases or to generate site-specific gene modifications in cell lines for the study of protein function or regulation. The term "transgenic" is intended to encompass genetically modified animals having an exogenous gene that is stably transmitted in the host cells where, for example, the gene may be altered in sequence to produce a modified protein, or may be a reporter gene operably linked to an exogenous promoter. Transgenic animals may be made through homologous recombination, where the endogenous gene locus is altered, replaced or otherwise disrupted. Alternatively, a nucleic acid construct may be randomly integrated into the genome. Vectors for stable integration include plasmids, retroviruses and other animal viruses, YACs, and the like. Of interest are transgenic mammals, e.g., cows, pigs, goats, horses, etc., and, particularly, rodents, e.g., rats, mice, etc.

Investigation of genetic function may also utilize non-mammalian models, particularly using those organisms that are biologically and genetically well-characterized, such as *C. elegans, D. melanogaster* and *S. cerevisiae*. The subject gene sequences may be used to knock-out corresponding gene function or to complement defined genetic lesions in order to determine the physiological and biochemical pathways involved in protein function. Drug screening may be performed in combination with complementation or knock-out studies, e.g., to study progression of degenerative disease, to test therapies, or for drug discovery.

In addition, the modified cells or animals are useful in the study of protein function and regulation. For example, a series of small deletions and/or substitutions may be made in the identified gene to determine the role of different domains in enzymatic activity, cell transport or localization, etc. Specific constructs of interest include, but are not limited to, antisense constructs to block gene expression, expression of dominant negative genetic mutations, and over-expression of the identified gene. One may also provide for expression of the identified gene or variants thereof in cells or tissues where it is not normally expressed or at abnormal times of development. In addition, by providing expression of a protein in cells in which it is not normally produced, one can induce changes in cellular behavior that provide information regarding the normal function of the protein.

Protein molecules may be assayed to investigate structure/function parameters. For example, by providing for the production of large amounts of a protein product of an identified gene, one can identify ligands or substrates that bind to, modulate or mimic the action of that protein product. Drug screening identifies agents that provide, e.g., a replacement or enhancement for protein function in affected cells, or for agents that modulate or negate protein function. The term "agent" as used herein describes any molecule, e.g. protein or small molecule, with the capability of altering, mimicking or masking, either directly or indirectly, the physiological function of an identified gene or gene product. Generally a plurality of assay mixtures are run in parallel with different concentrations of the agent to obtain a differential response to the various concentrations. Typically, one of these concentrations serves as a negative control, i.e., at zero concentration or below the level of detection.

A wide variety of assays may be used for this purpose, including labeled in vitro protein-protein binding assays, protein-DNA binding assays, electrophoretic mobility shift assays, immunoassays for protein binding, and the like. Also, all or a fragment of the purified protein may be used for determination of three-dimensional crystal structure, which can be used for determining the biological function of the protein or a part thereof, modeling intermolecular interactions, membrane fusion, etc.

Candidate agents encompass numerous chemical classes, though typically they are organic molecules or complexes, preferably small organic compounds, having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, and frequently at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs.

Where the screening assay is a binding assay, one or more of the molecules may be coupled to a label, where the label can directly or indirectly provide a detectable signal. Various labels include radioisotopes, fluorescers, chemiluminescers, enzymes, specific binding molecules, particles, e.g., magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

A variety of other reagents may be included in the screening assay. These include reagents like salts, neutral proteins, e.g., albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc., may be used.

Agents may be combined with a pharmaceutically acceptable carrier, including any and all solvents, dispersion media, coatings, anti-oxidant, isotonic and absorption delaying agents and the like. The use of such media and agents for pharmaceutically active substances is well known in the art. Except insofar as any conventional media or agent is incompatible with the active ingredient, its use in the therapeutic compositions and methods described herein is contemplated. Supplementary active ingredients can also be incorporated into the compositions.

The formulation may be prepared for use in various methods for administration. The formulation may be given orally, by inhalation, or may be injected, e.g. intravascular, intratumor, subcutaneous, intraperitoneal, intramuscular, etc. The dosage of the therapeutic formulation will vary widely, depending upon the nature of the disease, the frequency of administration, the manner of administration, the clearance of the agent from the host, and the like. The initial dose may be larger, followed by smaller maintenance doses. The dose may be administered as infrequently as once, weekly or biweekly, or fractionated into smaller doses and administered daily, semi-weekly, etc., to maintain an effective dosage level. In some cases, oral administration will require a different dose than if administered intravenously. Identified agents of the invention can be incorporated into a variety of formulations for therapeutic administration. More particularly, the complexes can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the agents can be achieved in various ways. Agents may be systemic after administration or may be localized by the use of an implant that acts to retain the active dose at the site of implantation.

The following methods and excipients are merely exemplary and are in no way limiting. For oral preparations, an agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Additionally, agents may be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Further, agents may be utilized in aerosol formulation to be administered via inhalation. The agents identified by the present invention can be formulated into pressurized acceptable propellants such as dichlorodifluoromethane, propane, nitrogen and the like. Alternatively, agents may be made into suppositories by mixing with a variety of bases such as emulsifying bases or water-soluble bases. Further, identified agents of the present invention can be administered rectally via a suppository. The suppository can include vehicles such as cocoa butter, carbowaxes and polyethylene glycols, which melt at body temperature, yet are solidified at room temperature.

Implants for sustained release formulations are well-known m the art. Implants are formulated as microspheres, slabs, etc. with biodegradable or non-biodegradable polymers. For example, polymers of lactic acid and/or glycolic acid form an erodible polymer that is well-tolerated by the host. The implant containing identified agents of the present invention may be placed in proximity to the site of action, so that the local concentration of active agent is increased relative to the rest of the body. Unit dosage forms for oral or rectal administration such as syrups, elixirs, and suspensions may be provided wherein each dosage unit, for example, teaspoonful, tablespoonful, gel capsule, tablet or suppository, contains a predetermined amount of the compositions of the present invention. Similarly, unit dosage forms for injection or intravenous administration may comprise the compound of the present invention in a composition as a solution in sterile water, normal saline or another pharmaceutically acceptable carrier. The specifications for the novel unit dosage forms of the present invention depend on the particular compound employed and the effect to be achieved, and the pharmacodynamics associated with each active agent in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

A therapeutic dose of an identified agent is administered to a host suffering from a disease or disorder. Administration may be topical, localized or systemic, depending on the specific disease. The compounds are administered at an effective dosage such that over a suitable period of time the disease progression may be substantially arrested. It is contemplated that the composition will be obtained and used under the guidance of a physician for in vivo use. The dose will vary depending on the specific agent and formulation utilized, type of disorder, patient status, etc., such that it is sufficient to address the disease or symptoms thereof, while minimizing side effects. Treatment may be for short periods of time, e.g., after trauma, or for extended periods of time, e.g., in the prevention or treatment of schizophrenia.

The SNPs identified by the present invention may be used to analyze the expression pattern of an associated, gene and the expression pattern correlated to a phenotypic trait of the organism such as disease susceptibility or drug responsiveness. The expression pattern in various tissues can be determined and used to identify ubiquitous expression patterns, tissue specific expression patterns, temporal expression patterns and expression patterns induced by various external stimuli such as chemicals or electromagnetic radiation. Such determinations would provide information regarding function of the gene and/or its protein product.

The newly identified sequences also may be used as diagnostic markers, i.e., to predict a phenotypic characteristic such as disease susceptibility or drug responsiveness. In addition, the methods of the present invention may be used to stratify populations for clinical studies. As such, the genes or fragments thereof may be used as probes to determine whether the same nucleic acid sequence is present in the genome of an organism being tested. In addition, the probes may be used to monitor RNA or mRNA, levels within the organism to be tested or a part thereof, such as a specific tissue or organ, so as to determine the expression level of the marker where the expression level can be correlated to a particular phenotypic characteristic of the organism. Likewise, the marker may be assayed at the protein level using any customary technique such as immunological methods— Western blots, radioimmune precipitation and the like—or activity based assays measuring an activity associated with the gene product. Moreover, when a phenotype cannot clearly distinguish between similar diseases having different genetic bases, the methods of the present invention can be used to identify correctly the disease.

Also, it should be apparent that the methods of the present invention can be used on organisms aside from humans. For example, when the organism is an animal, the methods of the invention may be used to identify loci associated, e.g., with disease resistance/or susceptibility, environmental tolerance, drug response or the like, and when the organism is a plant, the method of the invention may be used to identify loci associated with disease resistance/or susceptibility, environmental tolerance and or herbicide resistance.

It is to be understood that this invention is not limited to the particular methodology, protocols, cell lines, animal species or genera, and reagents described, as such may vary. It is also to be understood that the terminology used herein is, for the purpose of describing particular embodiments only, and is not intended to limit the scope of the present invention, which will be limited only by the appended claims.

Databases

The present invention includes databases containing information concerning variations, for instance, information concerning SNPs, SNP haplotype blocks, SNP haplotype patterns and informative SNPs. In some embodiments, the databases of the present invention may comprise information on one or more haplotype patterns associated with one or more phenotypic traits. Databases may also contain information associated with a given variation such as descriptive information about the general genomic region in which the variation occurs, such as whether the variation is located in a known gene, whether there are known genes, gene homologs or regulatory regions nearby and the like.

Other information that may be included in the databases of the present invention include, but are not limited to, SNP sequence information, descriptive information concerning the clinical status of a tissue sample analyzed for SNP haplotype patterns, or the clinical status of the patient from which the sample was derived. The database may be designed to include different parts, for instance a variation database, a SNP database, a SNP haplotype block or SNP haplotype pattern database and an informative SNP database. Methods for the configuration and construction of databases are widely available, for instance, see Akerblom et al., (1999) U.S. Pat. No. 5,953,727, which is herein incorporated by reference in its entirety.

Figure 9:
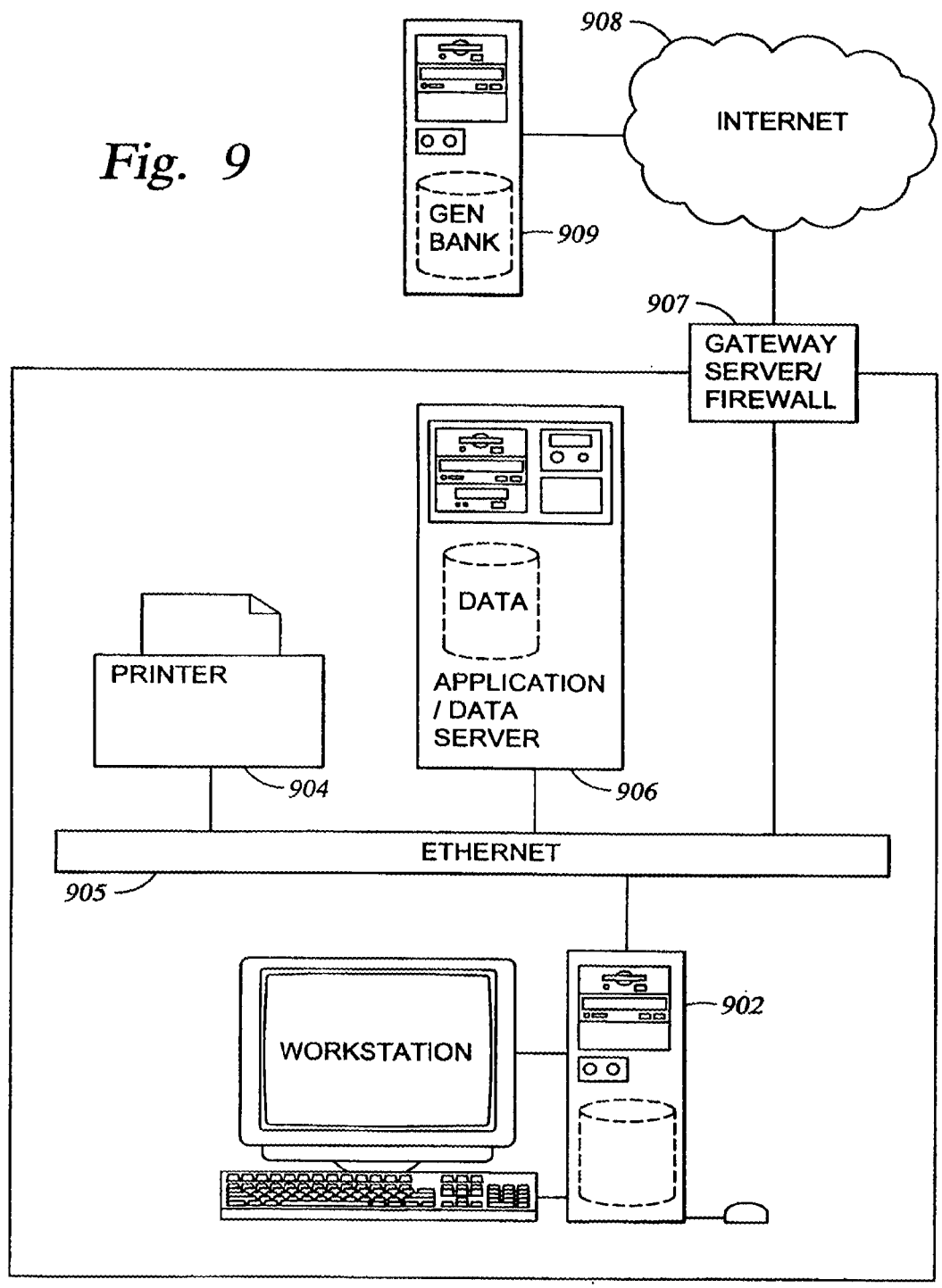
FIG. 9 shows an exemplary computer network system suitable for executing some embodiments of the present invention.

The databases of the invention may be linked to an outside or external database. FIG. 9 shows an exemplary computer network that is suitable for the databases and executing the software of the present invention. A computer workstation 902 is connected with the application/data server(s) 906 through a local area network (LAN), such as an ethernet 905. A printer 904 may be connected directly to the workstation or to the Ethernet 905. The LAN may be connected to a wide area network (WAN), such as the internet 908 via a gateway server 907 which may also serve as a firewall between the WAN 908 and the LAN 905. In preferred embodiments, the workstation may communicate with outside data sources, such as The SNP Consortium (TSC) or the National Center for Biotechnology Information 909, through the internet 908.

Any appropriate computer platform may be used to perform the necessary comparisons between SNP haplotype blocks or patterns, associated phenotypes, any other information in the database or information provided as an input. For example, a large number of computer workstations are available from a variety of manufacturers, such has those available from Silicon Graphics. Client-server environments, database servers and networks are also widely available and are appropriate platforms for the databases of the invention.

The databases of the invention may also be used to present information identifying the SNP haplotype pattern in an individual and such a presentation may be used to predict one or more phenotypic traits of the individual. Such methods may be used to predict the disease susceptibility/resistance and/or drug response of the individual. Further, the databases of the present invention may comprise information relating to the expression level of one or more of the genes associated with the variations of the invention.

The following examples describe specific embodiments of the present invention and the materials and methods are illustrative of the invention and are not intended to limit the scope of the invention.

Example 1

Preparation of Somatic Cell Hybrids

Standard procedures in somatic cell genetics were used to separate human DNA strands (chromosomes) from a diploid state to a haploid state. In this case, a diploid human lymphoblastoid cell line that was wildtype for the thymidine kinase gene was fused to a diploid hamster fibroblast cell line containing a mutation in the thymidine kinase gene. A sub-population of the resulting cells were hybrid cells containing human chromosomes. Hamster cell line A23 cells were pipetted into a centrifuge tube containing 10 ml DMEM in which 10% fetal bovine serum (FBS)+1× Pen/Strep+10% glutamine were added, centrifuged at 1500 rpm for 5 minutes, resuspended in 5 ml of RPMI and pipetted into a tissue culture flask containing 15 ml RPMI medium. The lymphoblastoid cells were grown at 37° C. to confluence. At the same time, human lymphoblastoid cells were pipetted into a centrifuge tube containing 10 ml RPMI in which 15% FBCS+1× Pen/Strep+10% glutamine were added, centrifuged at 1500 rpm for 5 minutes, resuspended in 5 ml of RPMI and pipetted into a tissue culture flask containing 15 ml RPMI. The lymphoblastoid cells were grown at 37° C. to confluence.

To prepare the A23 hamster cells, the growth medium was aspirated and the cells were rinsed with 10 ml PBS. The cells were then trypsinized with 2 ml of trypsin, divided onto 3-5 plates of fresh medium (DMEM without HAT) and incubated at 37° C. The lymphoblastoid cells were prepared by transferring the culture, into a centrifuge tube and centrifuging at 1500 rpm for 5 minutes, aspirating the growth medium, resuspending the cells in 5 ml RPMI and pipetting 1 to 3 ml of cells into 2 flasks containing 20 ml RPMI.

To achieve cell fusion, approximately 8-10×10$^6$ lymphoblastoid cells were centrifuged at 1500 rpm for 5 min. The cell pellet was then rinsed with DMEM by resuspending the cells, centrifuging them again and aspirating the DMEM. The lymphoblastoid cells were then resuspended in 5 ml fresh DMEM. The recipient A23 hamster cells had been grown to confluence and split 3-4 days before the fusion and were, at this point, 50-80% confluent. The old media was removed and the cells were rinsed three times with DMEM, trypsinized, and finally suspended in 5 ml DMEM. The lymphoblastoid cells were slowly pipetted over the recipient A23 cells and the combined culture was swirled slowly before incubating at 37° C. for 1 hour. After incubation, the media was gently aspirated from the A23 cells, and 2 ml room temperature PEG 1500 was added by touching the edge of the plate with a pipette and slowly adding PEG to the plate while rotating the plate with the other hand. It took approximately one minute to add all the PEG in one full rotation of the plate. Next, 8 ml DMEM was added down the edge of the plate while rotating the plate slowly. The PEG/DMEM mixture was aspirated gently from the cells and then 8 ml DMEM was used to rinse the cells. This DMEM was removed and 10 ml fresh DMEM was added and the cells were incubated for 30 min. at 37° C. Again the DMEM was aspirated from the cells and 10 ml DMEM in which 10% FBCS and 1× Pen/Strep were added, was added to the cells, which were then allowed to incubate overnight.

After incubation, the media was aspirated and the cells were rinsed with PBS. The cells were then trypsinized and divided among plates containing selection media (DMEM in which 10% FBS 1× Pen/Strep+1×HAT were added) so that each plate received approximately 100,000 cells. The media was changed on the third day following plating. Colonies were picked and placed into 24-well plates upon becoming visible to the naked eye (day 9-14). If a picked colony was confluent within 5 days, it was deemed healthy and the cells were trypsinized and moved to a 6-well plate.

DNA and stock hybrid cell cultures were prepared from the cells from the 6-well plate cultures. The cells were trypsinized and divided between a 100 mm plate containing 10 ml selection media and an Eppendorf tube. The cells in the tube were pelleted, resuspended 200 μl PBX and DNA was isolated using a Qiagen DNA mini kit at a concentration of <5 million cells per spin column. The 100 mm plate was grown to confluence, and the cells were either continued in culture or frozen.

Example 2

Selecting Haploid Hybrids

Scoring for the presence, absence and diploid/haploid state of human chromosomes in each hybrid was performed using the Affymetrix, HuSNP genechip (Affymetrix, Inc, of Santa Clara, Calif., HuSNP Mapping Assay, reagent kit and user manual, Affymetrix Part No 900194), which can score 1494 markers in a single chip hybridization. As controls, the hamster and human diploid lymphoblastoid cell lines were screened using the HuSNP chip hybridization assay. Any SNPs which were heterozygous in the parent lymphoblastoid diploid cell line were scored for haploidy in each fusion cell line. Assume that "A" and "B" are alternative variants at each SNP location. By comparing the markers that were present as "AB" heterozygous in the parent diploid cell line to the same markers present as "A" or "B" (hemizygous) in the hybrids, the human DNA strands which were in the haploid state in each hybrid line was determined.

FIG. 11 shows results after two human/hamster cell hybrids (Hybrid 1 and Hybrid 2) are tested for selected markers on human chromosome 21. The first column lists the HuSNP chip marker designations. The second column reports whether a signal was obtained when the hamster cell nucleic acid (no fusion) was used for hybridization with a HuSNP chip. As expected, there was no signal for any marker in the hamster cell sample. The third column reports which variants for each marker were detected ("A", "B" or "AB") in the diploid parent human lymphoblastoid cell line, CPD17. In some instances, only an A variant was present, in some instances only a B variant was present, and in some cases the CPD17 cells were heterozygous ("AB") for the variants. The last two columns report the result when nucleic acid samples from two human/hamster hybrids (Hybrid 1 and Hybrid 2) are hybridized with the HuSNP chip. Note in cases where only A variants were present in the parent CPD17 cell line, only A variants were transferred in the fusion. In cases where only B variants were present in the parent CPD17 cell line, only B variants were transferred in the fusion. In cases where the CPD17 cell line was heterozygous, an A variant was transferred to some fusion clones, and a B variant was transferred to other fusion clones. It should be understood, however, that often only portions of chromosomes are present in the hybrid cell lines resulting from this fusion process, that some hybrids may be diploid for some human chromosomes or portions thereof, that some hybrids may be haploid for other human chromosomes or portions thereof, and some hybrids may not have either variant of some chromosomes. Hybrids containing only one variant of a particular human chromosome (for instance, chromosome 21) were selected for analysis. Even more preferably, hybrids containing a whole chromosome (as opposed to only a portion thereof) were selected for analysis.

Example 3

Long Range PCR

DNA from the hamster/human cell hybrids was used to perform long-range PCR assays. Long range PCR assays are known generally in the art and have been described, for example, in the standard long range PCR protocol from the Boehringer Mannheim Expand Long Range PCR Kit, incorporated herein by reference or all purposes.

Primers used for the amplification reactions were designed in the following war a given sequence, for example the 23 megabase contig on chromosome 21, was entered into a software program known in the art herein called "repeat masker" which recognizes sequences that are repeated in the genome (e.g., Alu and Line elements)(see, A. F. A. Smit and P. Green, www.genome.washington.edu/uwgc/analysis-tools/repeatmask, incorporated herein by reference). The repeated sequences were "masked" by the program by substituting each specific nucleotide of the repeated sequence (A, T, G or C) with "N". The sequence output after this repeat mask substitution was then fed into a commercially available primer design program (Oligo 6.23) to select primers that were greater than 30 nucleotides in length and had melting temperatures of over 65° C. The designed primer output from Oligo 6.23 was then fed into a program which then "chose" primer pairs which would PCR amplify a given region of the genome but have minimal overlap with the adjacent PCR products. The success rate for long range PCR using commercially available protocols and this primer design was at least 80%, and greater than 95% success was achieved on some portions of human chromosomes.

An illustrative protocol for long range PCR uses the Expand Long Template PCR System from Boehringer Mannheim Cat #1681 834, 1681 842, or 1759 060. In the procedure each 50 µL PCR reaction requires two master mixes. In a specific example, Master Mix 1 was prepared for each reaction in 1.5 ml microfuge tubes on ice and includes a final volume of 19 µL of Molecular Biology Grade Water (Bio Whittaker, Cat. #16-001Y); 2.5 µL 10 mM dNTP set containing dATP, dCTP, dGTP, and dTTP at 10 mM each (Life Technologies Cat #10297-018) for a final concentration of 400 µM of each dNTP; and 50 ng DNA template.

Master Mix 2 for all reactions was prepared and kept on ice. For each PCR reaction Master Mix 2 includes a final volume of 25 µL of Molecular Biology Grade Water (Bio Whittaker); 5 µL 10×PCR buffer 3 containing 22.50 mM $MgCl_2$ (Sigma, Cat. #M 10289); 2.5 µL 10 mM $MgCl_2$ (for a final $MgCl_2$ concentration of 2.75 mM); and 0.75 µL enzyme mix (added last)

Six microliters of premixed primers (containing 2.5 µL of Master Mix 1) were added to appropriate tubes, then 25 µL of Master Mix 2 was added to each tube. The tubes were capped, mixed, centrifuged briefly and returned to ice. At this point, the PCR cycling was begun according to the following program step 1: 94° C. for 3 min to denature template; step 2: 94° C. for 30 sec; step 3: annealing for 30 sec at a temperature appropriate for the primers used; step 4: elongation at 68° C. for 1 min/kb of product; step 5: repetition of steps 2-4 38 times for a total of 39 cycles; step 6: 94° C. for 30 sec; step 7: annealing for 30 sec; step 8: elongation at 68° C. for 1 min/kb of product plus 5 additional minutes; and step 9: hold at 4° C. Alternatively, a two-step PCR would be performed: step 1: 94° C. for 3 min to denature template; step 2: 94° C. for 30 sec; step 3: annealing and elongation at 68° C. for 1 min/kb of product; step 4: repetition of steps 2-3 38 times for a total of 39 cycles; step 5:94° C. for 30 sec; step 6: annealing, and elongation at 68° C. for 1 min/kb of product plus 5 additional minutes; and step 7: hold at 4° C.

Results of the long range PCR amplification reaction for various regions on human chromosomes 14 and 22 were visualized on ethidium bromide-stained agarose gels (FIG. 12). The long range PCR amplification methods of the present invention routinely produced amplified fragments having an average size of about 8 kb, and appeared to fail to amplify genomic regions in only rare cases (see G11 on the chromosome 22 gel).

Example 4

Wafer Design, Manufacture, Hybridization and Scanning

The set of oligonucleotide probes to be contained on an oligonucleotide array (chip or wafer) was defined based on the human DNA strand sequence to be queried. The oligonucleotide sequences were based on consensus sequences reported in publicly available databases. Once the probe sequences were defined, computer algorithms were used to design photolithographic masks for use in manufacturing the probe-containing arrays. Arrays were manufactured by a light-directed chemical synthesis processes which combines solid-phase chemical synthesis with photolithographic fabrication techniques. See, for example, WO 92/10092, or U.S. Pat. Nos. 5,143,854; 5,384,261; 5,405,783; 5,412,087; 5,424,186; 5,445,934; 5,744,305; 5,800,992; 6,040,138; 6,040,193, all of which are incorporated herein by reference in their entireties for all purposes. Using a series of photolithographic masks to define exposure sites on the glass substrate (wafer) followed by specific chemical synthesis steps, the process constructed high-density areas of oligonucleotide probes on the array, with each probe in a predefined position. Multiple probe regions were synthesized simultaneously and in parallel.

The synthesis process involved selectively illuminating a photo-protected glass substrate by passing light through a photolithographic mask wherein chemical groups in unprotected areas were activated by the light. The selectively-activated substrate wafers were then incubated with a chosen nucleoside, and chemical coupling occurred at the activated positions on the wafer. Once coupling took place, a new mask pattern was applied and the coupling step was repeated with another chosen nucleoside. This process was repeated until the desired set of probes was obtained. In one specific example, 25-mer oligonucleotide probes were used, where the thirteenth base was the base to be queried. Four probes were used to interrogate each nucleotide present in each sequence—one probe complementary to the sequence and three mismatch probes identical to the complementary probe except for the thirteenth base. In some cases, at least $10 \times 10^6$ probes were present on each array.

Once fabricated, the arrays were hybridized to the products from the long range PCR reactions performed on the hamster-human cell hybrids. The samples to be analyzed were labeled and incubated with the arrays to allow hybridization of the sample to the probes on the wafer.

After hybridization, the array was inserted into a confocal, high performance scanner, where patterns of hybridization were detected. The hybridization data were collected as light emitted from fluorescent reporter groups already incorporated into the PCR products of the sample, which was bound to the probes. Sequences present in the sample that are complimentary to probes on the wafer hybridized to the wafer more strongly and produced stronger signals than those sequences that had mismatches. Since the sequence and position of each probe on the array was known, by complementarity, the identity of the variation in the sample nucleic acid applied to the probe array was identified. Scanners and scanning techniques used in the present invention are known to those skilled in the art and are disclosed in, e.g., U.S. Pat. No. 5,981,956 drawn to microarray chips, U.S. Pat. Nos. 6,262,838 and 5,459,325. U.S.S.N. In addition, 60/223,278 filed on Aug. 3, 2000, and non-provisional application claiming priority to U.S. Ser. No. 60/223,278 filed on Aug. 3, 2001, drawn to scanners and techniques for whole wafer scanning, are also incorporated herein by reference in their entireties for all purposes.

Example 5

Determination of SNP Haplotypes on Human Chromosome 21

Twenty independent copies of chromosome 21, representing African, Asian, and Caucasian chromosomes were analyzed for SNP discovery and haplotype structure. Two copies of chromosome 21 from each individual were physically separated using a rodent-human somatic cell hybrid technique (FIG. 10), discussed supra. The reference sequence for the analysis consisted of human chromosome 21 genomic DNA sequence consisting of 32,397,439 bases. This reference sequence was masked for repetitive sequences and the resulting 21,676,868 bases (67%) of unique sequence were assayed for variation with high density oligonucleotide arrays. Eight unique oligonucleotides, each 25 bases in length, were used to interrogate each of the unique sample chromosome 21 bases, for a total of $1.7 \times 10^8$ different oligonucleotides. These oligonucleotides were distributed over a total of eight different wafer designs using a previously described tiling strategy (Chee, et al., *Science* 274:610 (1996)). Light-directed chemical synthesis of oligonucleotides was carried out on 5 inch×5 inch glass wafers purchased from Affymetrix, Inc. (Santa Clara, Calif.).

Unique oligonucleotides were designed to generate 3253 minimally overlapping longe range PCR (LRPCR) products of 10 kb average length spanning 32.4 Mb of contiguous chromosome 21 DNA, and were prepared as described supra. For each wafer hybridization, corresponding LRPCR products were pooled and were purified using Qiagen tip 500 (Qiagen). A total of 280 µg of purified DNA was fragmented using 37 µl of 10× One-Phor-All buffer PLUS (Promega) and 1 unit of DNAase (Life Technologies/Invitrogen) in 370 µl total volume at 37° C. for 10 min followed by heat inactivation at 99° C. for 10 min. The fragmented products were end labeled using 500 units of Tdt (Boehringer Manheim) and 20 nmoles of biotin-N6-ddATP (DuPont NEN) at 37° C. for 90 min and heat inactivated at 95° C. for 10 min. The labeled samples were hybridized to the wafers in 10 mM Tris-HCL (pH 8), 3M Tetramethylammonium chloride, 0.01% Tx-100, 10 µg/ml denatured herring sperm DNA in a total volume of 14 ml per wafer at 50° C. for 14-16 hours. The wafers were rinsed briefly in 4×SSPE, washed three times in 6×SSPE for 10 mM each, stained using streptavidin R-phycoerythrin (SAPE, 5 ng/ml) at room temp for 10 min. The signal was amplified by staining with an antibody against streptavidin (1.25 ng/ml) and by repeating the staining step with SAPE.

PCR products corresponding to the bases present on a single wafer were pooled and hybridized to the wafer as a single reaction. In total, $3.4 \times 10^9$ oligonucleotides were synthesized on 160 wafers to scan 20 independent copies of human chromosome 21 for DNA sequence variation. Each unique chromosome 21 was amplified from a rodent-human hybrid cell line by using long range PCR. LRPCR assays were designed using Oligo 6.23 primer design software with high-moderate stringency parameters. The resulting primers were typically 30 nucleotides in length with the melting temperature of >65° C. The range of amplicon size was from 3 kb-14 kb. A primer database for the entire chromosome was generated and software (pPicker) was utilized to choose a minimal set of non-redundant primers that yield maximum coverage of chromosome 21 sequence with a minimal overlap between adjacent amplicons. Alternatively, the primer selection method described in Example 3, herein, was employed. LRPCR reactions were performed using the Expand Long Template PCR Kit (Boehringer Mannheim) with minor modifications. The wafers were scanned using a custom built confocal scanner.

SNPs were detected as altered hybridization by using a pattern recognition algorithm. A combination of previously described algorithms (Wang, et al., *Science* 280:1077 (1998)), was used to detect SNPs based on altered hybridization patterns. In total, 35,989 SNPs were identified in the sample of twenty chromosomes. The position and sequence of these human polymorphisms have been deposited in GenBank's SNPdb. Dideoxy sequencing was used to assess a random sample of 227 of these SNPs in the original DNA samples, confirming 220 (97%) of the SNPs assayed. In order to achieve this low rate of 3% false positive SNPs, stringent thresholds were required for SNP detection on wafers that resulted in a high false negative rate. Approximately 65% of all bases present on the wafers yielded data of high enough quality for use in SNP detection with 35% being discarded as being false negatives. Consistent failure of long range PCR in all samples analyzed accounts for 15% of the 35% false negative rate. The remaining 20% false negatives are distributed between bases that never yield high quality data (10%) and bases that yield high quality data in only a fraction of the 20 chromosomes analyzed (10%). In general, it is the sequence context of a base that dictates whether or not it will yield high quality data. The finding that approximately 20% of all bases give consistently poor data is very similar to the finding that approximately 30% of bases in single dideoxy sequencing reads of 500 bases have quality scores too low for reliable SNP detection (Altschuler, et al., *Nature* 407:513 (2000)). The power to discover rare SNPs as compared to more frequent SNPs is disproportionately reduced m cases where only a limited number of the samples analyzed yield high quality data for a given base. As a result, SNP discovery by this method is biased in favor of common SNPs.

Figure 13A:
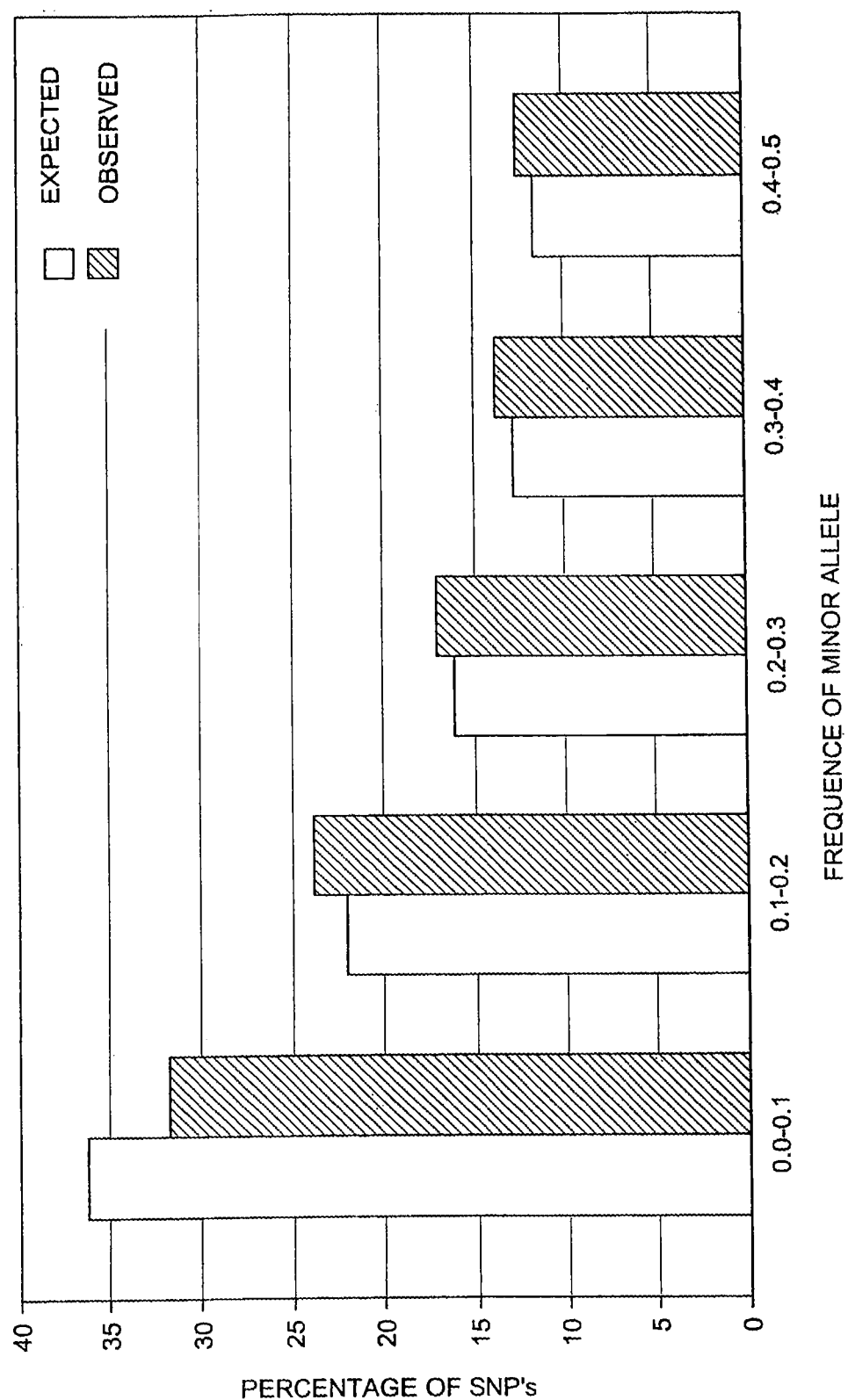
FIG. 13A is a bar graph showing the percentage of SNPs plotted against the frequency of the minor allele (variant) of the SNP.
Figure 13B:
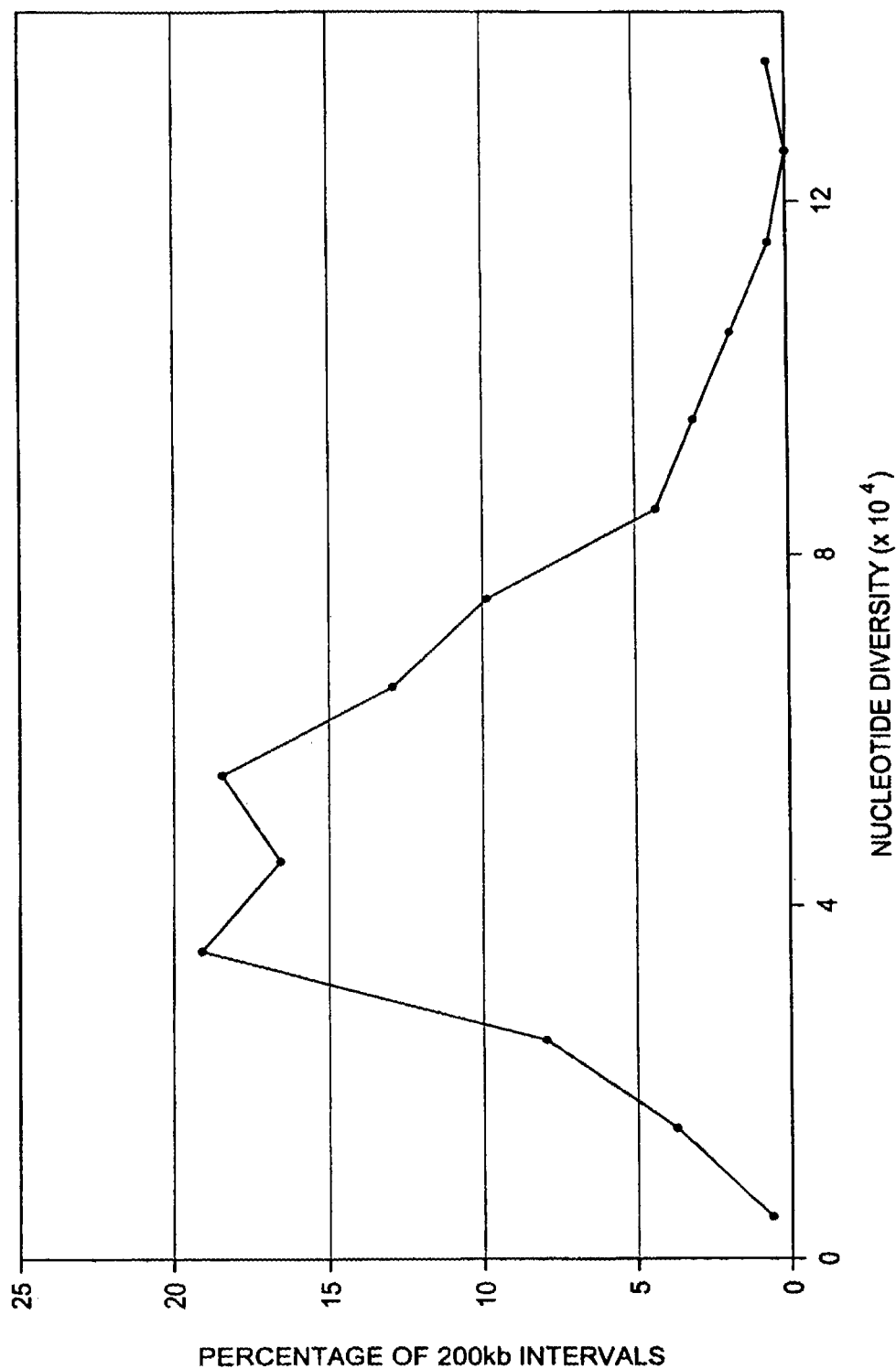
FIG. 13B is a graph of the percentage of 200 kb intervals as a function of the nucleotide diversity in the interval.

FIG. 13A shows the distribution of minor allele frequencies of all 35,989 SNPs discovered m the sample of globally diverse chromosomes. Genetic variation, normalized for the number of chromosomes in the sample, was estimated with two measures of nucleotide diversity it the average heterozygosity per site and θ the population mutation parameter (see Hartl and Clark, *Principles of Population Genetics* (Sinauer, Mass., 1997)). The 32,397,439 bases of finished genomic chromosome 21 DNA were divided into 200,000 base pair segments, and the high-quality base pairs used for SNP discovery in each segment were examined. The observed heterozygosity of these bases was used to calculate an average nucleotide diversity (π) for each segment. The estimates of average nucleotide diversity for the total data set (π=0.000723 and θ=0.000798), as well as, the distribution of nucleotide diversity, measured in contiguous 200,000 base pair bins of chromosome 21 (FIG. 13B), are within the range of values previously described (The International SNP Map Working Group, *Nature* 409:928-33 (2001)).

The extent of overlap of 15,549 chromosome 21 SNPs discovered by The SNP Consortium (TSC) was compared with the SNPs found in this study. Of the TSC SNPs, 5,087 were found to be in repeated DNA and were not tiled on the wafers. Of the remaining 10,462 TSC SNPs, 4705 (45%) were identified. The estimate of θ was observed to be greater than the estimate of π for 129 of the 162 200-kb bins of contiguous DNA sequence analyzed. This difference is consistent with a recent expansion of the human population and is similar to the finding of a recent study of nucleotide diversity in human genes (Stephens, et al., *Science* 293:489 (2001)). It was found that 11,603 of the SNPs (32%) had a minor allele observed a single time in the sample (singletons), as compared with the neutral model expectation of 43% singletons given the observed amount of nucleotide diversity (Fu and Li, *Genetics* 133:693 (1993)). The difference between the observed and expected values is likely attributable to the reduced power to identify rare as compared to common SNPs in this study as discussed above.

Over all, 47% of the 53,000 common SNPs with an allele frequency of 10% or greater estimated to be present in 32.4 Mb of the human genome were identified. This compares with an estimate of 18-20% of all such common SNPs present in the collection generated by the International SNP Mapping Working Group and the SNP Consortium. The difference in coverage is explained by the fact that the present study used larger numbers of chromosomes for SNP discovery. To assess the replicability of the findings, SNP discovery was performed for one wafer design with nineteen additional copies of chromosome 21 derived from the same diversity panel as the original set of samples. A total of 7188 SNPs were identified using the two sets of samples. On average, 66% of all SNPs found in one set of samples were discovered in the second set, consistent with previous findings (Marth, et al., *Nature Genet.* 27:371 (2001) and Yang, et al., *Nature Genet.* 26:13 (2000)). As expected, failure of a SNP to replicate in a second set of samples is strongly dependent on allele frequency. It was found that 80% of SNPs with a minor allele present two or more times in a set of samples were also found in a second set of samples, while only 32% of SNPs with, a minor allele present a single time were found in a second set of samples. These findings suggest that the 24,047 SNPs in the collection with a minor allele represented more than once are highly replicable in different global samples and that this set of SNPs is useful for defining common global haplotypes. In the course of SNP discovery, 339 SNPs which appeared to have more than two alleles were identified. These SNPs were not included in the present analysis.

Figure 13C:
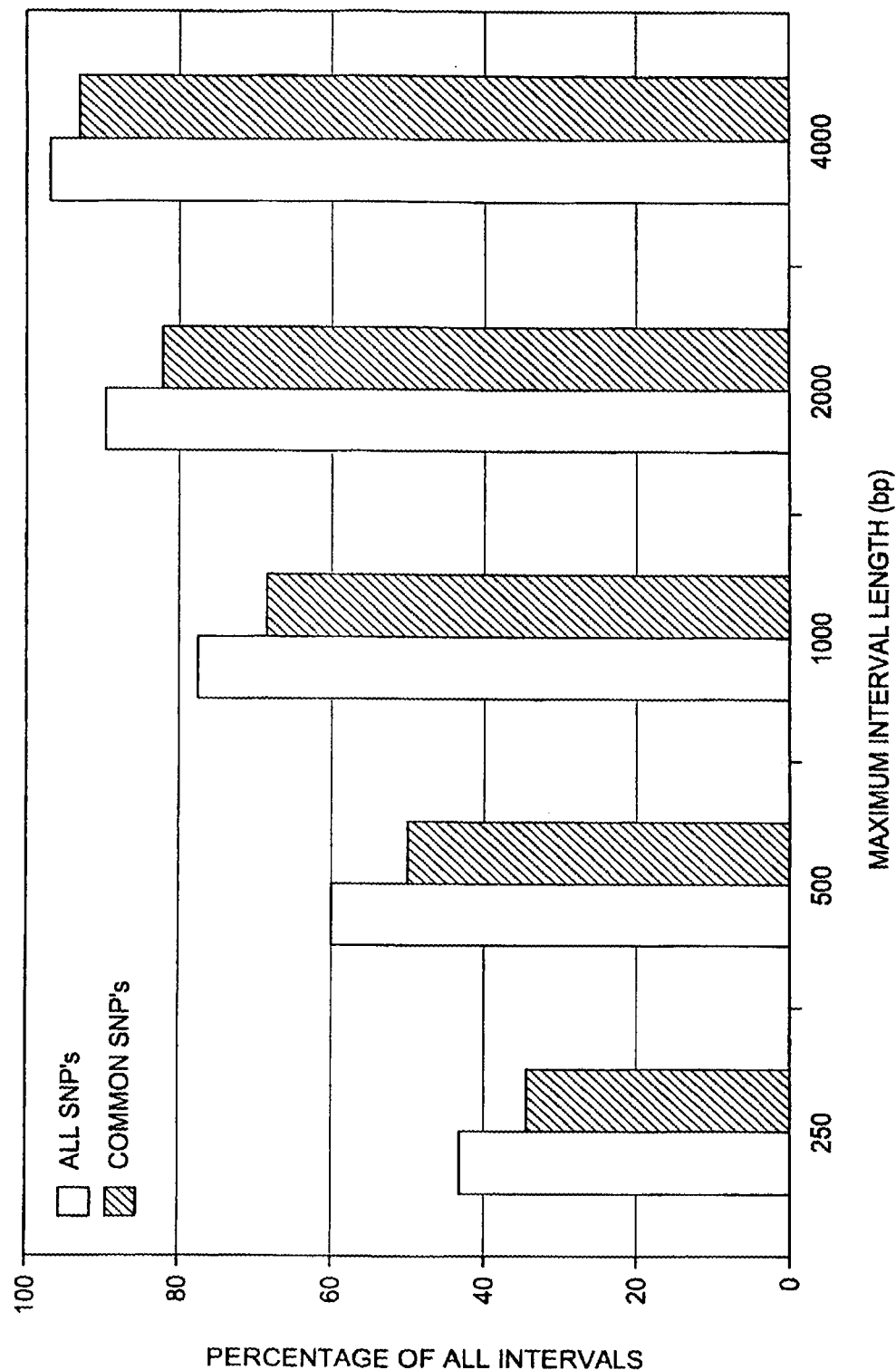
FIG. 13C is a bar graph showing the percentage of all intervals plotted against interval length.

In addition to the replicability of SNPs in different samples, the distance between consecutive SNPs in a collection of SNPs is critical for defining meaningful haplotype structure. Haplotype blocks, which can be as short as several kb, may go unrecognized if the distance between consecutive SNPs in a collection is large relative to the size of the actual haplotype blocks. The collection of SNPs in this study was very evenly distributed across the chromosome, even though repeat sequences were not included in the SNP discovery process. FIG. 13C shows the distribution of SNP coverage across 32,397,439 bases of finished chromosome 21 DNA sequence. An interval is the distance between consecutive SNPs. There are a total of 35,988 intervals for the entire SNP set and a total of 24,046 intervals for the common SNP set (i.e. SNPs with a minor allele present more than once in the sample). The average distance between consecutive SNPs was 900 bases when all SNPs are considered, and 1300 bases when only the 24,047 common SNPs were considered. For this set of common SNPs, 93% of intervals between consecutive SNPs m genomic DNA, including repeated DNA, were 4000 bases or less (again, see FIG. 13C).

The construction of haplotype blocks or patterns from diploid data is complicated by the fact that the relationship between alleles for any two heterozygous SNPs is not directly observable. Consider an individual with two copies of chromosome 21 and two alleles, A and G, at one chromosome 21 SNP, as well as two alleles, A and G, at a second chromosome 21 SNP. In such a case, it is, unclear if one copy of chromosome 21 contains allele A at the first SNP and allele A at the second SNP, while the other copy of chromosome 21 contains allele G at the first SNP and allele G at the second SNP, or if one copy of chromosome 21 contains allele A at the first SNP and allele G at the second SNP, while the other copy of chromosome 21 contains allele G at the first SNP and allele A at the second SNP. Current methods used to circumvent this problem include statistical estimation of haplotype frequencies, direct inference from family data, and allele-specific PCR amplification over short segments.

Figure 14:
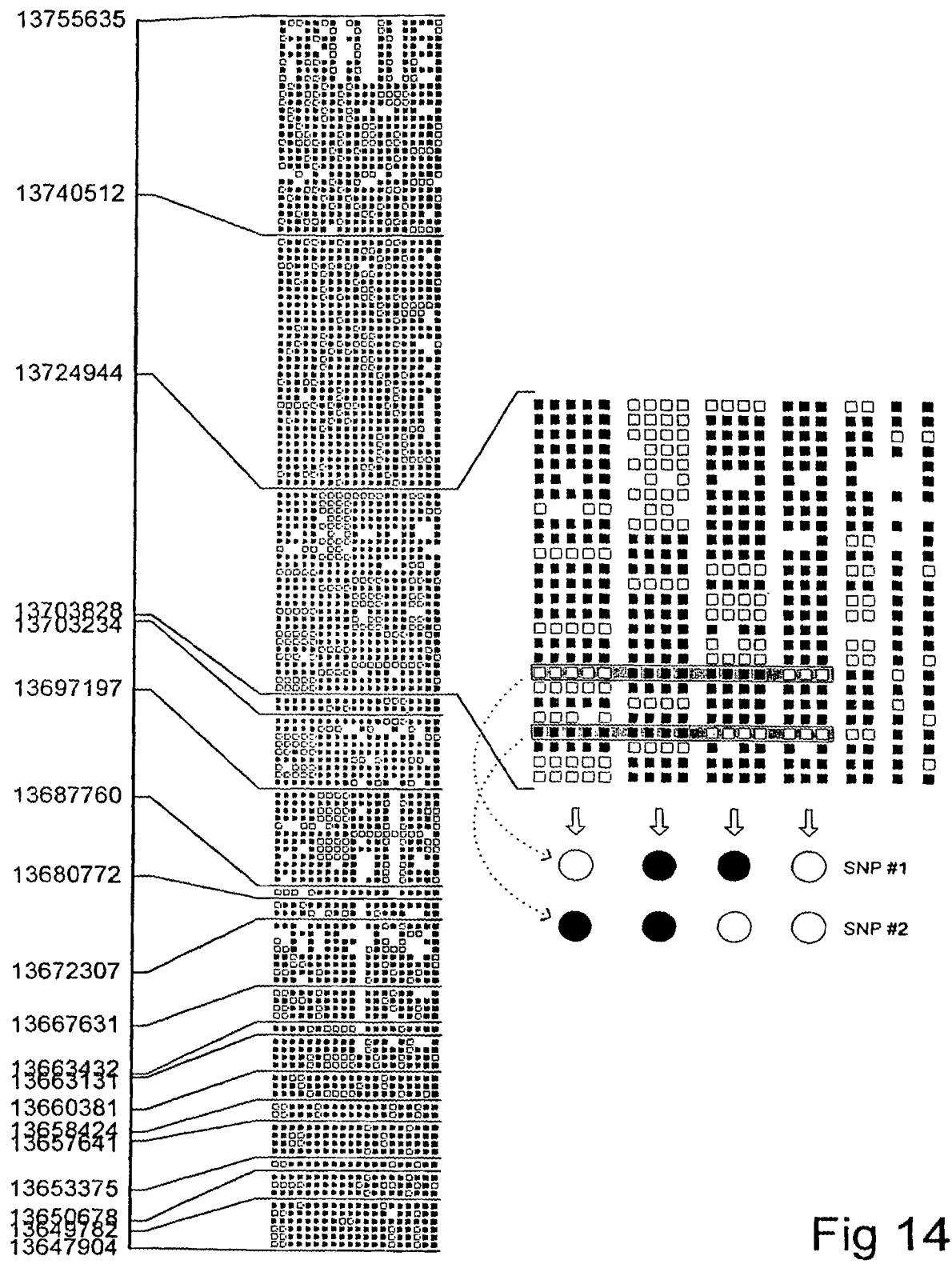
FIG. 14 shows the haplotype patterns for twenty independent globally diverse chromosomes defined by 147 common human chromosome 21 SNPs.

To avoid these complexities, the present invention characterized SNPs on haploid copies of chromosome 21 isolated in rodent-human somatic cell hybrids were characterized, allowing direct determination of the full haplotypes of these chromosomes. The set of 24,047 SNPs with a minor allele represented more than once in the data set was used to define the haplotype structure are shown in FIG. 14. The haplotype patterns for twenty independent globally diverse chromosomes defined by 147 common human chromosome 21 SNPs is shown. The 147 SNPs span 106 kb of genomic DNA sequence. Each row of colored boxes represents a single SNP. The black boxes in each row represent the major allele for that SNP, and the white boxes represent the minor allele. Absence of a box at any position in a row indicates missing data. Each column of colored boxes represents a single chromosome, with the SNPs arranged in their physical order on the chromosome. Invariant bases between consecutive SNPs are not represented in the figure. The 147 SNPs are divided into eighteen blocks, defined by black horizontal lines. The position of the base in chromosome 21 genomic DNA sequence defining the beginning of one block and the end of the adjacent block is indicated by the numbers to the left of the vertical black line. The expanded boxes on the right of the figure represent a SNP block defined by 26 common SNPs spanning 19 kb of genomic DNA. Of the seven different haplotype patterns represented in the sample, the four most common patterns include sixteen of the twenty chromosomes sampled (i.e. 80% of the sample). The black and white circles indicate the allele patterns of two informative SNPs, which unambiguously distinguish between the four common haplotypes in this block. Although no two chromosomes shared an identical haplotype pattern for these 147 SNPs, there are numerous regions in which multiple chromosomes shared a common pattern. One such region, defined by 26 SNPs spanning 19 kb, is expanded for more detailed analysis (again, see the enlarged region of FIG. 14). This block defines seven unique haplotype patterns in 20 chromosomes. Despite the fact that some data is missing due to failure to pass the threshold for data quality, in all cases a given chromosome can be assigned unambiguously to one of the seven haplotypes. The four most frequent haplotypes, each of which is represented by three or more chromosomes, account for 80% of all chromosomes in the sample. Only two "informative" SNPs out of the total of twenty-six are required to distinguish the four most frequent haplotypes from one another. In this example, four chromosomes with infrequent haplotypes would be incorrectly classified as common haplotypes by using information from only these two informative SNPs. Nevertheless, it is remarkable that 80% of the haplotype structure of the entire global sample is defined by less than 10% of the total SNPs in the block. Several different possibilities exist in which three informative SNPs can be chosen so that each of the four common haplotypes is defined uniquely by a single SNP. One of these "three SNP" choices would be preferred over the two SNP combination in an experiment involving genotyping of pooled samples, since the two SNP combination would not permit determination of frequencies of the four common haplotypes in such a situation; thus, the present invention provides a dramatic improvement over the random selection method of SNP mapping.

In summary, while the particular application may dictate the selection of informative SNPs to capture haplotype information, it is clear that the majority of the haplotype information in the sample is contained in a very small subset of all the SNPs. It is also clear that random selection of two or three informative SNPs from this block of SNPs will often not provide enough information to uniquely assign a chromosome to one of the four common haplotypes.

One issue is how to define a set of contiguous blocks of SNPs spanning the entire 32.4 Mb of chromosome 21 while minimizing the total number of SNPs required to define the haplotype structure. In one embodiment, an optimization algorithm based on a "greedy" strategy was used to address this problem. All possible blocks of physically consecutive SNPs of size one SNP or larger were considered. Ambiguous haplotype patterns were treated as missing data and were not included when calculating percent coverage. Considering the remaining overlapping blocks simultaneously, the block with the maximum ratio of total SNPs in the block to the minimal number of SNPs required to uniquely discriminate haplotypes represented more than once in the block was selected. Any of the remaining blocks that physically overlapped with the selected block were discarded, and the process was repeated until a set of contiguous, non-overlapping blocks that cover the 32.4 Mb of chromosome 21 with no gaps, and with every SNP assigned to a block, was selected. Given the sample size of twenty chromosomes, the algorithm produces a maximum of ten common haplotype patterns per block, each represented by two independent chromosomes.

Applying this algorithm to the data set of 24,047 common SNPs, 4135 blocks of SNPs spanning chromosome 21 were defined. A total of 589 blocks, comprising 14% of all blocks, contain greater than ten SNPs per block and include 44% of the total 32.4 Mb. In contrast, 2138 blocks, comprising 52% of all blocks, contain less than three SNPs per block and make up only 20% of the physical length of the chromosome. The largest block contains 114 common SNPs and spans 115 kb of genomic DNA. Overall, the average physical size of a block is 7.8 kb. The size of a block is not correlated with its order on the chromosome, and large blocks are interspersed with small blocks along the length of the chromosome. There are an average of 2.7 common haplotype patterns per block, defined as haplotype patterns that are observed on multiple chromosomes. On average, the most frequent haplotype pattern in a block is represented by 9.6 chromosomes out of the twenty chromosomes in the sample, the second most frequent haplotype pattern is represented by 4.2 chromosomes, and the third most frequent haplotype patterns, if present, is represented by 2.1 chromosomes. The fact that such a large fraction of globally diverse chromosomes are represented by such limited haplotype diversity is remarkable. The findings are consistent with the observation that when haplotype pattern frequency is considered, 82% of the haplotype patterns observed in a collection of 313 human genes are observed in all ethnic groups, while only 8% of haplotypes are population specific (Stephens, et al., *Science* 293:489-93 (2001)).

Several experiments were performed to measure the influence of parameters of the haplotype algorithm on the resulting block patterns. The fraction of chromosomes required to be covered by common haplotypes was varied, from an initial 80%, to 70% and 90%. As would be expected, requiring more complete coverage results in somewhat larger numbers of shorter blocks. Using only the 16,503 SNPs with a minor allele frequency of at least 20% in the sample resulted in somewhat longer blocks, but the numbers of SNPs per block did not change significantly. For one region of about 3 Mb, a deeper sample of 38 chromosomes for SNPs and common haplotype blocks with at least 10% frequency was analyzed, so as to be comparable with the 20 chromosome analysis. The resulting distribution of block sizes closely matched the initial results. Also, a randomization test was performed in which the non-ambiguous alleles at each SNP were permuted, and then used for haplotype block discovery. In this analysis, 94% of blocks contained fewer than three SNPs, and only one block contained more than five SNPs. This confirms that the larger blocks seen in the data cannot be produced by chance associations or as artifacts of the block selection methods of the present invention.

In an effort to determine if genes were proportionately represented in both large and small blocks, a determination was made of the number of exonic bases in blocks containing more than 10 SNPs, 3 to 10 SNPs, and less than 3 SNPs. Exonic bases are somewhat over-represented as compared to total bases in blocks containing 3 to 10 SNPs (p<0.05 as determined by a permutation test).

Figure 15:
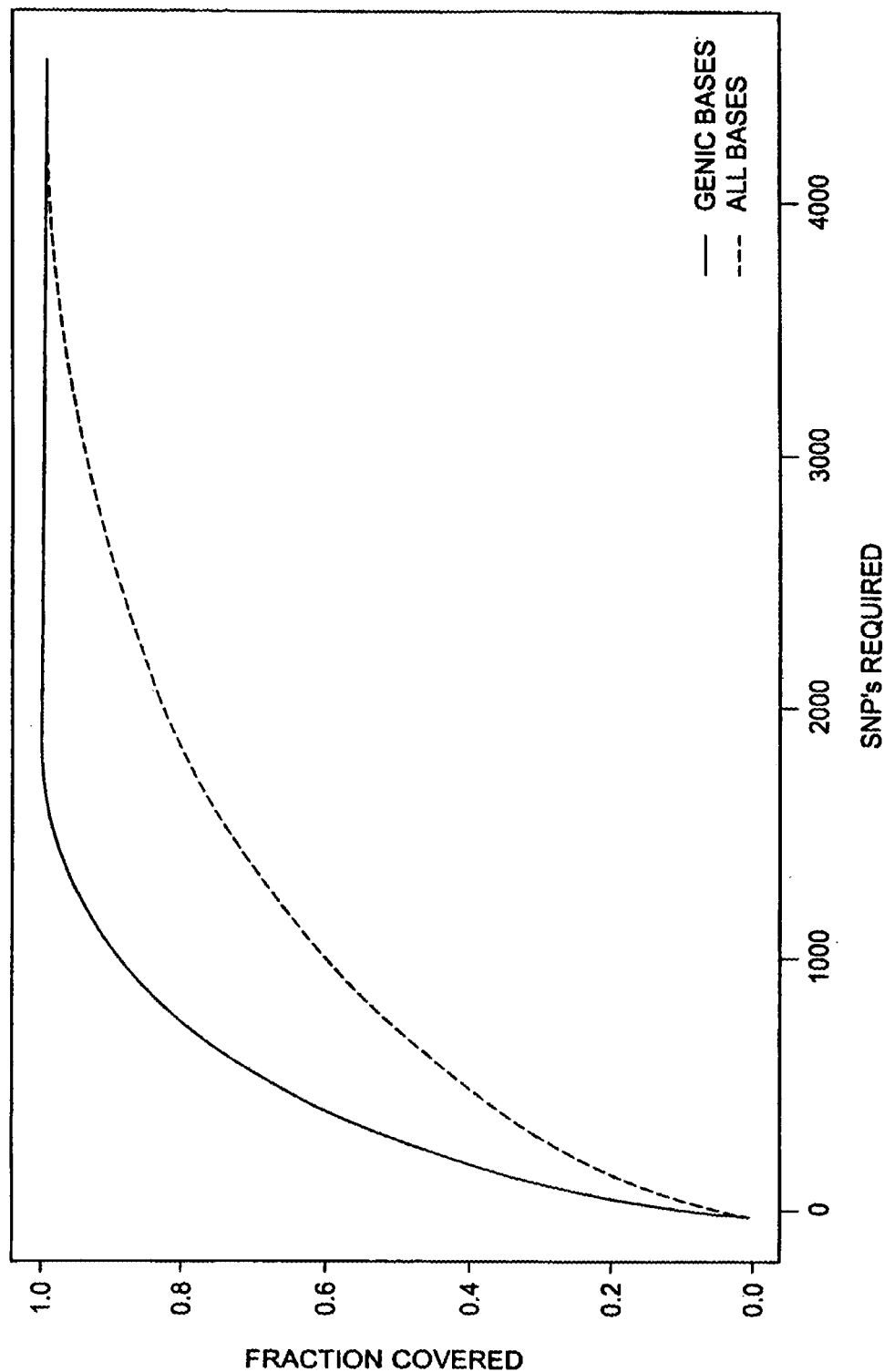
FIG. 15 is a plot of the fraction of chromosome covered as a function of the number of SNPs required for that coverage.

Based on knowledge of the haplotype structure within blocks, subsets of the 24,047 common SNPs can be selected to capture any desired fraction of the common haplotype information, defined as complete information for haplotypes present more than once and including greater than 80% of the sample across the entire 32.4 Mb. FIG. 15 shows the number of SNPs required to capture the common haplotype information for 32.4 Mb of chromosome 21. For each SNP block, the minimum number of SNPs required to unambiguously distinguish haplotypes in that block that are present more than once (i.e., common haplotype information) was determined. These SNPs provide common haplotype information for the fraction of the total physical distance defined by that block. Beginning with the SNPs that provide common haplotype information for the greatest physical distance, the cumulative increase in physical coverage (i.e., fraction covered) is plotted relative to the number of SNPs added (i.e., SNPs required). Genic DNA includes all genomic DNA beginning 10 kb 5' of the first exon of each known chromosome 21 gene and extending 10 kb 3' of the last exon of that gene. For example, while a minimum of 4563 SNPs are required to capture all the common haplotype information, only 2793 SNPs are required to capture the common haplotype information in blocks containing three or more SNPs that cover 81% of the 32.4 Mb. A total of 1794 SNPs are required to capture all the common haplotype information in genic DNA, representing approximately two hundred and twenty distinct genes.

The present invention has particular relevance for whole-genome association studies mapping phenotypes such as common disease genes. This approach relies on the hypothesis that common genetic variants are responsible for susceptibility to common diseases (Risch and Merikangas, *Science* 273:1516 (1996), Lander, *Science* 274:536 (1996)). By comparing the frequency of genetic variants in unrelated cases and controls, genetic association studies can identify specific haplotypes in the human genome that play important roles in disease. While this approach has been used to successfully associate single candidate genes with disease (Altschuler, et al., *Nature Genet.* 26:76 (2000)), the recent availability of the human DNA sequence offers the possibility of surveying the entire genome, dramatically increasing the power of genetic association analysis (Kruglyak, *Nature Genet* 22:139 (1999)). A major limitation to, the implementation of this method has been lack of knowledge of the haplotype structure of the human genome, which is required in order to select the appropriate genetic variants for analysis. The present invention demonstrates that high-density oligonucleotide arrays in combination with somatic cell genetic sample preparation provide a high-resolution approach to empirically define the common haplotype structure of the human genome.

Although the length of genomic regions with a simple haplotype structure is extremely variable, a dense set of common SNPs enables the systematic approach to define blocks of the human genome in which 80% of the global human population is described by only three common haplotypes. In general, when applying the particular algorithm used in this embodiment, the most common haplotype in any block is found in 50% of individuals, the second most common in 25% of individuals, and the third most common in 12.5% of individuals. It is important to note that blocks are defined based on their genetic information content and not on knowledge of how this information originated or why it exists. As such, blocks do not have absolute boundaries, and may be defined in different ways, depending on the specific application. The algorithm in this embodiment provides only one of many possible approaches. The results indicate that a very dense set of SNPs is required to capture all the common haplotype information. Once in hand, however, this information can be used to identify much smaller subsets of SNPs useful for comprehensive whole-genome association studies.

Those skilled in the art will appreciate readily that the techniques applied to human chromosome 21 can be applied to all the chromosomes present in the human genome. In a preferred embodiment of the present invention, multiple whole genomes of a diverse population representative of the human species are used to identify SNP haplotype blocks common to all or most members of the species. In some embodiments, SNP haplotype blocks are based on ancient SNPs by excluding SNPs that are represented at low frequency. The ancient SNPs are likely to be important as they have been preserved in the genome because they impart some selective benefit to organisms carrying them.

Example 6

Using Associated Genes for Gene Therapy and Drug Discovery

One example for using the methods of the present invention is outlined in this prophetic example. SNP discovery is performed on twenty haploid genomes, and fifty haploid genomes are analyzed by the methods of the present invention to determine SNP haplotype blocks, SNP haplotype patterns, informative SNPs and minor allele frequency for each informative SNP. These fifty haploid genomes comprise the control genomes of the present study (see step 1300 of FIG. 13).

Next, genomic DNA from 500 individuals having an obesity phenotype are assayed for variants by using long distance PCR and microarrays as described supra (see also, U.S. Pat. No. 6,300,063 issued to Lipshutz, et al., and U.S. Pat. No. 5,837,832 to Chee, et al.), and the frequency of the minor allele for each informative SNP is determined for this clinical population (see step 1310 of FIG. 13). The minor allele frequencies of the informative SNPs for the two populations are compared, and the control and clinical populations are determined to have statistically significant differences in three informative SNP locations (steps 1320 and 1330). The SNP location with the largest difference in the minor allele frequency between the control and clinical populations is selected for analysis.

The informative location selected is contained within a SNP haplotype block that is found to span 1 kb of noncoding sequence 5' of the coding region and 4 kb of the coding region of the leptin gene (step 1340). Analysis of the variations contained within this region indicates that a G at one SNP position in this region is responsible for destruction of the promoter for the leptin gene, with a commensurate lack of expression of the leptin protein.

Fibroblasts are obtained from a subject by skin biopsy. The resulting tissue is placed in tissue-culture medium and separated into small pieces. Small pieces of the tissue are placed on the bottom of a wet surface of a tissue culture flask with medium. After 24 hours at room temperature, fresh media is added (e.g., Ham's F12 media, with 10% FBS, penicillin and streptomycin). The tissue is then incubated at 37° C. for approximately one week. At this time, fresh media is added and subsequently changed every several days. After an additional two weeks in culture, a monolayer of fibroblasts emerges. The monolayer is trypsinized and scaled into larger flasks.

The vector derived from the Moloney murine leukemia virus, which contains a kanamycin resistance gene, is digested with restriction enzymes for cloning a fragment to be expressed. The digested vector is treated with calf intestinal phosphatase to prevent self-ligation. The dephosphorylated, linear vector is fractionated on an agarose gel and purified. Leptin cDNA, capable of expressing active leptin protein product, is isolated. The ends of the fragment are modified, if necessary, for cloning into the vector. Equal molar quantities of the Moloney murine leukemia virus linear backbone and the leptin gene fragment are mixed together and joined using T4 DNA ligase. The ligation mixture is used to transform E. coli and the bacteria are then plated onto agar-containing kanamycin. Kanamycin phenotype and restriction analysis confirm that the vector has the properly inserted leptin gene.

Packaging cells are grown in tissue culture to confluent density in Dulbecco's Modified Eagles Medium (DMEM) with 10% calf serum, penicillin and streptomycin. The vector containing the leptin gene is introduced into the packaging cells by standard techniques. Fresh media is added to the packaging cells, and after an appropriate incubation period, media is harvested from the plates of confluent packaging cells. The media, containing the infectious viral particles, is filtered through a Millipore filter to remove detached packaging cells, then is used to infect fibroblast cells. Media is removed from a sub-confluent plate of fibroblasts and quickly replaced with the filtered media. Polybrene (Aldrich) may be included in the media to facilitate transduction. After appropriate incubation, the media is removed and replaced with fresh media. If the titer of virus is high, then virtually, all fibroblasts will be infected and no selection is required. If the titer is low, then it is necessary to use a retroviral vector that has a selectable marker, such as neo or his, to select out transduced cells for expansion.

Engineered fibroblasts then are introduced into individuals, either alone or after having been grown to confluence on microcarrier beads, such as cytodex 3 beads. The injected fibroblasts produce leptin product, and the biological actions of the protein are conveyed to the host.

Alternatively or in addition, the leptin gene is isolated, cloned into an expression vector and employed for producing leptin polypeptides. The expression vector contains suitable transcriptional and translational initiation regions, and transcriptional and translational termination regions, as disclosed supra. Isolated leptin protein can be produced in this manner and used to identify agents which bind it; alternatively cells expressing the engineered leptin gene and protein are used in assays to identify agents. Such agents are identified by, for example, contacting a candidate agent with an isolated leptin polypeptide for a time sufficient to form a polypeptide/compound complex, and detecting the complex. If a polypeptide/compound complex is detected, the compound that binds to the leptin polypeptide is identified. Agents identified via this method can include compounds that modulate activity of leptin. Agents screened in this manner are peptides, carbohydrates, vitamin derivatives, and other small molecules or pharmaceutical agents. In addition to biological assays to identify agents, agents may be pre-screened by choosing candidate agents selected by using protein modeling techniques, based on the configuration of the leptin protein.

In addition to identifying agents that bind the leptin protein, sequence-specific or element-specific agents that control gene expression through binding to the leptin gene are also identified. One class of nucleic acid binding agents are agents that contain base residues that hybridize to leptin mRNA to block translation (e.g., antisense oligonucleotides). Another class of nucleic acid binding agents are those that form a triple helix with DNA to block transcription (triplex oligonucleotides). Such agents usually contain 20 to 40 bases, are based on the classic phosphodiester, ribonucleic acid backbone, or can be a variety of sulfhydryl or polymeric derivatives that have base attachment capacity.

Additionally, allele-specific oligonucleotides that hybridize specifically to the leptin gene and/or agents that bind specifically to the variant leptin protein (e.g., a variant-specific antibody) can be used as diagnostic agents. Methods for preparing and using allele-specific oligonucleotides and for preparing antibodies are described supra and are known in the art.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

The present invention provides greatly improved methods for conducting genome-wide association studies by identifying individual variations, determining SNP haplotype blocks, determining haplotype patterns and, further, using the SNP haplotype patterns to identify informative SNPs. The informative SNPs may be used to dissect the genetic bases of disease and drug response in a practical and cost effective manner unknown previously. It is to be understood that the above description is intended to be illustrative and not restrictive. Many embodiments will be apparent to those skilled in the art upon reviewing the above description. The scope of the invention should, therefore, be determined not with reference to the above description, but should instead be determined with reference to the appended claims, along with the full scope of equivalents to which such claims are entitled.

What is claimed is:

1. A system for genomic analysis to determine pharmacogenomic-related genetic loci without a priori knowledge of the location of said loci, the system comprising:
   one or more databases that store information obtained from genotyping genomic DNA of individuals in a case population which comprises individuals who exhibit a response to a drug to determine frequency of one or more informative genetic variations in the case population and information obtained from genotyping genomic DNA of individuals in a control population which comprises individuals who do not exhibit the response to the drug to determine frequency of one or more informative genetic variations in the control population, wherein the one or more informative genetic variations distinguish one haplotype pattern from other haplotype patterns of a haplotype block;
   a server comprising:
      one or more processors; and
      a computer memory comprising processor-executable instructions that, when executed by the one or more processors, cause the one or more processors to perform the following:
      access the one or more databases;
      compare frequencies of the one or more informative genetic variations between the case population and the control population;
      select the one or more informative genetic variations which have a frequency in the case population which is significantly different to the control population as pharmacogenomic-related genetic loci; and
      provide a report to a client device in communication with the server across a communications network, wherein the report includes a description of the one or more informative genetic variations which have a frequency in the case population which is significantly different to the frequency in the control population as pharmacogenomic-related genetic loci.

2. The system of claim 1, wherein the one or more processors are configured to receive a request for the report from the client device.

3. The system of claim 1, wherein the one or more informative genetic variations are single-nucleotide polymorphisms.

4. A computer-implemented method of genomic analysis, the method implemented by a server in communication with a client device across a communications network, the server comprising one or more processors, the method comprising:
   accessing, by the one or more processors, one or more databases that store information obtained from genotyping genomic DNA of individuals in a case population which comprises individuals who exhibit a response to a drug to determine frequency of one or more informative genetic variations in the case population and information obtained from genotyping genomic DNA of individuals in a control population which comprises individuals who do not exhibit the response to the drug to determine frequency of one or more informative genetic variations in the control population; wherein the one or more informative genetic variations distinguish one haplotype pattern from other haplotype patterns in a haplotype block;
   comparing, by the one or more processors, the determined frequency of the one or more informative genetic variations in the case population with the determined frequency of the one or more informative genetic variations in the control population;
   determining, by the one or more processors, and based on the comparison, differences in the frequency of the informative genetic variations between the case population and the control population;
   selecting, by the one or more processors, and based on the determined frequency differences, the one or more informative genetic variations having a frequency in the case population that is significantly different than a frequency in the control population;
   adding, by the one or more processors, the selected one or more informative genetic variations as pharmacogenomic-related genetic loci; and
   providing to the client device, by the one or more processors, a report including a description of the one or more informative genetic variations having a frequency in the case population that is significantly different than a frequency in the control population and an identification of the selected one or more informative genetic variations as pharmacogenomic-related genetic loci.

5. The computer-implemented method of claim 4, wherein the server is in communication with the database across the communications network.

6. The computer-implemented method of claim 4, wherein the server comprises the database.

7. The computer-implemented method of claim 4, wherein the server is configured to receive a request for the report from the client device.

8. The computer-implemented method of claim 4, wherein the one or more informative genetic variations are single-nucleotide polymorphisms.

* * * * *

SEQUENCE LISTING

<160> NUMBER OF SEQ ID NOS: 8

<210> SEQ ID NO 1
<211> LENGTH: 13
<212> TYPE: DNA
<213> ORGANISM: Artificial Sequence
<220> FEATURE:
<223> OTHER INFORMATION: Hypothetical sequence

<400> SEQUENCE: 1
agattcgata acg                                                          13

<210> SEQ ID NO 2
<211> LENGTH: 13
<212> TYPE: DNA
<213> ORGANISM: Artificial Sequence
<220> FEATURE:
<223> OTHER INFORMATION: Hypothetical Sequence

<400> SEQUENCE: 2
agactacata acg                                                          13

<210> SEQ ID NO 3
<211> LENGTH: 13
<212> TYPE: DNA
<213> ORGANISM: Artificial Sequence
<220> FEATURE:
<223> OTHER INFORMATION: Hypothetical Sequence

<400> SEQUENCE: 3
tatttcgata acg                                                          13

<210> SEQ ID NO 4
<211> LENGTH: 13
<212> TYPE: DNA
<213> ORGANISM: Artificial Sequence
<220> FEATURE:
<223> OTHER INFORMATION: Hypothetical Sequence

<400> SEQUENCE: 4
tatctacaat cac                                                          13

<210> SEQ ID NO 5
<211> LENGTH: 13
<212> TYPE: DNA
<213> ORGANISM: Artificial Sequence
<220> FEATURE:
<223> OTHER INFORMATION: hypothetical sequence

<400> SEQUENCE: 5
actgacccct ttt                                                          13

<210> SEQ ID NO 6
<211> LENGTH: 13
<212> TYPE: DNA
<213> ORGANISM: Artificial Sequence
<220> FEATURE:
<223> OTHER INFORMATION: Hypothetical Sequence

<400> SEQUENCE: 6
agtaacccct ttt                                                          13

<210> SEQ ID NO 7
<211> LENGTH: 13
<212> TYPE: DNA
<213> ORGANISM: Artificial Sequence
<220> FEATURE:
<223> OTHER INFORMATION: Hypothetical Sequence

<400> SEQUENCE: 7
actgacccct ttt                                                          13

<210> SEQ ID NO 8
<211> LENGTH: 13
<212> TYPE: DNA

```
-continued

<213> ORGANISM: Artificial Sequence
<220> FEATURE:
<223> OTHER INFORMATION: Hypothetical Sequence

<400> SEQUENCE: 8
agtgactctt taa                                                              13
```